US012774451B2

(12) United States Patent
Duchateau et al.

(10) Patent No.: US 12,774,451 B2
(45) Date of Patent: Oct. 27, 2026

(54) METHODS FOR IMPROVING FUNCTIONALITY IN NK CELL BY GENE INACTIVATION USING SPECIFIC ENDONUCLEASE

(71) Applicant: Cellectis, Paris (FR)

(72) Inventors: Philippe Duchateau, Draveil (FR); Jean-Pierre Cabaniols, Saint Lau la Foret (FR); Julien Valton, New York, NY (US)

(73) Assignee: Cellectis, Paris (FR)

( * ) Notice: Subject to any disclaimer, the term of this patent is extended or adjusted under 35 U.S.C. 154(b) by 0 days.

(21) Appl. No.: 15/578,946

(22) PCT Filed: Jun. 30, 2016

(86) PCT No.: PCT/EP2016/065326
§ 371 (c)(1),
(2) Date: Dec. 1, 2017

(87) PCT Pub. No.: WO2017/001572
PCT Pub. Date: Jan. 5, 2017

(65) Prior Publication Data

US 2018/0171298 A1 Jun. 21, 2018

(30) Foreign Application Priority Data

Jun. 30, 2015 (DK) .................................. 201570408

(51) Int. Cl.

| | |
|---|---|
| ***C12N 5/0783*** | (2010.01) |
| ***A61K 40/15*** | (2025.01) |
| ***A61K 40/42*** | (2025.01) |
| ***A61K 45/06*** | (2006.01) |
| ***C07K 14/47*** | (2006.01) |
| ***C07K 14/705*** | (2006.01) |
| ***C12N 9/12*** | (2006.01) |
| ***C12N 9/22*** | (2006.01) |
| ***C12N 15/63*** | (2006.01) |
| ***C12N 15/85*** | (2006.01) |
| ***C12N 15/86*** | (2006.01) |
| *A61K 39/00* | (2006.01) |

(52) U.S. Cl.
CPC ............ *C12N 5/0646* (2013.01); *A61K 40/15* (2025.01); *A61K 40/428* (2025.01); *A61K 45/06* (2013.01); *C07K 14/4703* (2013.01); *C07K 14/7051* (2013.01); *C12N 9/12* (2013.01); *C12N 9/22* (2013.01); *C12N 15/63* (2013.01); *C12N 15/85* (2013.01); *C12N 15/86* (2013.01); *A61K 2039/515* (2013.01); *A61K 2039/572* (2013.01); *C12N 2510/00* (2013.01)

(58) Field of Classification Search
CPC .......... C12N 5/0646; C12N 9/12; C12N 9/22; C12N 15/63; C12N 2510/00; A61K 35/17; A61K 45/06; A61K 2039/515; A61K 2039/572; C07K 14/4703; C07K 14/7051
See application file for complete search history.

(56) References Cited

U.S. PATENT DOCUMENTS 8,586,526 B2 * 11/2013 Gregory ......... C12Y 301/21004 514/1.1
2013/0117869 A1 * 5/2013 Duchateau et al.
2013/0315884 A1 * 11/2013 Galetto ................. C12N 15/85 424/93.71

FOREIGN PATENT DOCUMENTS

WO 2014/184143 A1 11/2014
WO 2014/184741 A1 11/2014
WO 2014/184744 A1 11/2014
WO WO-2015075195 A1 * 5/2015 ............. A61K 35/17
WO 2015/155341 A1 10/2015

OTHER PUBLICATIONS

Yang et al., International Immunopharmacology 17 (2013) 198-204. (Year: 2013).*
Zhao et al., Onco Targets and Therapy 2015:8 1553-1559. (Year: 2015).*
"Cellectis and Thermo Fisher Scientifc Enter Into Agreements on TALENT, a Leading Gene Editing Technology," Press release from Cellectis, published Jun. 5, 2014, pp. 1-3.*
Yang et al, International Immuno-pharmacology 17 (2013) 198-204.*
Zhao et al., OncoTargets and Therapy 2015:8 1553-1559.*
Godal et al, Biol Blood Marrow Transplant. May 2010, 16(5): 612-621.*
Carlsten et al, Frontiers in Immunology, 6: 1-9, Jun. 10, 2015.*
"Cellectis and Thermo Fisher Scientifc Enter Into Agreements on TALEN™, a Leading Gene Editing Technology," Press release from Cellectis, published Jun. 5, 2014, pp. 1-3.*
Ran et al., Nat. Protoc., 8(1 1): 2281-2308, Nov. 2013.*

(Continued)

*Primary Examiner* — Marcia S Noble
(74) *Attorney, Agent, or Firm* — Arrigo, Lee, Guttman & Mouta-Bellum LLP

(57) ABSTRACT

The present invention relates to methods for improving therapeutic activity of NK cell, such as their cytotoxic/cytolytic activity, to be used in immunotherapy, by gene editing. In particular, these methods comprise a step of reduction or inactivation of gene expression using specific endonuclease such as TAL-nuclease, CRISPR or Argonaute. An additional genetic modification can be performed by (over)expressing at least one gene involved in N K function. The present invention encompasses also engineered NK cell, pharmaceutical composition containing the same.

8 Claims, 2 Drawing Sheets

Specification includes a Sequence Listing.

(56) References Cited

OTHER PUBLICATIONS

Rezvani et al "The application of natural killer cell immunotherapy for the treatment of cancer," Frontiers in Immunology vol. 6, article 578. Nov. 2015 (Year: 2015).*
Wiernik et al. (Targeting natural killer cells to AML in vitro with a CD16x33 engager. Clin Cancer Res (2013) 19(14):3844-55) (Year: 2013).*
Tonn et al ("Treatment of patients with advanced cancer with the natural killer cell line NK-92;" Cytotherapy, 2013; 15: 1563e1570) (Year: 2013).*
Afolabi et al. (Immunology 158:63-69, 2019 (Year: 2019).*
Of Huang et al (Journal of Experimental Medicine 218(3). pp. 1-20, 2021 (Year: 2021).*
Cong et al: "Multiplex Genome Engineering Using CRISPR/Cas Systems", Science, vol. 339, No. 6121, Feb. 15, 2013 (Feb. 15, 2013), pp. 819-823.
Niu et al: "Applications of TALENs and CRISPR/Cas9 in Human Cells and Their Potentials for Gene Therapy", Molecular Biotechnology, vol. 56, No. 8, Aug. 2014 (Aug. 2014), pp. 681-688.
Ramalingam et al: "A CRISPR way to engineer the human genome", Genome Biology, Jan. 1, 2013 (Jan. 1, 2013), p. 107.
Armijo et al: "HIV/AIDS: modified stem cells in the spotlight", Cellular and Molecular Life Sciences, vol. 71, No. 14, Feb. 8, 2014 (Feb. 8, 2014), pp. 2641-2649.
Cong et al: "Multiplex Genome Engineering Using CRISPR/Cas Systems", HHS Public Access Author Manuscript, Oct. 11, 2013 (Oct. 11, 2013), pp. 1-9.
Cho et al: "Targeted genome engineering in human cells with the Cas9 RNA-guided endonuclease", Nature Biotechnology, Nature Publishing Group, US, vol. 31, No. 3, Mar. 1, 2013 (Mar. 1, 2013), pp. 230-232.
Tebas et al: "Gene Editing of CCR5 in Autologous CD4 T Cells of Persons Infected with HIV", New England Journal of Medicine, vol. 370, No. 10, Mar. 6, 2014 (Mar. 6, 2014), pp. 901-910.
Mashimo et al: "Generation of Knockout Rats with X-Linked Severe Combined Immunodeficiency (X-SCID) Using Zinc-Finger Nucleases", PLOS ONE, Public Library of Science, US, vol. 5, No. 1, Jan. 25, 2010 (Jan. 25, 2010), pp. E8870-E8871.
Perez et al: "Establishment of HIV-1 resistance in CD4+ T cells by genome editing using zinc-finger nucleases", Nature Biotechnology, vol. 26, No. 7, Jul. 1, 2008 (Jul. 1, 2008), pp. 808-816.
Voit et al: "Generation of an HIV Resistant T-cell Line by Targeted "Stacking" of Restriction Factors", Molecular Therapy, vol. 21, No. 4, Jan. 29, 2013 (Jan. 29, 2013), pp. 786-795.
European Patent Office, International Search Report in PCT/EP2016/065326, Oct. 12, 2016.
European Patent Office, Written Opinion in PCT/EP2016/065326, Oct. 12, 2016.
Hodge et al., Enhanced cytotoxic function of natural killer and natural killer T-like cells associated with decreased CD94 (Kp43) in the chronic obstructive pulmonary disease airway, I Respirology, Feb. 2013;18(2):369-76.
Homann et al., Expression of the p60 Autolysin Enhances NK Cell Activation and is Required for Listeria monocytogenes Expansion in IFN-γ-Responsive Mice. Journal of Immunology, 2007, vol. 178, pp. 2407-2414.

* cited by examiner

SEQUENCE LISTING

<160> NUMBER OF SEQ ID NOS: 30

<210> SEQ ID NO 1
<211> LENGTH: 49
<212> TYPE: DNA
<213> ORGANISM: homo sapiens
<220> FEATURE:
<223> OTHER INFORMATION: TGF-B Exon 2 target

<400> SEQUENCE: 1
ttgagctgga caccctggtg gggaaaggtc gctttgctga ggtctataa 49

<210> SEQ ID NO 2
<211> LENGTH: 936
<212> TYPE: PRT
<213> ORGANISM: artificial sequence
<220> FEATURE:
<223> OTHER INFORMATION: Left Talen for TGF-B Exon 2 target

<400> SEQUENCE: 2

Met Gly Asp Pro Lys Lys Lys Arg Lys Val Ile Asp Tyr Pro Tyr Asp
1 5 10 15

Val Pro Asp Tyr Ala Ile Asp Ile Ala Asp Leu Arg Thr Leu Gly Tyr
20 25 30

Ser Gln Gln Gln Gln Glu Lys Ile Lys Pro Lys Val Arg Ser Thr Val
35 40 45

Ala Gln His His Glu Ala Leu Val Gly His Gly Phe Thr His Ala His
50 55 60

Ile Val Ala Leu Ser Gln His Pro Ala Ala Leu Gly Thr Val Ala Val
65 70 75 80

Lys Tyr Gln Asp Met Ile Ala Ala Leu Pro Glu Ala Thr His Glu Ala
85 90 95

Ile Val Gly Val Gly Lys Gln Trp Ser Gly Ala Arg Ala Leu Glu Ala
100 105 110

Leu Leu Thr Val Ala Gly Glu Leu Arg Gly Pro Pro Leu Gln Leu Asp
115 120 125

Thr Gly Gln Leu Leu Lys Ile Ala Lys Arg Gly Gly Val Thr Ala Val
130 135 140

Glu Ala Val His Ala Trp Arg Asn Ala Leu Thr Gly Ala Pro Leu Asn
145 150 155 160

Leu Thr Pro Gln Gln Val Val Ala Ile Ala Ser Asn Gly Gly Gly Lys
165 170 175

Gln Ala Leu Glu Thr Val Gln Arg Leu Leu Pro Val Leu Cys Gln Ala
180 185 190

His Gly Leu Thr Pro Gln Gln Val Val Ala Ile Ala Ser Asn Asn Gly
195 200 205

Gly Lys Gln Ala Leu Glu Thr Val Gln Arg Leu Leu Pro Val Leu Cys
210 215 220

Gln Ala His Gly Leu Thr Pro Glu Gln Val Val Ala Ile Ala Ser Asn
225 230 235 240

Ile Gly Gly Lys Gln Ala Leu Glu Thr Val Gln Ala Leu Leu Pro Val
245 250 255

-continued

```
Leu Cys Gln Ala His Gly Leu Thr Pro Gln Gln Val Val Ala Ile Ala
            260                 265                 270

Ser Asn Asn Gly Gly Lys Gln Ala Leu Glu Thr Val Gln Arg Leu Leu
        275                 280                 285

Pro Val Leu Cys Gln Ala His Gly Leu Thr Pro Glu Gln Val Val Ala
    290                 295                 300

Ile Ala Ser His Asp Gly Gly Lys Gln Ala Leu Glu Thr Val Gln Arg
305                 310                 315                 320

Leu Leu Pro Val Leu Cys Gln Ala His Gly Leu Thr Pro Gln Gln Val
                325                 330                 335

Val Ala Ile Ala Ser Asn Gly Gly Gly Lys Gln Ala Leu Glu Thr Val
            340                 345                 350

Gln Arg Leu Leu Pro Val Leu Cys Gln Ala His Gly Leu Thr Pro Gln
        355                 360                 365

Gln Val Val Ala Ile Ala Ser Asn Asn Gly Gly Lys Gln Ala Leu Glu
    370                 375                 380

Thr Val Gln Arg Leu Leu Pro Val Leu Cys Gln Ala His Gly Leu Thr
385                 390                 395                 400

Pro Gln Gln Val Val Ala Ile Ala Ser Asn Asn Gly Gly Lys Gln Ala
                405                 410                 415

Leu Glu Thr Val Gln Arg Leu Leu Pro Val Leu Cys Gln Ala His Gly
            420                 425                 430

Leu Thr Pro Glu Gln Val Val Ala Ile Ala Ser Asn Ile Gly Gly Lys
        435                 440                 445

Gln Ala Leu Glu Thr Val Gln Ala Leu Leu Pro Val Leu Cys Gln Ala
    450                 455                 460

His Gly Leu Thr Pro Glu Gln Val Val Ala Ile Ala Ser His Asp Gly
465                 470                 475                 480

Gly Lys Gln Ala Leu Glu Thr Val Gln Arg Leu Leu Pro Val Leu Cys
                485                 490                 495

Gln Ala His Gly Leu Thr Pro Glu Gln Val Val Ala Ile Ala Ser Asn
            500                 505                 510

Ile Gly Gly Lys Gln Ala Leu Glu Thr Val Gln Ala Leu Leu Pro Val
        515                 520                 525

Leu Cys Gln Ala His Gly Leu Thr Pro Glu Gln Val Val Ala Ile Ala
    530                 535                 540

Ser His Asp Gly Gly Lys Gln Ala Leu Glu Thr Val Gln Arg Leu Leu
545                 550                 555                 560

Pro Val Leu Cys Gln Ala His Gly Leu Thr Pro Glu Gln Val Val Ala
                565                 570                 575

Ile Ala Ser His Asp Gly Gly Lys Gln Ala Leu Glu Thr Val Gln Arg
            580                 585                 590

Leu Leu Pro Val Leu Cys Gln Ala His Gly Leu Thr Pro Glu Gln Val
        595                 600                 605

Val Ala Ile Ala Ser His Asp Gly Gly Lys Gln Ala Leu Glu Thr Val
    610                 615                 620

Gln Arg Leu Leu Pro Val Leu Cys Gln Ala His Gly Leu Thr Pro Gln
625                 630                 635                 640

Gln Val Val Ala Ile Ala Ser Asn Gly Gly Gly Lys Gln Ala Leu Glu
                645                 650                 655

Thr Val Gln Arg Leu Leu Pro Val Leu Cys Gln Ala His Gly Leu Thr
            660                 665                 670
```

-continued

```
Pro Gln Gln Val Val Ala Ile Ala Ser Asn Gly Gly Gly Arg Pro Ala
        675                 680                 685

Leu Glu Ser Ile Val Ala Gln Leu Ser Arg Pro Asp Pro Ala Leu Ala
    690                 695                 700

Ala Leu Thr Asn Asp His Leu Val Ala Leu Ala Cys Leu Gly Gly Arg
705                 710                 715                 720

Pro Ala Leu Asp Ala Val Lys Lys Gly Leu Gly Asp Pro Ile Ser Arg
                725                 730                 735

Ser Gln Leu Val Lys Ser Glu Leu Glu Glu Lys Lys Ser Glu Leu Arg
            740                 745                 750

His Lys Leu Lys Tyr Val Pro His Glu Tyr Ile Glu Leu Ile Glu Ile
        755                 760                 765

Ala Arg Asn Ser Thr Gln Asp Arg Ile Leu Glu Met Lys Val Met Glu
    770                 775                 780

Phe Phe Met Lys Val Tyr Gly Tyr Arg Gly Lys His Leu Gly Gly Ser
785                 790                 795                 800

Arg Lys Pro Asp Gly Ala Ile Tyr Thr Val Gly Ser Pro Ile Asp Tyr
                805                 810                 815

Gly Val Ile Val Asp Thr Lys Ala Tyr Ser Gly Gly Tyr Asn Leu Pro
            820                 825                 830

Ile Gly Gln Ala Asp Glu Met Gln Arg Tyr Val Glu Glu Asn Gln Thr
        835                 840                 845

Arg Asn Lys His Ile Asn Pro Asn Glu Trp Trp Lys Val Tyr Pro Ser
    850                 855                 860

Ser Val Thr Glu Phe Lys Phe Leu Phe Val Ser Gly His Phe Lys Gly
865                 870                 875                 880

Asn Tyr Lys Ala Gln Leu Thr Arg Leu Asn His Ile Thr Asn Cys Asn
                885                 890                 895

Gly Ala Val Leu Ser Val Glu Glu Leu Leu Ile Gly Gly Glu Met Ile
            900                 905                 910

Lys Ala Gly Thr Leu Thr Leu Glu Glu Val Arg Arg Lys Phe Asn Asn
        915                 920                 925

Gly Glu Ile Asn Phe Ala Ala Asp
    930                 935


<210> SEQ ID NO 3
<211> LENGTH: 936
<212> TYPE: PRT
<213> ORGANISM: artificial sequence
<220> FEATURE:
<223> OTHER INFORMATION: Right Talen for TGF-B Exon 2 target

<400> SEQUENCE: 3

Met Gly Asp Pro Lys Lys Lys Arg Lys Val Ile Asp Tyr Pro Tyr Asp
1               5                   10                  15

Val Pro Asp Tyr Ala Ile Asp Ile Ala Asp Leu Arg Thr Leu Gly Tyr
            20                  25                  30

Ser Gln Gln Gln Gln Glu Lys Ile Lys Pro Lys Val Arg Ser Thr Val
        35                  40                  45

Ala Gln His His Glu Ala Leu Val Gly His Gly Phe Thr His Ala His
    50                  55                  60

Ile Val Ala Leu Ser Gln His Pro Ala Ala Leu Gly Thr Val Ala Val
65                  70                  75                  80

Lys Tyr Gln Asp Met Ile Ala Ala Leu Pro Glu Ala Thr His Glu Ala
                85                  90                  95
```

-continued

```
Ile Val Gly Val Gly Lys Gln Trp Ser Gly Ala Arg Ala Leu Glu Ala
            100                 105                 110

Leu Leu Thr Val Ala Gly Glu Leu Arg Gly Pro Pro Leu Gln Leu Asp
        115                 120                 125

Thr Gly Gln Leu Leu Lys Ile Ala Lys Arg Gly Gly Val Thr Ala Val
    130                 135                 140

Glu Ala Val His Ala Trp Arg Asn Ala Leu Thr Gly Ala Pro Leu Asn
145                 150                 155                 160

Leu Thr Pro Gln Gln Val Val Ala Ile Ala Ser Asn Gly Gly Gly Lys
                165                 170                 175

Gln Ala Leu Glu Thr Val Gln Arg Leu Leu Pro Val Leu Cys Gln Ala
            180                 185                 190

His Gly Leu Thr Pro Glu Gln Val Val Ala Ile Ala Ser Asn Ile Gly
        195                 200                 205

Gly Lys Gln Ala Leu Glu Thr Val Gln Ala Leu Leu Pro Val Leu Cys
    210                 215                 220

Gln Ala His Gly Leu Thr Pro Gln Gln Val Val Ala Ile Ala Ser Asn
225                 230                 235                 240

Gly Gly Gly Lys Gln Ala Leu Glu Thr Val Gln Arg Leu Leu Pro Val
                245                 250                 255

Leu Cys Gln Ala His Gly Leu Thr Pro Glu Gln Val Val Ala Ile Ala
            260                 265                 270

Ser Asn Ile Gly Gly Lys Gln Ala Leu Glu Thr Val Gln Ala Leu Leu
        275                 280                 285

Pro Val Leu Cys Gln Ala His Gly Leu Thr Pro Gln Gln Val Val Ala
    290                 295                 300

Ile Ala Ser Asn Asn Gly Gly Lys Gln Ala Leu Glu Thr Val Gln Arg
305                 310                 315                 320

Leu Leu Pro Val Leu Cys Gln Ala His Gly Leu Thr Pro Glu Gln Val
                325                 330                 335

Val Ala Ile Ala Ser Asn Ile Gly Gly Lys Gln Ala Leu Glu Thr Val
            340                 345                 350

Gln Ala Leu Leu Pro Val Leu Cys Gln Ala His Gly Leu Thr Pro Glu
        355                 360                 365

Gln Val Val Ala Ile Ala Ser His Asp Gly Gly Lys Gln Ala Leu Glu
    370                 375                 380

Thr Val Gln Arg Leu Leu Pro Val Leu Cys Gln Ala His Gly Leu Thr
385                 390                 395                 400

Pro Glu Gln Val Val Ala Ile Ala Ser His Asp Gly Gly Lys Gln Ala
                405                 410                 415

Leu Glu Thr Val Gln Arg Leu Leu Pro Val Leu Cys Gln Ala His Gly
            420                 425                 430

Leu Thr Pro Gln Gln Val Val Ala Ile Ala Ser Asn Gly Gly Gly Lys
        435                 440                 445

Gln Ala Leu Glu Thr Val Gln Arg Leu Leu Pro Val Leu Cys Gln Ala
    450                 455                 460

His Gly Leu Thr Pro Glu Gln Val Val Ala Ile Ala Ser His Asp Gly
465                 470                 475                 480

Gly Lys Gln Ala Leu Glu Thr Val Gln Arg Leu Leu Pro Val Leu Cys
                485                 490                 495

Gln Ala His Gly Leu Thr Pro Glu Gln Val Val Ala Ile Ala Ser Asn
            500                 505                 510

Ile Gly Gly Lys Gln Ala Leu Glu Thr Val Gln Ala Leu Leu Pro Val
```

```
        515                 520                 525

Leu Cys Gln Ala His Gly Leu Thr Pro Gln Gln Val Val Ala Ile Ala
    530                 535                 540

Ser Asn Asn Gly Gly Lys Gln Ala Leu Glu Thr Val Gln Arg Leu Leu
545                 550                 555                 560

Pro Val Leu Cys Gln Ala His Gly Leu Thr Pro Glu Gln Val Val Ala
                565                 570                 575

Ile Ala Ser His Asp Gly Gly Lys Gln Ala Leu Glu Thr Val Gln Arg
            580                 585                 590

Leu Leu Pro Val Leu Cys Gln Ala His Gly Leu Thr Pro Glu Gln Val
        595                 600                 605

Val Ala Ile Ala Ser Asn Ile Gly Gly Lys Gln Ala Leu Glu Thr Val
    610                 615                 620

Gln Ala Leu Leu Pro Val Leu Cys Gln Ala His Gly Leu Thr Pro Glu
625                 630                 635                 640

Gln Val Val Ala Ile Ala Ser Asn Ile Gly Gly Lys Gln Ala Leu Glu
                645                 650                 655

Thr Val Gln Ala Leu Leu Pro Val Leu Cys Gln Ala His Gly Leu Thr
            660                 665                 670

Pro Gln Gln Val Val Ala Ile Ala Ser Asn Gly Gly Gly Arg Pro Ala
        675                 680                 685

Leu Glu Ser Ile Val Ala Gln Leu Ser Arg Pro Asp Pro Ala Leu Ala
    690                 695                 700

Ala Leu Thr Asn Asp His Leu Val Ala Leu Ala Cys Leu Gly Gly Arg
705                 710                 715                 720

Pro Ala Leu Asp Ala Val Lys Lys Gly Leu Gly Asp Pro Ile Ser Arg
                725                 730                 735

Ser Gln Leu Val Lys Ser Glu Leu Glu Glu Lys Lys Ser Glu Leu Arg
            740                 745                 750

His Lys Leu Lys Tyr Val Pro His Glu Tyr Ile Glu Leu Ile Glu Ile
        755                 760                 765

Ala Arg Asn Ser Thr Gln Asp Arg Ile Leu Glu Met Lys Val Met Glu
    770                 775                 780

Phe Phe Met Lys Val Tyr Gly Tyr Arg Gly Lys His Leu Gly Gly Ser
785                 790                 795                 800

Arg Lys Pro Asp Gly Ala Ile Tyr Thr Val Gly Ser Pro Ile Asp Tyr
                805                 810                 815

Gly Val Ile Val Asp Thr Lys Ala Tyr Ser Gly Gly Tyr Asn Leu Pro
            820                 825                 830

Ile Gly Gln Ala Asp Glu Met Gln Arg Tyr Val Glu Glu Asn Gln Thr
        835                 840                 845

Arg Asn Lys His Ile Asn Pro Asn Glu Trp Trp Lys Val Tyr Pro Ser
    850                 855                 860

Ser Val Thr Glu Phe Lys Phe Leu Phe Val Ser Gly His Phe Lys Gly
865                 870                 875                 880

Asn Tyr Lys Ala Gln Leu Thr Arg Leu Asn His Ile Thr Asn Cys Asn
                885                 890                 895

Gly Ala Val Leu Ser Val Glu Glu Leu Leu Ile Gly Gly Glu Met Ile
            900                 905                 910

Lys Ala Gly Thr Leu Thr Leu Glu Glu Val Arg Arg Lys Phe Asn Asn
        915                 920                 925

Gly Glu Ile Asn Phe Ala Ala Asp
    930                 935
```

<210> SEQ ID NO 4
<211> LENGTH: 45
<212> TYPE: DNA
<213> ORGANISM: homo sapiens
<220> FEATURE:
<223> OTHER INFORMATION: Cbl-b Exon 2 target

<400> SEQUENCE: 4
tgtgccaaaa tcccaaactt cagttgaaaa atagcccacc atata 45

<210> SEQ ID NO 5
<211> LENGTH: 1065
<212> TYPE: PRT
<213> ORGANISM: artificial sequence
<220> FEATURE:
<223> OTHER INFORMATION: Left Talen for Cbl-b Exon 2 target

<400> SEQUENCE: 5

```
Met Gly Asp Pro Lys Lys Lys Arg Lys Val Ile Asp Tyr Pro Tyr Asp
1               5                   10                  15

Val Pro Asp Tyr Ala Ile Asp Ile Ala Asp Pro Ile Arg Ser Arg Thr
            20                  25                  30

Pro Ser Pro Ala Arg Glu Leu Leu Pro Gly Pro Gln Pro Asp Gly Val
        35                  40                  45

Gln Pro Thr Ala Asp Arg Gly Val Ser Pro Pro Ala Gly Gly Pro Leu
    50                  55                  60

Asp Gly Leu Pro Ala Arg Arg Thr Met Ser Arg Thr Arg Leu Pro Ser
65                  70                  75                  80

Pro Pro Ala Pro Ser Pro Ala Phe Ser Ala Gly Ser Phe Ser Asp Leu
                85                  90                  95

Leu Arg Gln Phe Asp Pro Ser Leu Phe Asn Thr Ser Leu Phe Asp Ser
            100                 105                 110

Leu Pro Pro Phe Gly Ala His His Thr Glu Ala Ala Thr Gly Glu Trp
        115                 120                 125

Asp Glu Val Gln Ser Gly Leu Arg Ala Ala Asp Ala Pro Pro Pro Thr
    130                 135                 140

Met Arg Val Ala Val Thr Ala Ala Arg Pro Pro Arg Ala Lys Pro Ala
145                 150                 155                 160

Pro Arg Arg Arg Ala Ala Gln Pro Ser Asp Ala Ser Pro Ala Ala Gln
                165                 170                 175

Val Asp Leu Arg Thr Leu Gly Tyr Ser Gln Gln Gln Gln Glu Lys Ile
            180                 185                 190

Lys Pro Lys Val Arg Ser Thr Val Ala Gln His His Glu Ala Leu Val
        195                 200                 205

Gly His Gly Phe Thr His Ala His Ile Val Ala Leu Ser Gln His Pro
    210                 215                 220

Ala Ala Leu Gly Thr Val Ala Val Lys Tyr Gln Asp Met Ile Ala Ala
225                 230                 235                 240

Leu Pro Glu Ala Thr His Glu Ala Ile Val Gly Val Gly Lys Gln Trp
                245                 250                 255

Ser Gly Ala Arg Ala Leu Glu Ala Leu Leu Thr Val Ala Gly Glu Leu
            260                 265                 270

Arg Gly Pro Pro Leu Gln Leu Asp Thr Gly Gln Leu Leu Lys Ile Ala
        275                 280                 285

Lys Arg Gly Gly Val Thr Ala Val Glu Ala Val His Ala Trp Arg Asn
    290                 295                 300
```

```
Ala Leu Thr Gly Ala Pro Leu Asn Leu Thr Pro Gln Gln Val Val Ala
305                 310                 315                 320

Ile Ala Ser Asn Asn Gly Gly Lys Gln Ala Leu Glu Thr Val Gln Arg
                325                 330                 335

Leu Leu Pro Val Leu Cys Gln Ala His Gly Leu Thr Pro Gln Gln Val
            340                 345                 350

Val Ala Ile Ala Ser Asn Gly Gly Gly Lys Gln Ala Leu Glu Thr Val
        355                 360                 365

Gln Arg Leu Leu Pro Val Leu Cys Gln Ala His Gly Leu Thr Pro Gln
    370                 375                 380

Gln Val Val Ala Ile Ala Ser Asn Asn Gly Gly Lys Gln Ala Leu Glu
385                 390                 395                 400

Thr Val Gln Arg Leu Leu Pro Val Leu Cys Gln Ala His Gly Leu Thr
                405                 410                 415

Pro Glu Gln Val Val Ala Ile Ala Ser His Asp Gly Gly Lys Gln Ala
            420                 425                 430

Leu Glu Thr Val Gln Arg Leu Leu Pro Val Leu Cys Gln Ala His Gly
        435                 440                 445

Leu Thr Pro Glu Gln Val Val Ala Ile Ala Ser His Asp Gly Gly Lys
    450                 455                 460

Gln Ala Leu Glu Thr Val Gln Arg Leu Leu Pro Val Leu Cys Gln Ala
465                 470                 475                 480

His Gly Leu Thr Pro Glu Gln Val Val Ala Ile Ala Ser Asn Ile Gly
                485                 490                 495

Gly Lys Gln Ala Leu Glu Thr Val Gln Ala Leu Leu Pro Val Leu Cys
            500                 505                 510

Gln Ala His Gly Leu Thr Pro Glu Gln Val Val Ala Ile Ala Ser Asn
        515                 520                 525

Ile Gly Gly Lys Gln Ala Leu Glu Thr Val Gln Ala Leu Leu Pro Val
    530                 535                 540

Leu Cys Gln Ala His Gly Leu Thr Pro Glu Gln Val Val Ala Ile Ala
545                 550                 555                 560

Ser Asn Ile Gly Gly Lys Gln Ala Leu Glu Thr Val Gln Ala Leu Leu
                565                 570                 575

Pro Val Leu Cys Gln Ala His Gly Leu Thr Pro Glu Gln Val Val Ala
            580                 585                 590

Ile Ala Ser Asn Ile Gly Gly Lys Gln Ala Leu Glu Thr Val Gln Ala
        595                 600                 605

Leu Leu Pro Val Leu Cys Gln Ala His Gly Leu Thr Pro Gln Gln Val
    610                 615                 620

Val Ala Ile Ala Ser Asn Gly Gly Gly Lys Gln Ala Leu Glu Thr Val
625                 630                 635                 640

Gln Arg Leu Leu Pro Val Leu Cys Gln Ala His Gly Leu Thr Pro Glu
                645                 650                 655

Gln Val Val Ala Ile Ala Ser His Asp Gly Gly Lys Gln Ala Leu Glu
            660                 665                 670

Thr Val Gln Arg Leu Leu Pro Val Leu Cys Gln Ala His Gly Leu Thr
        675                 680                 685

Pro Glu Gln Val Val Ala Ile Ala Ser His Asp Gly Gly Lys Gln Ala
    690                 695                 700

Leu Glu Thr Val Gln Arg Leu Leu Pro Val Leu Cys Gln Ala His Gly
705                 710                 715                 720
```

```
Leu Thr Pro Glu Gln Val Val Ala Ile Ala Ser His Asp Gly Gly Lys
                725                 730                 735

Gln Ala Leu Glu Thr Val Gln Arg Leu Leu Pro Val Leu Cys Gln Ala
            740                 745                 750

His Gly Leu Thr Pro Glu Gln Val Val Ala Ile Ala Ser Asn Ile Gly
        755                 760                 765

Gly Lys Gln Ala Leu Glu Thr Val Gln Ala Leu Leu Pro Val Leu Cys
    770                 775                 780

Gln Ala His Gly Leu Thr Pro Glu Gln Val Val Ala Ile Ala Ser Asn
785                 790                 795                 800

Ile Gly Gly Lys Gln Ala Leu Glu Thr Val Gln Ala Leu Leu Pro Val
                805                 810                 815

Leu Cys Gln Ala His Gly Leu Thr Pro Gln Gln Val Val Ala Ile Ala
            820                 825                 830

Ser Asn Gly Gly Gly Arg Pro Ala Leu Glu Ser Ile Val Ala Gln Leu
        835                 840                 845

Ser Arg Pro Asp Pro Ser Gly Ser Gly Ser Gly Gly Asp Pro Ile Ser
    850                 855                 860

Arg Ser Gln Leu Val Lys Ser Glu Leu Glu Glu Lys Lys Ser Glu Leu
865                 870                 875                 880

Arg His Lys Leu Lys Tyr Val Pro His Glu Tyr Ile Glu Leu Ile Glu
                885                 890                 895

Ile Ala Arg Asn Ser Thr Gln Asp Arg Ile Leu Glu Met Lys Val Met
            900                 905                 910

Glu Phe Phe Met Lys Val Tyr Gly Tyr Arg Gly Lys His Leu Gly Gly
        915                 920                 925

Ser Arg Lys Pro Asp Gly Ala Ile Tyr Thr Val Gly Ser Pro Ile Asp
    930                 935                 940

Tyr Gly Val Ile Val Asp Thr Lys Ala Tyr Ser Gly Gly Tyr Asn Leu
945                 950                 955                 960

Pro Ile Gly Gln Ala Asp Glu Met Gln Arg Tyr Val Glu Glu Asn Gln
                965                 970                 975

Thr Arg Asn Lys His Ile Asn Pro Asn Glu Trp Trp Lys Val Tyr Pro
            980                 985                 990

Ser Ser Val Thr Glu Phe Lys Phe Leu Phe Val Ser Gly His Phe Lys
        995                 1000                1005

Gly Asn Tyr Lys Ala Gln Leu Thr Arg Leu Asn His Ile Thr Asn Cys
    1010                1015                1020

Asn Gly Ala Val Leu Ser Val Glu Glu Leu Leu Ile Gly Gly Glu Met
1025                1030                1035                1040

Ile Lys Ala Gly Thr Leu Thr Leu Glu Glu Val Arg Arg Lys Phe Asn
                1045                1050                1055

Asn Gly Glu Ile Asn Phe Ala Ala Asp
            1060                1065


<210> SEQ ID NO 6
<211> LENGTH: 1065
<212> TYPE: PRT
<213> ORGANISM: artificial sequence
<220> FEATURE:
<223> OTHER INFORMATION: Right Talen for TGF-B Exon 2 target

<400> SEQUENCE: 6

Met Gly Asp Pro Lys Lys Lys Arg Lys Val Ile Asp Tyr Pro Tyr Asp
1               5                   10                  15
```

-continued

```
Val Pro Asp Tyr Ala Ile Asp Ile Ala Asp Pro Ile Arg Ser Arg Thr
            20                  25                  30

Pro Ser Pro Ala Arg Glu Leu Leu Pro Gly Pro Gln Pro Asp Gly Val
        35                  40                  45

Gln Pro Thr Ala Asp Arg Gly Val Ser Pro Pro Ala Gly Gly Pro Leu
    50                  55                  60

Asp Gly Leu Pro Ala Arg Arg Thr Met Ser Arg Thr Arg Leu Pro Ser
65                  70                  75                  80

Pro Pro Ala Pro Ser Pro Ala Phe Ser Ala Gly Ser Phe Ser Asp Leu
                85                  90                  95

Leu Arg Gln Phe Asp Pro Ser Leu Phe Asn Thr Ser Leu Phe Asp Ser
            100                 105                 110

Leu Pro Pro Phe Gly Ala His His Thr Glu Ala Ala Thr Gly Glu Trp
        115                 120                 125

Asp Glu Val Gln Ser Gly Leu Arg Ala Ala Asp Ala Pro Pro Pro Thr
    130                 135                 140

Met Arg Val Ala Val Thr Ala Ala Arg Pro Pro Arg Ala Lys Pro Ala
145                 150                 155                 160

Pro Arg Arg Arg Ala Ala Gln Pro Ser Asp Ala Ser Pro Ala Ala Gln
                165                 170                 175

Val Asp Leu Arg Thr Leu Gly Tyr Ser Gln Gln Gln Gln Glu Lys Ile
            180                 185                 190

Lys Pro Lys Val Arg Ser Thr Val Ala Gln His His Glu Ala Leu Val
        195                 200                 205

Gly His Gly Phe Thr His Ala His Ile Val Ala Leu Ser Gln His Pro
    210                 215                 220

Ala Ala Leu Gly Thr Val Ala Val Lys Tyr Gln Asp Met Ile Ala Ala
225                 230                 235                 240

Leu Pro Glu Ala Thr His Glu Ala Ile Val Gly Val Gly Lys Gln Trp
                245                 250                 255

Ser Gly Ala Arg Ala Leu Glu Ala Leu Leu Thr Val Ala Gly Glu Leu
            260                 265                 270

Arg Gly Pro Pro Leu Gln Leu Asp Thr Gly Gln Leu Leu Lys Ile Ala
        275                 280                 285

Lys Arg Gly Gly Val Thr Ala Val Glu Ala Val His Ala Trp Arg Asn
    290                 295                 300

Ala Leu Thr Gly Ala Pro Leu Asn Leu Thr Pro Glu Gln Val Val Ala
305                 310                 315                 320

Ile Ala Ser Asn Ile Gly Gly Lys Gln Ala Leu Glu Thr Val Gln Ala
                325                 330                 335

Leu Leu Pro Val Leu Cys Gln Ala His Gly Leu Thr Pro Gln Gln Val
            340                 345                 350

Val Ala Ile Ala Ser Asn Gly Gly Gly Lys Gln Ala Leu Glu Thr Val
        355                 360                 365

Gln Arg Leu Leu Pro Val Leu Cys Gln Ala His Gly Leu Thr Pro Glu
    370                 375                 380

Gln Val Val Ala Ile Ala Ser Asn Ile Gly Gly Lys Gln Ala Leu Glu
385                 390                 395                 400

Thr Val Gln Ala Leu Leu Pro Val Leu Cys Gln Ala His Gly Leu Thr
                405                 410                 415

Pro Gln Gln Val Val Ala Ile Ala Ser Asn Gly Gly Gly Lys Gln Ala
            420                 425                 430

Leu Glu Thr Val Gln Arg Leu Leu Pro Val Leu Cys Gln Ala His Gly
```

```
        435                 440                 445

Leu Thr Pro Gln Gln Val Val Ala Ile Ala Ser Asn Asn Gly Gly Lys
    450                 455                 460

Gln Ala Leu Glu Thr Val Gln Arg Leu Leu Pro Val Leu Cys Gln Ala
465                 470                 475                 480

His Gly Leu Thr Pro Gln Gln Val Val Ala Ile Ala Ser Asn Asn Gly
                485                 490                 495

Gly Lys Gln Ala Leu Glu Thr Val Gln Arg Leu Leu Pro Val Leu Cys
            500                 505                 510

Gln Ala His Gly Leu Thr Pro Gln Gln Val Val Ala Ile Ala Ser Asn
        515                 520                 525

Gly Gly Gly Lys Gln Ala Leu Glu Thr Val Gln Arg Leu Leu Pro Val
    530                 535                 540

Leu Cys Gln Ala His Gly Leu Thr Pro Gln Gln Val Val Ala Ile Ala
545                 550                 555                 560

Ser Asn Asn Gly Gly Lys Gln Ala Leu Glu Thr Val Gln Arg Leu Leu
                565                 570                 575

Pro Val Leu Cys Gln Ala His Gly Leu Thr Pro Gln Gln Val Val Ala
            580                 585                 590

Ile Ala Ser Asn Asn Gly Gly Lys Gln Ala Leu Glu Thr Val Gln Arg
        595                 600                 605

Leu Leu Pro Val Leu Cys Gln Ala His Gly Leu Thr Pro Gln Gln Val
    610                 615                 620

Val Ala Ile Ala Ser Asn Asn Gly Gly Lys Gln Ala Leu Glu Thr Val
625                 630                 635                 640

Gln Arg Leu Leu Pro Val Leu Cys Gln Ala His Gly Leu Thr Pro Glu
                645                 650                 655

Gln Val Val Ala Ile Ala Ser His Asp Gly Gly Lys Gln Ala Leu Glu
            660                 665                 670

Thr Val Gln Arg Leu Leu Pro Val Leu Cys Gln Ala His Gly Leu Thr
        675                 680                 685

Pro Gln Gln Val Val Ala Ile Ala Ser Asn Gly Gly Gly Lys Gln Ala
    690                 695                 700

Leu Glu Thr Val Gln Arg Leu Leu Pro Val Leu Cys Gln Ala His Gly
705                 710                 715                 720

Leu Thr Pro Glu Gln Val Val Ala Ile Ala Ser Asn Ile Gly Gly Lys
                725                 730                 735

Gln Ala Leu Glu Thr Val Gln Ala Leu Leu Pro Val Leu Cys Gln Ala
            740                 745                 750

His Gly Leu Thr Pro Gln Gln Val Val Ala Ile Ala Ser Asn Gly Gly
        755                 760                 765

Gly Lys Gln Ala Leu Glu Thr Val Gln Arg Leu Leu Pro Val Leu Cys
    770                 775                 780

Gln Ala His Gly Leu Thr Pro Gln Gln Val Val Ala Ile Ala Ser Asn
785                 790                 795                 800

Gly Gly Gly Lys Gln Ala Leu Glu Thr Val Gln Arg Leu Leu Pro Val
                805                 810                 815

Leu Cys Gln Ala His Gly Leu Thr Pro Gln Gln Val Val Ala Ile Ala
            820                 825                 830

Ser Asn Gly Gly Gly Arg Pro Ala Leu Glu Ser Ile Val Ala Gln Leu
        835                 840                 845

Ser Arg Pro Asp Pro Ser Gly Ser Gly Ser Gly Gly Asp Pro Ile Ser
    850                 855                 860
```

```
Arg Ser Gln Leu Val Lys Ser Glu Leu Glu Glu Lys Lys Ser Glu Leu
865                 870                 875                 880

Arg His Lys Leu Lys Tyr Val Pro His Glu Tyr Ile Glu Leu Ile Glu
                885                 890                 895

Ile Ala Arg Asn Ser Thr Gln Asp Arg Ile Leu Glu Met Lys Val Met
            900                 905                 910

Glu Phe Phe Met Lys Val Tyr Gly Tyr Arg Gly Lys His Leu Gly Gly
        915                 920                 925

Ser Arg Lys Pro Asp Gly Ala Ile Tyr Thr Val Gly Ser Pro Ile Asp
    930                 935                 940

Tyr Gly Val Ile Val Asp Thr Lys Ala Tyr Ser Gly Gly Tyr Asn Leu
945                 950                 955                 960

Pro Ile Gly Gln Ala Asp Glu Met Gln Arg Tyr Val Glu Glu Asn Gln
                965                 970                 975

Thr Arg Asn Lys His Ile Asn Pro Asn Glu Trp Trp Lys Val Tyr Pro
            980                 985                 990

Ser Ser Val Thr Glu Phe Lys Phe Leu Phe Val Ser Gly His Phe Lys
        995                 1000                1005

Gly Asn Tyr Lys Ala Gln Leu Thr Arg Leu Asn His Ile Thr Asn Cys
    1010                1015                1020

Asn Gly Ala Val Leu Ser Val Glu Glu Leu Leu Ile Gly Gly Glu Met
1025                1030                1035                1040

Ile Lys Ala Gly Thr Leu Thr Leu Glu Glu Val Arg Arg Lys Phe Asn
                1045                1050                1055

Asn Gly Glu Ile Asn Phe Ala Ala Asp
            1060                1065


<210> SEQ ID NO 7
<211> LENGTH: 45
<212> TYPE: DNA
<213> ORGANISM: homo sapiens
<220> FEATURE:
<223> OTHER INFORMATION: Cbl-b Exon 3 target

<400> SEQUENCE: 7

tgctgctgaa ttctggagaa agttttttgg agacaagtaa gtaaa                    45


<210> SEQ ID NO 8
<211> LENGTH: 1065
<212> TYPE: PRT
<213> ORGANISM: artificial sequence
<220> FEATURE:
<223> OTHER INFORMATION: Left Talen for Cbl-b Exon 3 target

<400> SEQUENCE: 8

Met Gly Asp Pro Lys Lys Lys Arg Lys Val Ile Asp Tyr Pro Tyr Asp
1               5                   10                  15

Val Pro Asp Tyr Ala Ile Asp Ile Ala Asp Pro Ile Arg Ser Arg Thr
            20                  25                  30

Pro Ser Pro Ala Arg Glu Leu Leu Pro Gly Pro Gln Pro Asp Gly Val
        35                  40                  45

Gln Pro Thr Ala Asp Arg Gly Val Ser Pro Pro Ala Gly Gly Pro Leu
    50                  55                  60

Asp Gly Leu Pro Ala Arg Arg Thr Met Ser Arg Thr Arg Leu Pro Ser
65                  70                  75                  80

Pro Pro Ala Pro Ser Pro Ala Phe Ser Ala Gly Ser Phe Ser Asp Leu
                85                  90                  95
```

```
Leu Arg Gln Phe Asp Pro Ser Leu Phe Asn Thr Ser Leu Phe Asp Ser
            100                 105                 110

Leu Pro Pro Phe Gly Ala His His Thr Glu Ala Ala Thr Gly Glu Trp
        115                 120                 125

Asp Glu Val Gln Ser Gly Leu Arg Ala Ala Asp Ala Pro Pro Pro Thr
    130                 135                 140

Met Arg Val Ala Val Thr Ala Ala Arg Pro Pro Arg Ala Lys Pro Ala
145                 150                 155                 160

Pro Arg Arg Arg Ala Ala Gln Pro Ser Asp Ala Ser Pro Ala Ala Gln
                165                 170                 175

Val Asp Leu Arg Thr Leu Gly Tyr Ser Gln Gln Gln Gln Glu Lys Ile
            180                 185                 190

Lys Pro Lys Val Arg Ser Thr Val Ala Gln His His Glu Ala Leu Val
        195                 200                 205

Gly His Gly Phe Thr His Ala His Ile Val Ala Leu Ser Gln His Pro
    210                 215                 220

Ala Ala Leu Gly Thr Val Ala Val Lys Tyr Gln Asp Met Ile Ala Ala
225                 230                 235                 240

Leu Pro Glu Ala Thr His Glu Ala Ile Val Gly Val Gly Lys Gln Trp
                245                 250                 255

Ser Gly Ala Arg Ala Leu Glu Ala Leu Leu Thr Val Ala Gly Glu Leu
            260                 265                 270

Arg Gly Pro Pro Leu Gln Leu Asp Thr Gly Gln Leu Leu Lys Ile Ala
        275                 280                 285

Lys Arg Gly Gly Val Thr Ala Val Glu Ala Val His Ala Trp Arg Asn
    290                 295                 300

Ala Leu Thr Gly Ala Pro Leu Asn Leu Thr Pro Gln Gln Val Val Ala
305                 310                 315                 320

Ile Ala Ser Asn Asn Gly Gly Lys Gln Ala Leu Glu Thr Val Gln Arg
                325                 330                 335

Leu Leu Pro Val Leu Cys Gln Ala His Gly Leu Thr Pro Glu Gln Val
            340                 345                 350

Val Ala Ile Ala Ser His Asp Gly Gly Lys Gln Ala Leu Glu Thr Val
        355                 360                 365

Gln Arg Leu Leu Pro Val Leu Cys Gln Ala His Gly Leu Thr Pro Gln
    370                 375                 380

Gln Val Val Ala Ile Ala Ser Asn Gly Gly Gly Lys Gln Ala Leu Glu
385                 390                 395                 400

Thr Val Gln Arg Leu Leu Pro Val Leu Cys Gln Ala His Gly Leu Thr
                405                 410                 415

Pro Gln Gln Val Val Ala Ile Ala Ser Asn Asn Gly Gly Lys Gln Ala
            420                 425                 430

Leu Glu Thr Val Gln Arg Leu Leu Pro Val Leu Cys Gln Ala His Gly
        435                 440                 445

Leu Thr Pro Glu Gln Val Val Ala Ile Ala Ser His Asp Gly Gly Lys
    450                 455                 460

Gln Ala Leu Glu Thr Val Gln Arg Leu Leu Pro Val Leu Cys Gln Ala
465                 470                 475                 480

His Gly Leu Thr Pro Gln Gln Val Val Ala Ile Ala Ser Asn Gly Gly
                485                 490                 495

Gly Lys Gln Ala Leu Glu Thr Val Gln Arg Leu Leu Pro Val Leu Cys
            500                 505                 510
```

```
Gln Ala His Gly Leu Thr Pro Gln Gln Val Val Ala Ile Ala Ser Asn
        515                 520                 525

Asn Gly Gly Lys Gln Ala Leu Glu Thr Val Gln Arg Leu Leu Pro Val
    530                 535                 540

Leu Cys Gln Ala His Gly Leu Thr Pro Glu Gln Val Val Ala Ile Ala
545                 550                 555                 560

Ser Asn Ile Gly Gly Lys Gln Ala Leu Glu Thr Val Gln Ala Leu Leu
                565                 570                 575

Pro Val Leu Cys Gln Ala His Gly Leu Thr Pro Glu Gln Val Val Ala
            580                 585                 590

Ile Ala Ser Asn Ile Gly Gly Lys Gln Ala Leu Glu Thr Val Gln Ala
        595                 600                 605

Leu Leu Pro Val Leu Cys Gln Ala His Gly Leu Thr Pro Gln Gln Val
    610                 615                 620

Val Ala Ile Ala Ser Asn Gly Gly Gly Lys Gln Ala Leu Glu Thr Val
625                 630                 635                 640

Gln Arg Leu Leu Pro Val Leu Cys Gln Ala His Gly Leu Thr Pro Gln
                645                 650                 655

Gln Val Val Ala Ile Ala Ser Asn Gly Gly Gly Lys Gln Ala Leu Glu
            660                 665                 670

Thr Val Gln Arg Leu Leu Pro Val Leu Cys Gln Ala His Gly Leu Thr
        675                 680                 685

Pro Glu Gln Val Val Ala Ile Ala Ser His Asp Gly Gly Lys Gln Ala
    690                 695                 700

Leu Glu Thr Val Gln Arg Leu Leu Pro Val Leu Cys Gln Ala His Gly
705                 710                 715                 720

Leu Thr Pro Gln Gln Val Val Ala Ile Ala Ser Asn Gly Gly Gly Lys
                725                 730                 735

Gln Ala Leu Glu Thr Val Gln Arg Leu Leu Pro Val Leu Cys Gln Ala
            740                 745                 750

His Gly Leu Thr Pro Gln Gln Val Val Ala Ile Ala Ser Asn Asn Gly
        755                 760                 765

Gly Lys Gln Ala Leu Glu Thr Val Gln Arg Leu Leu Pro Val Leu Cys
    770                 775                 780

Gln Ala His Gly Leu Thr Pro Gln Gln Val Val Ala Ile Ala Ser Asn
785                 790                 795                 800

Asn Gly Gly Lys Gln Ala Leu Glu Thr Val Gln Arg Leu Leu Pro Val
                805                 810                 815

Leu Cys Gln Ala His Gly Leu Thr Pro Gln Gln Val Val Ala Ile Ala
            820                 825                 830

Ser Asn Gly Gly Gly Arg Pro Ala Leu Glu Ser Ile Val Ala Gln Leu
        835                 840                 845

Ser Arg Pro Asp Pro Ser Gly Ser Gly Ser Gly Gly Asp Pro Ile Ser
    850                 855                 860

Arg Ser Gln Leu Val Lys Ser Glu Leu Glu Glu Lys Lys Ser Glu Leu
865                 870                 875                 880

Arg His Lys Leu Lys Tyr Val Pro His Glu Tyr Ile Glu Leu Ile Glu
                885                 890                 895

Ile Ala Arg Asn Ser Thr Gln Asp Arg Ile Leu Glu Met Lys Val Met
            900                 905                 910

Glu Phe Phe Met Lys Val Tyr Gly Tyr Arg Gly Lys His Leu Gly Gly
        915                 920                 925

Ser Arg Lys Pro Asp Gly Ala Ile Tyr Thr Val Gly Ser Pro Ile Asp
```

930 935 940

Tyr Gly Val Ile Val Asp Thr Lys Ala Tyr Ser Gly Gly Tyr Asn Leu
945 950 955 960

Pro Ile Gly Gln Ala Asp Glu Met Gln Arg Tyr Val Glu Glu Asn Gln
965 970 975

Thr Arg Asn Lys His Ile Asn Pro Asn Glu Trp Trp Lys Val Tyr Pro
980 985 990

Ser Ser Val Thr Glu Phe Lys Phe Leu Phe Val Ser Gly His Phe Lys
995 1000 1005

Gly Asn Tyr Lys Ala Gln Leu Thr Arg Leu Asn His Ile Thr Asn Cys
1010 1015 1020

Asn Gly Ala Val Leu Ser Val Glu Glu Leu Leu Ile Gly Gly Glu Met
1025 1030 1035 1040

Ile Lys Ala Gly Thr Leu Thr Leu Glu Glu Val Arg Arg Lys Phe Asn
1045 1050 1055

Asn Gly Glu Ile Asn Phe Ala Ala Asp
1060 1065

<210> SEQ ID NO 9
<211> LENGTH: 1065
<212> TYPE: PRT
<213> ORGANISM: artificial sequence
<220> FEATURE:
<223> OTHER INFORMATION: Right Talen for TGF-B Exon 3 target

<400> SEQUENCE: 9

Met Gly Asp Pro Lys Lys Lys Arg Lys Val Ile Asp Tyr Pro Tyr Asp
1 5 10 15

Val Pro Asp Tyr Ala Ile Asp Ile Ala Asp Pro Ile Arg Ser Arg Thr
20 25 30

Pro Ser Pro Ala Arg Glu Leu Leu Pro Gly Pro Gln Pro Asp Gly Val
35 40 45

Gln Pro Thr Ala Asp Arg Gly Val Ser Pro Pro Ala Gly Gly Pro Leu
50 55 60

Asp Gly Leu Pro Ala Arg Arg Thr Met Ser Arg Thr Arg Leu Pro Ser
65 70 75 80

Pro Pro Ala Pro Ser Pro Ala Phe Ser Ala Gly Ser Phe Ser Asp Leu
85 90 95

Leu Arg Gln Phe Asp Pro Ser Leu Phe Asn Thr Ser Leu Phe Asp Ser
100 105 110

Leu Pro Pro Phe Gly Ala His His Thr Glu Ala Ala Thr Gly Glu Trp
115 120 125

Asp Glu Val Gln Ser Gly Leu Arg Ala Ala Asp Ala Pro Pro Pro Thr
130 135 140

Met Arg Val Ala Val Thr Ala Ala Arg Pro Pro Arg Ala Lys Pro Ala
145 150 155 160

Pro Arg Arg Arg Ala Ala Gln Pro Ser Asp Ala Ser Pro Ala Ala Gln
165 170 175

Val Asp Leu Arg Thr Leu Gly Tyr Ser Gln Gln Gln Gln Glu Lys Ile
180 185 190

Lys Pro Lys Val Arg Ser Thr Val Ala Gln His His Glu Ala Leu Val
195 200 205

Gly His Gly Phe Thr His Ala His Ile Val Ala Leu Ser Gln His Pro
210 215 220

Ala Ala Leu Gly Thr Val Ala Val Lys Tyr Gln Asp Met Ile Ala Ala

-continued

```
225                 230                 235                 240

Leu Pro Glu Ala Thr His Glu Ala Ile Val Gly Val Gly Lys Gln Trp
                245                 250                 255

Ser Gly Ala Arg Ala Leu Glu Ala Leu Leu Thr Val Ala Gly Glu Leu
            260                 265                 270

Arg Gly Pro Pro Leu Gln Leu Asp Thr Gly Gln Leu Leu Lys Ile Ala
        275                 280                 285

Lys Arg Gly Gly Val Thr Ala Val Glu Ala Val His Ala Trp Arg Asn
    290                 295                 300

Ala Leu Thr Gly Ala Pro Leu Asn Leu Thr Pro Gln Gln Val Val Ala
305                 310                 315                 320

Ile Ala Ser Asn Gly Gly Gly Lys Gln Ala Leu Glu Thr Val Gln Arg
                325                 330                 335

Leu Leu Pro Val Leu Cys Gln Ala His Gly Leu Thr Pro Gln Gln Val
            340                 345                 350

Val Ala Ile Ala Ser Asn Gly Gly Gly Lys Gln Ala Leu Glu Thr Val
        355                 360                 365

Gln Arg Leu Leu Pro Val Leu Cys Gln Ala His Gly Leu Thr Pro Glu
    370                 375                 380

Gln Val Val Ala Ile Ala Ser Asn Ile Gly Gly Lys Gln Ala Leu Glu
385                 390                 395                 400

Thr Val Gln Ala Leu Leu Pro Val Leu Cys Gln Ala His Gly Leu Thr
                405                 410                 415

Pro Glu Gln Val Val Ala Ile Ala Ser His Asp Gly Gly Lys Gln Ala
            420                 425                 430

Leu Glu Thr Val Gln Arg Leu Leu Pro Val Leu Cys Gln Ala His Gly
        435                 440                 445

Leu Thr Pro Gln Gln Val Val Ala Ile Ala Ser Asn Gly Gly Gly Lys
    450                 455                 460

Gln Ala Leu Glu Thr Val Gln Arg Leu Leu Pro Val Leu Cys Gln Ala
465                 470                 475                 480

His Gly Leu Thr Pro Gln Gln Val Val Ala Ile Ala Ser Asn Gly Gly
                485                 490                 495

Gly Lys Gln Ala Leu Glu Thr Val Gln Arg Leu Leu Pro Val Leu Cys
            500                 505                 510

Gln Ala His Gly Leu Thr Pro Glu Gln Val Val Ala Ile Ala Ser Asn
        515                 520                 525

Ile Gly Gly Lys Gln Ala Leu Glu Thr Val Gln Ala Leu Leu Pro Val
    530                 535                 540

Leu Cys Gln Ala His Gly Leu Thr Pro Glu Gln Val Val Ala Ile Ala
545                 550                 555                 560

Ser His Asp Gly Gly Lys Gln Ala Leu Glu Thr Val Gln Arg Leu Leu
                565                 570                 575

Pro Val Leu Cys Gln Ala His Gly Leu Thr Pro Gln Gln Val Val Ala
            580                 585                 590

Ile Ala Ser Asn Gly Gly Gly Lys Gln Ala Leu Glu Thr Val Gln Arg
        595                 600                 605

Leu Leu Pro Val Leu Cys Gln Ala His Gly Leu Thr Pro Gln Gln Val
    610                 615                 620

Val Ala Ile Ala Ser Asn Gly Gly Gly Lys Gln Ala Leu Glu Thr Val
625                 630                 635                 640

Gln Arg Leu Leu Pro Val Leu Cys Gln Ala His Gly Leu Thr Pro Gln
                645                 650                 655
```

```
Gln Val Val Ala Ile Ala Ser Asn Asn Gly Gly Lys Gln Ala Leu Glu
            660                 665                 670

Thr Val Gln Arg Leu Leu Pro Val Leu Cys Gln Ala His Gly Leu Thr
        675                 680                 685

Pro Gln Gln Val Val Ala Ile Ala Ser Asn Gly Gly Gly Lys Gln Ala
    690                 695                 700

Leu Glu Thr Val Gln Arg Leu Leu Pro Val Leu Cys Gln Ala His Gly
705                 710                 715                 720

Leu Thr Pro Glu Gln Val Val Ala Ile Ala Ser His Asp Gly Gly Lys
                725                 730                 735

Gln Ala Leu Glu Thr Val Gln Arg Leu Leu Pro Val Leu Cys Gln Ala
            740                 745                 750

His Gly Leu Thr Pro Gln Gln Val Val Ala Ile Ala Ser Asn Gly Gly
        755                 760                 765

Gly Lys Gln Ala Leu Glu Thr Val Gln Arg Leu Leu Pro Val Leu Cys
    770                 775                 780

Gln Ala His Gly Leu Thr Pro Glu Gln Val Val Ala Ile Ala Ser His
785                 790                 795                 800

Asp Gly Gly Lys Gln Ala Leu Glu Thr Val Gln Arg Leu Leu Pro Val
                805                 810                 815

Leu Cys Gln Ala His Gly Leu Thr Pro Gln Gln Val Val Ala Ile Ala
            820                 825                 830

Ser Asn Gly Gly Gly Arg Pro Ala Leu Glu Ser Ile Val Ala Gln Leu
        835                 840                 845

Ser Arg Pro Asp Pro Ser Gly Ser Gly Ser Gly Gly Asp Pro Ile Ser
    850                 855                 860

Arg Ser Gln Leu Val Lys Ser Glu Leu Glu Glu Lys Lys Ser Glu Leu
865                 870                 875                 880

Arg His Lys Leu Lys Tyr Val Pro His Glu Tyr Ile Glu Leu Ile Glu
                885                 890                 895

Ile Ala Arg Asn Ser Thr Gln Asp Arg Ile Leu Glu Met Lys Val Met
            900                 905                 910

Glu Phe Phe Met Lys Val Tyr Gly Tyr Arg Gly Lys His Leu Gly Gly
        915                 920                 925

Ser Arg Lys Pro Asp Gly Ala Ile Tyr Thr Val Gly Ser Pro Ile Asp
    930                 935                 940

Tyr Gly Val Ile Val Asp Thr Lys Ala Tyr Ser Gly Gly Tyr Asn Leu
945                 950                 955                 960

Pro Ile Gly Gln Ala Asp Glu Met Gln Arg Tyr Val Glu Glu Asn Gln
                965                 970                 975

Thr Arg Asn Lys His Ile Asn Pro Asn Glu Trp Trp Lys Val Tyr Pro
            980                 985                 990

Ser Ser Val Thr Glu Phe Lys Phe Leu Phe Val Ser Gly His Phe Lys
        995                 1000                1005

Gly Asn Tyr Lys Ala Gln Leu Thr Arg Leu Asn His Ile Thr Asn Cys
    1010                1015                1020

Asn Gly Ala Val Leu Ser Val Glu Glu Leu Leu Ile Gly Gly Glu Met
1025                1030                1035                1040

Ile Lys Ala Gly Thr Leu Thr Leu Glu Glu Val Arg Arg Lys Phe Asn
                1045                1050                1055

Asn Gly Glu Ile Asn Phe Ala Ala Asp
            1060                1065
```

<210> SEQ ID NO 10
<211> LENGTH: 557
<212> TYPE: PRT
<213> ORGANISM: homo sapiens
<220> FEATURE:
<223> OTHER INFORMATION: CD19 antigen

<400> SEQUENCE: 10

```
Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe Phe Lys Val
                325                 330                 335

Thr Pro Pro Pro Gly Ser Gly Pro Gln Asn Gln Tyr Gly Asn Val Leu
            340                 345                 350

Ser Leu Pro Thr Pro Thr Ser Gly Leu Gly Arg Ala Gln Arg Trp Ala
        355                 360                 365
```

```
Ala Gly Leu Gly Gly Thr Ala Pro Ser Tyr Gly Asn Pro Ser Ser Asp
    370                 375                 380

Val Gln Ala Asp Gly Ala Leu Gly Ser Arg Ser Pro Pro Gly Val Gly
385                 390                 395                 400

Pro Glu Glu Glu Glu Gly Glu Gly Tyr Glu Glu Pro Asp Ser Glu Glu
                405                 410                 415

Asp Ser Glu Phe Tyr Glu Asn Asp Ser Asn Leu Gly Gln Asp Gln Leu
            420                 425                 430

Ser Gln Asp Gly Ser Gly Tyr Glu Asn Pro Glu Asp Glu Pro Leu Gly
        435                 440                 445

Pro Glu Asp Glu Asp Ser Phe Ser Asn Ala Glu Ser Tyr Glu Asn Glu
    450                 455                 460

Asp Glu Glu Leu Thr Gln Pro Val Ala Arg Thr Met Asp Phe Leu Ser
465                 470                 475                 480

Pro His Gly Ser Ala Trp Asp Pro Ser Arg Glu Ala Thr Ser Leu Ala
                485                 490                 495

Gly Ser Gln Ser Tyr Glu Asp Met Arg Gly Ile Leu Tyr Ala Ala Pro
            500                 505                 510

Gln Leu Arg Ser Ile Arg Gly Gln Pro Gly Pro Asn His Glu Glu Asp
        515                 520                 525

Ala Asp Ser Tyr Glu Asn Met Asp Asn Pro Asp Gly Pro Asp Pro Ala
    530                 535                 540

Trp Gly Gly Gly Gly Arg Met Gly Thr Trp Ser Thr Arg
545                 550                 555
```

<210> SEQ ID NO 11
<211> LENGTH: 300
<212> TYPE: PRT
<213> ORGANISM: homo sapiens
<220> FEATURE:
<223> OTHER INFORMATION: CD38 antigen

<400> SEQUENCE: 11

```
Met Ala Asn Cys Glu Phe Ser Pro Val Ser Gly Asp Lys Pro Cys Cys
1               5                   10                  15

Arg Leu Ser Arg Arg Ala Gln Leu Cys Leu Gly Val Ser Ile Leu Val
            20                  25                  30

Leu Ile Leu Val Val Val Leu Ala Val Val Val Pro Arg Trp Arg Gln
        35                  40                  45

Gln Trp Ser Gly Pro Gly Thr Thr Lys Arg Phe Pro Glu Thr Val Leu
    50                  55                  60

Ala Arg Cys Val Lys Tyr Thr Glu Ile His Pro Glu Met Arg His Val
65                  70                  75                  80

Asp Cys Gln Ser Val Trp Asp Ala Phe Lys Gly Ala Phe Ile Ser Lys
                85                  90                  95

His Pro Cys Asn Ile Thr Glu Glu Asp Tyr Gln Pro Leu Met Lys Leu
            100                 105                 110

Gly Thr Gln Thr Val Pro Cys Asn Lys Ile Leu Leu Trp Ser Arg Ile
        115                 120                 125

Lys Asp Leu Ala His Gln Phe Thr Gln Val Gln Arg Asp Met Phe Thr
    130                 135                 140

Leu Glu Asp Thr Leu Leu Gly Tyr Leu Ala Asp Asp Leu Thr Trp Cys
145                 150                 155                 160

Gly Glu Phe Asn Thr Ser Lys Ile Asn Tyr Gln Ser Cys Pro Asp Trp
                165                 170                 175
```

```
Arg Lys Asp Cys Ser Asn Asn Pro Val Ser Val Phe Trp Lys Thr Val
            180                 185                 190

Ser Arg Arg Phe Ala Glu Ala Ala Cys Asp Val Val His Val Met Leu
        195                 200                 205

Asn Gly Ser Arg Ser Lys Ile Phe Asp Lys Asn Ser Thr Phe Gly Ser
    210                 215                 220

Val Glu Val His Asn Leu Gln Pro Glu Lys Val Gln Thr Leu Glu Ala
225                 230                 235                 240

Trp Val Ile His Gly Gly Arg Glu Asp Ser Arg Asp Leu Cys Gln Asp
                245                 250                 255

Pro Thr Ile Lys Glu Leu Glu Ser Ile Ile Ser Lys Arg Asn Ile Gln
            260                 265                 270

Phe Ser Cys Lys Asn Ile Tyr Arg Pro Asp Lys Phe Leu Gln Cys Val
        275                 280                 285

Lys Asn Pro Glu Asp Ser Ser Cys Thr Ser Glu Ile
    290                 295                 300


<210> SEQ ID NO 12
<211> LENGTH: 378
<212> TYPE: PRT
<213> ORGANISM: homo sapiens
<220> FEATURE:
<223> OTHER INFORMATION: CD123 antigen

<400> SEQUENCE: 12

Met Val Leu Leu Trp Leu Thr Leu Leu Leu Ile Ala Leu Pro Cys Leu
1               5                   10                  15

Leu Gln Thr Lys Glu Asp Pro Asn Pro Pro Ile Thr Asn Leu Arg Met
            20                  25                  30

Lys Ala Lys Ala Gln Gln Leu Thr Trp Asp Leu Asn Arg Asn Val Thr
        35                  40                  45

Asp Ile Glu Cys Val Lys Asp Ala Asp Tyr Ser Met Pro Ala Val Asn
    50                  55                  60

Asn Ser Tyr Cys Gln Phe Gly Ala Ile Ser Leu Cys Glu Val Thr Asn
65                  70                  75                  80

Tyr Thr Val Arg Val Ala Asn Pro Pro Phe Ser Thr Trp Ile Leu Phe
                85                  90                  95

Pro Glu Asn Ser Gly Lys Pro Trp Ala Gly Ala Glu Asn Leu Thr Cys
            100                 105                 110

Trp Ile His Asp Val Asp Phe Leu Ser Cys Ser Trp Ala Val Gly Pro
        115                 120                 125

Gly Ala Pro Ala Asp Val Gln Tyr Asp Leu Tyr Leu Asn Val Ala Asn
    130                 135                 140

Arg Arg Gln Gln Tyr Glu Cys Leu His Tyr Lys Thr Asp Ala Gln Gly
145                 150                 155                 160

Thr Arg Ile Gly Cys Arg Phe Asp Asp Ile Ser Arg Leu Ser Ser Gly
                165                 170                 175

Ser Gln Ser Ser His Ile Leu Val Arg Gly Arg Ser Ala Ala Phe Gly
            180                 185                 190

Ile Pro Cys Thr Asp Lys Phe Val Val Phe Ser Gln Ile Glu Ile Leu
        195                 200                 205

Thr Pro Pro Asn Met Thr Ala Lys Cys Asn Lys Thr His Ser Phe Met
    210                 215                 220

His Trp Lys Met Arg Ser His Phe Asn Arg Lys Phe Arg Tyr Glu Leu
225                 230                 235                 240
```

```
Gln Ile Gln Lys Arg Met Gln Pro Val Ile Thr Glu Gln Val Arg Asp
                245                 250                 255

Arg Thr Ser Phe Gln Leu Leu Asn Pro Gly Thr Tyr Thr Val Gln Ile
            260                 265                 270

Arg Ala Arg Glu Arg Val Tyr Glu Phe Leu Ser Ala Trp Ser Thr Pro
        275                 280                 285

Gln Arg Phe Glu Cys Asp Gln Glu Glu Gly Ala Asn Thr Arg Ala Trp
    290                 295                 300

Arg Thr Ser Leu Leu Ile Ala Leu Gly Thr Leu Leu Ala Leu Val Cys
305                 310                 315                 320

Val Phe Val Ile Cys Arg Arg Tyr Leu Val Met Gln Arg Leu Phe Pro
                325                 330                 335

Arg Ile Pro His Met Lys Asp Pro Ile Gly Asp Ser Phe Gln Asn Asp
            340                 345                 350

Lys Leu Val Val Trp Glu Ala Gly Lys Ala Gly Leu Glu Glu Cys Leu
        355                 360                 365

Val Thr Glu Val Gln Val Val Gln Lys Thr
    370                 375


<210> SEQ ID NO 13
<211> LENGTH: 335
<212> TYPE: PRT
<213> ORGANISM: homo sapiens
<220> FEATURE:
<223> OTHER INFORMATION: CS1 antigen

<400> SEQUENCE: 13

Met Ala Gly Ser Pro Thr Cys Leu Thr Leu Ile Tyr Ile Leu Trp Gln
1               5                   10                  15

Leu Thr Gly Ser Ala Ala Ser Gly Pro Val Lys Glu Leu Val Gly Ser
            20                  25                  30

Val Gly Gly Ala Val Thr Phe Pro Leu Lys Ser Lys Val Lys Gln Val
        35                  40                  45

Asp Ser Ile Val Trp Thr Phe Asn Thr Thr Pro Leu Val Thr Ile Gln
    50                  55                  60

Pro Glu Gly Gly Thr Ile Ile Val Thr Gln Asn Arg Asn Arg Glu Arg
65                  70                  75                  80

Val Asp Phe Pro Asp Gly Gly Tyr Ser Leu Lys Leu Ser Lys Leu Lys
                85                  90                  95

Lys Asn Asp Ser Gly Ile Tyr Tyr Val Gly Ile Tyr Ser Ser Ser Leu
            100                 105                 110

Gln Gln Pro Ser Thr Gln Glu Tyr Val Leu His Val Tyr Glu His Leu
        115                 120                 125

Ser Lys Pro Lys Val Thr Met Gly Leu Gln Ser Asn Lys Asn Gly Thr
    130                 135                 140

Cys Val Thr Asn Leu Thr Cys Cys Met Glu His Gly Glu Glu Asp Val
145                 150                 155                 160

Ile Tyr Thr Trp Lys Ala Leu Gly Gln Ala Ala Asn Glu Ser His Asn
                165                 170                 175

Gly Ser Ile Leu Pro Ile Ser Trp Arg Trp Gly Glu Ser Asp Met Thr
            180                 185                 190

Phe Ile Cys Val Ala Arg Asn Pro Val Ser Arg Asn Phe Ser Ser Pro
        195                 200                 205

Ile Leu Ala Arg Lys Leu Cys Glu Gly Ala Ala Asp Asp Pro Asp Ser
    210                 215                 220
```

```
Ser Met Val Leu Leu Cys Leu Leu Leu Val Pro Leu Leu Leu Ser Leu
225                 230                 235                 240

Phe Val Leu Gly Leu Phe Leu Trp Phe Leu Lys Arg Glu Arg Gln Glu
                245                 250                 255

Glu Tyr Ile Glu Glu Lys Lys Arg Val Asp Ile Cys Arg Glu Thr Pro
            260                 265                 270

Asn Ile Cys Pro His Ser Gly Glu Asn Thr Glu Tyr Asp Thr Ile Pro
        275                 280                 285

His Thr Asn Arg Thr Ile Leu Lys Glu Asp Pro Ala Asn Thr Val Tyr
    290                 295                 300

Ser Thr Val Glu Ile Pro Lys Lys Met Glu Asn Pro His Ser Leu Leu
305                 310                 315                 320

Thr Met Pro Asp Thr Pro Arg Leu Phe Ala Tyr Glu Asn Val Ile
                325                 330                 335


<210> SEQ ID NO 14
<211> LENGTH: 184
<212> TYPE: PRT
<213> ORGANISM: homo sapiens
<220> FEATURE:
<223> OTHER INFORMATION: BCMA antigen

<400> SEQUENCE: 14

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Ile Leu Trp Thr Cys Leu Gly Leu Ser Leu
    50                  55                  60

Ile Ile Ser Leu Ala Val Phe Val Leu Met Phe Leu Leu Arg Lys Ile
65                  70                  75                  80

Asn Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125

Glu Asp Cys Ile Lys Ser Lys Pro Lys Val Asp Ser Asp His Cys Phe
    130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180


<210> SEQ ID NO 15
<211> LENGTH: 993
<212> TYPE: PRT
<213> ORGANISM: homo sapiens
<220> FEATURE:
<223> OTHER INFORMATION: FLT3 antigen

<400> SEQUENCE: 15

Met Pro Ala Leu Ala Arg Asp Gly Gly Gln Leu Pro Leu Leu Val Val
1               5                   10                  15
```

```
Phe Ser Ala Met Ile Phe Gly Thr Ile Thr Asn Gln Asp Leu Pro Val
            20                  25                  30

Ile Lys Cys Val Leu Ile Asn His Lys Asn Asn Asp Ser Ser Val Gly
        35                  40                  45

Lys Ser Ser Ser Tyr Pro Met Val Ser Glu Ser Pro Glu Asp Leu Gly
    50                  55                  60

Cys Ala Leu Arg Pro Gln Ser Ser Gly Thr Val Tyr Glu Ala Ala Ala
65                  70                  75                  80

Val Glu Val Asp Val Ser Ala Ser Ile Thr Leu Gln Val Leu Val Asp
                85                  90                  95

Ala Pro Gly Asn Ile Ser Cys Leu Trp Val Phe Lys His Ser Ser Leu
            100                 105                 110

Asn Cys Gln Pro His Phe Asp Leu Gln Asn Arg Gly Val Val Ser Met
        115                 120                 125

Val Ile Leu Lys Met Thr Glu Thr Gln Ala Gly Glu Tyr Leu Leu Phe
    130                 135                 140

Ile Gln Ser Glu Ala Thr Asn Tyr Thr Ile Leu Phe Thr Val Ser Ile
145                 150                 155                 160

Arg Asn Thr Leu Leu Tyr Thr Leu Arg Arg Pro Tyr Phe Arg Lys Met
                165                 170                 175

Glu Asn Gln Asp Ala Leu Val Cys Ile Ser Glu Ser Val Pro Glu Pro
            180                 185                 190

Ile Val Glu Trp Val Leu Cys Asp Ser Gln Gly Glu Ser Cys Lys Glu
        195                 200                 205

Glu Ser Pro Ala Val Val Lys Lys Glu Glu Lys Val Leu His Glu Leu
    210                 215                 220

Phe Gly Thr Asp Ile Arg Cys Cys Ala Arg Asn Glu Leu Gly Arg Glu
225                 230                 235                 240

Cys Thr Arg Leu Phe Thr Ile Asp Leu Asn Gln Thr Pro Gln Thr Thr
                245                 250                 255

Leu Pro Gln Leu Phe Leu Lys Val Gly Glu Pro Leu Trp Ile Arg Cys
            260                 265                 270

Lys Ala Val His Val Asn His Gly Phe Gly Leu Thr Trp Glu Leu Glu
        275                 280                 285

Asn Lys Ala Leu Glu Glu Gly Asn Tyr Phe Glu Met Ser Thr Tyr Ser
    290                 295                 300

Thr Asn Arg Thr Met Ile Arg Ile Leu Phe Ala Phe Val Ser Ser Val
305                 310                 315                 320

Ala Arg Asn Asp Thr Gly Tyr Tyr Thr Cys Ser Ser Ser Lys His Pro
                325                 330                 335

Ser Gln Ser Ala Leu Val Thr Ile Val Glu Lys Gly Phe Ile Asn Ala
            340                 345                 350

Thr Asn Ser Ser Glu Asp Tyr Glu Ile Asp Gln Tyr Glu Glu Phe Cys
        355                 360                 365

Phe Ser Val Arg Phe Lys Ala Tyr Pro Gln Ile Arg Cys Thr Trp Thr
    370                 375                 380

Phe Ser Arg Lys Ser Phe Pro Cys Glu Gln Lys Gly Leu Asp Asn Gly
385                 390                 395                 400

Tyr Ser Ile Ser Lys Phe Cys Asn His Lys His Gln Pro Gly Glu Tyr
                405                 410                 415

Ile Phe His Ala Glu Asn Asp Asp Ala Gln Phe Thr Lys Met Phe Thr
            420                 425                 430
```

```
Leu Asn Ile Arg Arg Lys Pro Gln Val Leu Ala Glu Ala Ser Ala Ser
        435                 440                 445

Gln Ala Ser Cys Phe Ser Asp Gly Tyr Pro Leu Pro Ser Trp Thr Trp
    450                 455                 460

Lys Lys Cys Ser Asp Lys Ser Pro Asn Cys Thr Glu Glu Ile Thr Glu
465                 470                 475                 480

Gly Val Trp Asn Arg Lys Ala Asn Arg Lys Val Phe Gly Gln Trp Val
                485                 490                 495

Ser Ser Ser Thr Leu Asn Met Ser Glu Ala Ile Lys Gly Phe Leu Val
            500                 505                 510

Lys Cys Cys Ala Tyr Asn Ser Leu Gly Thr Ser Cys Glu Thr Ile Leu
        515                 520                 525

Leu Asn Ser Pro Gly Pro Phe Pro Phe Ile Gln Asp Asn Ile Ser Phe
    530                 535                 540

Tyr Ala Thr Ile Gly Val Cys Leu Leu Phe Ile Val Val Leu Thr Leu
545                 550                 555                 560

Leu Ile Cys His Lys Tyr Lys Lys Gln Phe Arg Tyr Glu Ser Gln Leu
                565                 570                 575

Gln Met Val Gln Val Thr Gly Ser Ser Asp Asn Glu Tyr Phe Tyr Val
            580                 585                 590

Asp Phe Arg Glu Tyr Glu Tyr Asp Leu Lys Trp Glu Phe Pro Arg Glu
        595                 600                 605

Asn Leu Glu Phe Gly Lys Val Leu Gly Ser Gly Ala Phe Gly Lys Val
    610                 615                 620

Met Asn Ala Thr Ala Tyr Gly Ile Ser Lys Thr Gly Val Ser Ile Gln
625                 630                 635                 640

Val Ala Val Lys Met Leu Lys Glu Lys Ala Asp Ser Ser Glu Arg Glu
                645                 650                 655

Ala Leu Met Ser Glu Leu Lys Met Met Thr Gln Leu Gly Ser His Glu
            660                 665                 670

Asn Ile Val Asn Leu Leu Gly Ala Cys Thr Leu Ser Gly Pro Ile Tyr
        675                 680                 685

Leu Ile Phe Glu Tyr Cys Cys Tyr Gly Asp Leu Leu Asn Tyr Leu Arg
    690                 695                 700

Ser Lys Arg Glu Lys Phe His Arg Thr Trp Thr Glu Ile Phe Lys Glu
705                 710                 715                 720

His Asn Phe Ser Phe Tyr Pro Thr Phe Gln Ser His Pro Asn Ser Ser
                725                 730                 735

Met Pro Gly Ser Arg Glu Val Gln Ile His Pro Asp Ser Asp Gln Ile
            740                 745                 750

Ser Gly Leu His Gly Asn Ser Phe His Ser Glu Asp Glu Ile Glu Tyr
        755                 760                 765

Glu Asn Gln Lys Arg Leu Glu Glu Glu Glu Asp Leu Asn Val Leu Thr
    770                 775                 780

Phe Glu Asp Leu Leu Cys Phe Ala Tyr Gln Val Ala Lys Gly Met Glu
785                 790                 795                 800

Phe Leu Glu Phe Lys Ser Cys Val His Arg Asp Leu Ala Ala Arg Asn
                805                 810                 815

Val Leu Val Thr His Gly Lys Val Val Lys Ile Cys Asp Phe Gly Leu
            820                 825                 830

Ala Arg Asp Ile Met Ser Asp Ser Asn Tyr Val Val Arg Gly Asn Ala
        835                 840                 845

Arg Leu Pro Val Lys Trp Met Ala Pro Glu Ser Leu Phe Glu Gly Ile
```

```
    850                 855                 860

Tyr Thr Ile Lys Ser Asp Val Trp Ser Tyr Gly Ile Leu Leu Trp Glu
865                 870                 875                 880

Ile Phe Ser Leu Gly Val Asn Pro Tyr Pro Gly Ile Pro Val Asp Ala
                885                 890                 895

Asn Phe Tyr Lys Leu Ile Gln Asn Gly Phe Lys Met Asp Gln Pro Phe
            900                 905                 910

Tyr Ala Thr Glu Glu Ile Tyr Ile Ile Met Gln Ser Cys Trp Ala Phe
        915                 920                 925

Asp Ser Arg Lys Arg Pro Ser Phe Pro Asn Leu Thr Ser Phe Leu Gly
    930                 935                 940

Cys Gln Leu Ala Asp Ala Glu Glu Ala Met Tyr Gln Asn Val Asp Gly
945                 950                 955                 960

Arg Val Ser Glu Cys Pro His Thr Tyr Gln Asn Arg Arg Pro Phe Ser
                965                 970                 975

Arg Glu Met Asp Leu Gly Leu Leu Ser Pro Gln Ala Gln Val Glu Asp
            980                 985                 990

Ser


<210> SEQ ID NO 16
<211> LENGTH: 364
<212> TYPE: PRT
<213> ORGANISM: homo sapiens
<220> FEATURE:
<223> OTHER INFORMATION: CD33 antigen

<400> SEQUENCE: 16

Met Pro Leu Leu Leu Leu Leu Pro Leu Leu Trp Ala Gly Ala Leu Ala
1               5                   10                  15

Met Asp Pro Asn Phe Trp Leu Gln Val Gln Glu Ser Val Thr Val Gln
            20                  25                  30

Glu Gly Leu Cys Val Leu Val Pro Cys Thr Phe Phe His Pro Ile Pro
        35                  40                  45

Tyr Tyr Asp Lys Asn Ser Pro Val His Gly Tyr Trp Phe Arg Glu Gly
    50                  55                  60

Ala Ile Ile Ser Arg Asp Ser Pro Val Ala Thr Asn Lys Leu Asp Gln
65                  70                  75                  80

Glu Val Gln Glu Glu Thr Gln Gly Arg Phe Arg Leu Leu Gly Asp Pro
                85                  90                  95

Ser Arg Asn Asn Cys Ser Leu Ser Ile Val Asp Ala Arg Arg Arg Asp
            100                 105                 110

Asn Gly Ser Tyr Phe Phe Arg Met Glu Arg Gly Ser Thr Lys Tyr Ser
        115                 120                 125

Tyr Lys Ser Pro Gln Leu Ser Val His Val Thr Asp Leu Thr His Arg
    130                 135                 140

Pro Lys Ile Leu Ile Pro Gly Thr Leu Glu Pro Gly His Ser Lys Asn
145                 150                 155                 160

Leu Thr Cys Ser Val Ser Trp Ala Cys Glu Gln Gly Thr Pro Pro Ile
                165                 170                 175

Phe Ser Trp Leu Ser Ala Ala Pro Thr Ser Leu Gly Pro Arg Thr Thr
            180                 185                 190

His Ser Ser Val Leu Ile Ile Thr Pro Arg Pro Gln Asp His Gly Thr
        195                 200                 205

Asn Leu Thr Cys Gln Val Lys Phe Ala Gly Ala Gly Val Thr Thr Glu
    210                 215                 220
```

```
Arg Thr Ile Gln Leu Asn Val Thr Tyr Val Pro Gln Asn Pro Thr Thr
225                 230                 235                 240

Gly Ile Phe Pro Gly Asp Gly Ser Gly Lys Gln Glu Thr Arg Ala Gly
                245                 250                 255

Val Val His Gly Ala Ile Gly Gly Ala Gly Val Thr Ala Leu Leu Ala
            260                 265                 270

Leu Cys Leu Cys Leu Ile Phe Phe Ile Val Lys Thr His Arg Arg Lys
        275                 280                 285

Ala Ala Arg Thr Ala Val Gly Arg Asn Asp Thr His Pro Thr Thr Gly
    290                 295                 300

Ser Ala Ser Pro Lys His Gln Lys Lys Ser Lys Leu His Gly Pro Thr
305                 310                 315                 320

Glu Thr Ser Ser Cys Ser Gly Ala Ala Pro Thr Val Glu Met Asp Glu
                325                 330                 335

Glu Leu His Tyr Ala Ser Leu Asn Phe His Gly Met Asn Pro Ser Lys
            340                 345                 350

Asp Thr Ser Thr Glu Tyr Ser Glu Val Arg Thr Gln
        355                 360


<210> SEQ ID NO 17
<211> LENGTH: 193
<212> TYPE: PRT
<213> ORGANISM: homo sapiens
<220> FEATURE:
<223> OTHER INFORMATION: CD70 antigen

<400> SEQUENCE: 17

Met Pro Glu Glu Gly Ser Gly Cys Ser Val Arg Arg Arg Pro Tyr Gly
1               5                   10                  15

Cys Val Leu Arg Ala Ala Leu Val Pro Leu Val Ala Gly Leu Val Ile
            20                  25                  30

Cys Leu Val Val Cys Ile Gln Arg Phe Ala Gln Ala Gln Gln Gln Leu
        35                  40                  45

Pro Leu Glu Ser Leu Gly Trp Asp Val Ala Glu Leu Gln Leu Asn His
    50                  55                  60

Thr Gly Pro Gln Gln Asp Pro Arg Leu Tyr Trp Gln Gly Gly Pro Ala
65                  70                  75                  80

Leu Gly Arg Ser Phe Leu His Gly Pro Glu Leu Asp Lys Gly Gln Leu
                85                  90                  95

Arg Ile His Arg Asp Gly Ile Tyr Met Val His Ile Gln Val Thr Leu
            100                 105                 110

Ala Ile Cys Ser Ser Thr Thr Ala Ser Arg His His Pro Thr Thr Leu
        115                 120                 125

Ala Val Gly Ile Cys Ser Pro Ala Ser Arg Ser Ile Ser Leu Leu Arg
    130                 135                 140

Leu Ser Phe His Gln Gly Cys Thr Ile Ala Ser Gln Arg Leu Thr Pro
145                 150                 155                 160

Leu Ala Arg Gly Asp Thr Leu Cys Thr Asn Leu Thr Gly Thr Leu Leu
                165                 170                 175

Pro Ser Arg Asn Thr Asp Glu Thr Phe Phe Gly Val Gln Trp Val Arg
            180                 185                 190

Pro


<210> SEQ ID NO 18
<211> LENGTH: 943
```

<212> TYPE: PRT
<213> ORGANISM: homo sapiens
<220> FEATURE:
<223> OTHER INFORMATION: EGFRvIII

<400> SEQUENCE: 18

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Gly Asn Tyr
            20                  25                  30

Val Val Thr Asp His Gly Ser Cys Val Arg Ala Cys Gly Ala Asp Ser
        35                  40                  45

Tyr Glu Met Glu Glu Asp Gly Val Arg Lys Cys Lys Lys Cys Glu Gly
    50                  55                  60

Pro Cys Arg Lys Val Cys Asn Gly Ile Gly Ile Gly Glu Phe Lys Asp
65                  70                  75                  80

Ser Leu Ser Ile Asn Ala Thr Asn Ile Lys His Phe Lys Asn Cys Thr
                85                  90                  95

Ser Ile Ser Gly Asp Leu His Ile Leu Pro Val Ala Phe Arg Gly Asp
            100                 105                 110

Ser Phe Thr His Thr Pro Pro Leu Asp Pro Gln Glu Leu Asp Ile Leu
        115                 120                 125

Lys Thr Val Lys Glu Ile Thr Gly Phe Leu Leu Ile Gln Ala Trp Pro
    130                 135                 140

Glu Asn Arg Thr Asp Leu His Ala Phe Glu Asn Leu Glu Ile Ile Arg
145                 150                 155                 160

Gly Arg Thr Lys Gln His Gly Gln Phe Ser Leu Ala Val Val Ser Leu
                165                 170                 175

Asn Ile Thr Ser Leu Gly Leu Arg Ser Leu Lys Glu Ile Ser Asp Gly
            180                 185                 190

Asp Val Ile Ile Ser Gly Asn Lys Asn Leu Cys Tyr Ala Asn Thr Ile
        195                 200                 205

Asn Trp Lys Lys Leu Phe Gly Thr Ser Gly Gln Lys Thr Lys Ile Ile
    210                 215                 220

Ser Asn Arg Gly Glu Asn Ser Cys Lys Ala Thr Gly Gln Val Cys His
225                 230                 235                 240

Ala Leu Cys Ser Pro Glu Gly Cys Trp Gly Pro Glu Pro Arg Asp Cys
                245                 250                 255

Val Ser Cys Arg Asn Val Ser Arg Gly Arg Glu Cys Val Asp Lys Cys
            260                 265                 270

Asn Leu Leu Glu Gly Glu Pro Arg Glu Phe Val Glu Asn Ser Glu Cys
        275                 280                 285

Ile Gln Cys His Pro Glu Cys Leu Pro Gln Ala Met Asn Ile Thr Cys
    290                 295                 300

Thr Gly Arg Gly Pro Asp Asn Cys Ile Gln Cys Ala His Tyr Ile Asp
305                 310                 315                 320

Gly Pro His Cys Val Lys Thr Cys Pro Ala Gly Val Met Gly Glu Asn
                325                 330                 335

Asn Thr Leu Val Trp Lys Tyr Ala Asp Ala Gly His Val Cys His Leu
            340                 345                 350

Cys His Pro Asn Cys Thr Tyr Gly Cys Thr Gly Pro Gly Leu Glu Gly
        355                 360                 365

Cys Pro Thr Asn Gly Pro Lys Ile Pro Ser Ile Ala Thr Gly Met Val
    370                 375                 380
```

```
Gly Ala Leu Leu Leu Leu Leu Val Val Ala Leu Gly Ile Gly Leu Phe
385                 390                 395                 400

Met Arg Arg Arg His Ile Val Arg Lys Arg Thr Leu Arg Arg Leu Leu
                405                 410                 415

Gln Glu Arg Glu Leu Val Glu Pro Leu Thr Pro Ser Gly Glu Ala Pro
            420                 425                 430

Asn Gln Ala Leu Leu Arg Ile Leu Lys Glu Thr Glu Phe Lys Lys Ile
        435                 440                 445

Lys Val Leu Gly Ser Gly Ala Phe Gly Thr Val Tyr Lys Gly Leu Trp
    450                 455                 460

Ile Pro Glu Gly Glu Lys Val Lys Ile Pro Val Ala Ile Lys Glu Leu
465                 470                 475                 480

Arg Glu Ala Thr Ser Pro Lys Ala Asn Lys Glu Ile Leu Asp Glu Ala
                485                 490                 495

Tyr Val Met Ala Ser Val Asp Asn Pro His Val Cys Arg Leu Leu Gly
            500                 505                 510

Ile Cys Leu Thr Ser Thr Val Gln Leu Ile Thr Gln Leu Met Pro Phe
        515                 520                 525

Gly Cys Leu Leu Asp Tyr Val Arg Glu His Lys Asp Asn Ile Gly Ser
    530                 535                 540

Gln Tyr Leu Leu Asn Trp Cys Val Gln Ile Ala Lys Gly Met Asn Tyr
545                 550                 555                 560

Leu Glu Asp Arg Arg Leu Val His Arg Asp Leu Ala Ala Arg Asn Val
                565                 570                 575

Leu Val Lys Thr Pro Gln His Val Lys Ile Thr Asp Phe Gly Leu Ala
            580                 585                 590

Lys Leu Leu Gly Ala Glu Glu Lys Glu Tyr His Ala Glu Gly Gly Lys
        595                 600                 605

Val Pro Ile Lys Trp Met Ala Leu Glu Ser Ile Leu His Arg Ile Tyr
    610                 615                 620

Thr His Gln Ser Asp Val Trp Ser Tyr Gly Val Thr Val Trp Glu Leu
625                 630                 635                 640

Met Thr Phe Gly Ser Lys Pro Tyr Asp Gly Ile Pro Ala Ser Glu Ile
                645                 650                 655

Ser Ser Ile Leu Glu Lys Gly Glu Arg Leu Pro Gln Pro Pro Ile Cys
            660                 665                 670

Thr Ile Asp Val Tyr Met Ile Met Val Lys Cys Trp Met Ile Asp Ala
        675                 680                 685

Asp Ser Arg Pro Lys Phe Arg Glu Leu Ile Ile Glu Phe Ser Lys Met
    690                 695                 700

Ala Arg Asp Pro Gln Arg Tyr Leu Val Ile Gln Gly Asp Glu Arg Met
705                 710                 715                 720

His Leu Pro Ser Pro Thr Asp Ser Asn Phe Tyr Arg Ala Leu Met Asp
                725                 730                 735

Glu Glu Asp Met Asp Asp Val Val Asp Ala Asp Glu Tyr Leu Ile Pro
            740                 745                 750

Gln Gln Gly Phe Phe Ser Ser Pro Ser Thr Ser Arg Thr Pro Leu Leu
        755                 760                 765

Ser Ser Leu Ser Ala Thr Ser Asn Asn Ser Thr Val Ala Cys Ile Asp
    770                 775                 780

Arg Asn Gly Leu Gln Ser Cys Pro Ile Lys Glu Asp Ser Phe Leu Gln
785                 790                 795                 800

Arg Tyr Ser Ser Asp Pro Thr Gly Ala Leu Thr Glu Asp Ser Ile Asp
```

805 810 815

Asp Thr Phe Leu Pro Val Pro Glu Tyr Ile Asn Gln Ser Val Pro Lys
820 825 830

Arg Pro Ala Gly Ser Val Gln Asn Pro Val Tyr His Asn Gln Pro Leu
835 840 845

Asn Pro Ala Pro Ser Arg Asp Pro His Tyr Gln Asp Pro His Ser Thr
850 855 860

Ala Val Gly Asn Pro Glu Tyr Leu Asn Thr Val Gln Pro Thr Cys Val
865 870 875 880

Asn Ser Thr Phe Asp Ser Pro Ala His Trp Ala Gln Lys Gly Ser His
885 890 895

Gln Ile Ser Leu Asp Asn Pro Asp Tyr Gln Gln Asp Phe Phe Pro Lys
900 905 910

Glu Ala Lys Pro Asn Gly Ile Phe Lys Gly Ser Thr Ala Glu Asn Ala
915 920 925

Glu Tyr Leu Arg Val Ala Pro Gln Ser Ser Glu Phe Ile Gly Ala
930 935 940

<210> SEQ ID NO 19
<211> LENGTH: 497
<212> TYPE: PRT
<213> ORGANISM: homo sapiens
<220> FEATURE:
<223> OTHER INFORMATION: WT1

<400> SEQUENCE: 19

Met Gln Asp Pro Ala Ser Thr Cys Val Pro Glu Pro Ala Ser Gln His
1 5 10 15

Thr Leu Arg Ser Gly Pro Gly Cys Leu Gln Gln Pro Glu Gln Gln Gly
20 25 30

Val Arg Asp Pro Gly Gly Ile Trp Ala Lys Leu Gly Ala Ala Glu Ala
35 40 45

Ser Ala Glu Arg Leu Gln Gly Arg Arg Ser Arg Gly Ala Ser Gly Ser
50 55 60

Glu Pro Gln Gln Met Gly Ser Asp Val Arg Asp Leu Asn Ala Leu Leu
65 70 75 80

Pro Ala Val Pro Ser Leu Gly Gly Gly Gly Gly Cys Ala Leu Pro Val
85 90 95

Ser Gly Ala Ala Gln Trp Ala Pro Val Leu Asp Phe Ala Pro Pro Gly
100 105 110

Ala Ser Ala Tyr Gly Ser Leu Gly Gly Pro Ala Pro Pro Pro Ala Pro
115 120 125

Pro Pro Pro Pro Pro Pro Pro Pro His Ser Phe Ile Lys Gln Glu Pro
130 135 140

Ser Trp Gly Gly Ala Glu Pro His Glu Glu Gln Cys Leu Ser Ala Phe
145 150 155 160

Thr Val His Phe Ser Gly Gln Phe Thr Gly Thr Ala Gly Ala Cys Arg
165 170 175

Tyr Gly Pro Phe Gly Pro Pro Pro Pro Ser Gln Ala Ser Ser Gly Gln
180 185 190

Ala Arg Met Phe Pro Asn Ala Pro Tyr Leu Pro Ser Cys Leu Glu Ser
195 200 205

Gln Pro Ala Ile Arg Asn Gln Gly Tyr Ser Thr Val Thr Phe Asp Gly
210 215 220

Thr Pro Ser Tyr Gly His Thr Pro Ser His His Ala Ala Gln Phe Pro

```
225                 230                 235                 240

Asn His Ser Phe Lys His Glu Asp Pro Met Gly Gln Gln Gly Ser Leu
                245                 250                 255

Gly Glu Gln Gln Tyr Ser Val Pro Pro Pro Val Tyr Gly Cys His Thr
            260                 265                 270

Pro Thr Asp Ser Cys Thr Gly Ser Gln Ala Leu Leu Leu Arg Thr Pro
        275                 280                 285

Tyr Ser Ser Asp Asn Leu Tyr Gln Met Thr Ser Gln Leu Glu Cys Met
    290                 295                 300

Thr Trp Asn Gln Met Asn Leu Gly Ala Thr Leu Lys Gly His Ser Thr
305                 310                 315                 320

Gly Tyr Glu Ser Asp Asn His Thr Thr Pro Ile Leu Cys Gly Ala Gln
                325                 330                 335

Tyr Arg Ile His Thr His Gly Val Phe Arg Gly Ile Gln Asp Val Arg
            340                 345                 350

Arg Val Pro Gly Val Ala Pro Thr Leu Val Arg Ser Ala Ser Glu Thr
        355                 360                 365

Ser Glu Lys Arg Pro Phe Met Cys Ala Tyr Pro Gly Cys Asn Lys Arg
    370                 375                 380

Tyr Phe Lys Leu Ser His Leu Gln Met His Ser Arg Lys His Thr Gly
385                 390                 395                 400

Glu Lys Pro Tyr Gln Cys Asp Phe Lys Asp Cys Glu Arg Arg Phe Ser
                405                 410                 415

Arg Ser Asp Gln Leu Lys Arg His Gln Arg Arg His Thr Gly Val Lys
            420                 425                 430

Pro Phe Gln Cys Lys Thr Cys Gln Arg Lys Phe Ser Arg Ser Asp His
        435                 440                 445

Leu Lys Thr His Thr Arg Thr His Thr Gly Glu Lys Pro Phe Ser Cys
    450                 455                 460

Arg Trp Pro Ser Cys Gln Lys Lys Phe Ala Arg Ser Asp Glu Leu Val
465                 470                 475                 480

Arg His His Asn Met His Gln Arg Asn Met Thr Lys Leu Gln Leu Ala
                485                 490                 495

Leu


<210> SEQ ID NO 20
<211> LENGTH: 58
<212> TYPE: DNA
<213> ORGANISM: homo sapiens
<220> FEATURE:
<223> OTHER INFORMATION: Beta2M target 1

<400> SEQUENCE: 20

tctcgctccg tggccttagc tgtgctcgcg ctactctctc tttctggcct ggaggcta       58


<210> SEQ ID NO 21
<211> LENGTH: 936
<212> TYPE: PRT
<213> ORGANISM: artificial sequence
<220> FEATURE:
<223> OTHER INFORMATION: Left Talen for beta2M target 1

<400> SEQUENCE: 21

Met Gly Asp Pro Lys Lys Lys Arg Lys Val Ile Asp Tyr Pro Tyr Asp
1               5                   10                  15

Val Pro Asp Tyr Ala Ile Asp Ile Ala Asp Leu Arg Thr Leu Gly Tyr
            20                  25                  30
```

```
Ser Gln Gln Gln Gln Glu Lys Ile Lys Pro Lys Val Arg Ser Thr Val
        35                  40                  45

Ala Gln His His Glu Ala Leu Val Gly His Gly Phe Thr His Ala His
    50                  55                  60

Ile Val Ala Leu Ser Gln His Pro Ala Ala Leu Gly Thr Val Ala Val
65                  70                  75                  80

Lys Tyr Gln Asp Met Ile Ala Ala Leu Pro Glu Ala Thr His Glu Ala
                85                  90                  95

Ile Val Gly Val Gly Lys Gln Trp Ser Gly Ala Arg Ala Leu Glu Ala
            100                 105                 110

Leu Leu Thr Val Ala Gly Glu Leu Arg Gly Pro Pro Leu Gln Leu Asp
        115                 120                 125

Thr Gly Gln Leu Leu Lys Ile Ala Lys Arg Gly Gly Val Thr Ala Val
    130                 135                 140

Glu Ala Val His Ala Trp Arg Asn Ala Leu Thr Gly Ala Pro Leu Asn
145                 150                 155                 160

Leu Thr Pro Gln Gln Val Val Ala Ile Ala Ser Asn Asn Gly Gly Lys
                165                 170                 175

Gln Ala Leu Glu Thr Val Gln Arg Leu Leu Pro Val Leu Cys Gln Ala
            180                 185                 190

His Gly Leu Thr Pro Gln Gln Val Val Ala Ile Ala Ser Asn Asn Gly
        195                 200                 205

Gly Lys Gln Ala Leu Glu Thr Val Gln Arg Leu Leu Pro Val Leu Cys
    210                 215                 220

Gln Ala His Gly Leu Thr Pro Glu Gln Val Val Ala Ile Ala Ser His
225                 230                 235                 240

Asp Gly Gly Lys Gln Ala Leu Glu Thr Val Gln Arg Leu Leu Pro Val
                245                 250                 255

Leu Cys Gln Ala His Gly Leu Thr Pro Glu Gln Val Val Ala Ile Ala
            260                 265                 270

Ser His Asp Gly Gly Lys Gln Ala Leu Glu Thr Val Gln Arg Leu Leu
        275                 280                 285

Pro Val Leu Cys Gln Ala His Gly Leu Thr Pro Gln Gln Val Val Ala
    290                 295                 300

Ile Ala Ser Asn Gly Gly Gly Lys Gln Ala Leu Glu Thr Val Gln Arg
305                 310                 315                 320

Leu Leu Pro Val Leu Cys Gln Ala His Gly Leu Thr Pro Gln Gln Val
                325                 330                 335

Val Ala Ile Ala Ser Asn Gly Gly Gly Lys Gln Ala Leu Glu Thr Val
            340                 345                 350

Gln Arg Leu Leu Pro Val Leu Cys Gln Ala His Gly Leu Thr Pro Glu
        355                 360                 365

Gln Val Val Ala Ile Ala Ser Asn Ile Gly Gly Lys Gln Ala Leu Glu
    370                 375                 380

Thr Val Gln Ala Leu Leu Pro Val Leu Cys Gln Ala His Gly Leu Thr
385                 390                 395                 400

Pro Gln Gln Val Val Ala Ile Ala Ser Asn Asn Gly Gly Lys Gln Ala
                405                 410                 415

Leu Glu Thr Val Gln Arg Leu Leu Pro Val Leu Cys Gln Ala His Gly
            420                 425                 430

Leu Thr Pro Glu Gln Val Val Ala Ile Ala Ser His Asp Gly Gly Lys
        435                 440                 445
```

```
Gln Ala Leu Glu Thr Val Gln Arg Leu Leu Pro Val Leu Cys Gln Ala
    450                 455                 460

His Gly Leu Thr Pro Gln Gln Val Val Ala Ile Ala Ser Asn Gly Gly
465                 470                 475                 480

Gly Lys Gln Ala Leu Glu Thr Val Gln Arg Leu Leu Pro Val Leu Cys
                485                 490                 495

Gln Ala His Gly Leu Thr Pro Gln Gln Val Val Ala Ile Ala Ser Asn
            500                 505                 510

Asn Gly Gly Lys Gln Ala Leu Glu Thr Val Gln Arg Leu Leu Pro Val
        515                 520                 525

Leu Cys Gln Ala His Gly Leu Thr Pro Gln Gln Val Val Ala Ile Ala
    530                 535                 540

Ser Asn Gly Gly Gly Lys Gln Ala Leu Glu Thr Val Gln Arg Leu Leu
545                 550                 555                 560

Pro Val Leu Cys Gln Ala His Gly Leu Thr Pro Gln Gln Val Val Ala
                565                 570                 575

Ile Ala Ser Asn Asn Gly Gly Lys Gln Ala Leu Glu Thr Val Gln Arg
            580                 585                 590

Leu Leu Pro Val Leu Cys Gln Ala His Gly Leu Thr Pro Glu Gln Val
        595                 600                 605

Val Ala Ile Ala Ser His Asp Gly Gly Lys Gln Ala Leu Glu Thr Val
    610                 615                 620

Gln Arg Leu Leu Pro Val Leu Cys Gln Ala His Gly Leu Thr Pro Gln
625                 630                 635                 640

Gln Val Val Ala Ile Ala Ser Asn Gly Gly Gly Lys Gln Ala Leu Glu
                645                 650                 655

Thr Val Gln Arg Leu Leu Pro Val Leu Cys Gln Ala His Gly Leu Thr
            660                 665                 670

Pro Gln Gln Val Val Ala Ile Ala Ser Asn Gly Gly Gly Arg Pro Ala
        675                 680                 685

Leu Glu Ser Ile Val Ala Gln Leu Ser Arg Pro Asp Pro Ala Leu Ala
    690                 695                 700

Ala Leu Thr Asn Asp His Leu Val Ala Leu Ala Cys Leu Gly Gly Arg
705                 710                 715                 720

Pro Ala Leu Asp Ala Val Lys Lys Gly Leu Gly Asp Pro Ile Ser Arg
                725                 730                 735

Ser Gln Leu Val Lys Ser Glu Leu Glu Glu Lys Lys Ser Glu Leu Arg
            740                 745                 750

His Lys Leu Lys Tyr Val Pro His Glu Tyr Ile Glu Leu Ile Glu Ile
        755                 760                 765

Ala Arg Asn Ser Thr Gln Asp Arg Ile Leu Glu Met Lys Val Met Glu
    770                 775                 780

Phe Phe Met Lys Val Tyr Gly Tyr Arg Gly Lys His Leu Gly Gly Ser
785                 790                 795                 800

Arg Lys Pro Asp Gly Ala Ile Tyr Thr Val Gly Ser Pro Ile Asp Tyr
                805                 810                 815

Gly Val Ile Val Asp Thr Lys Ala Tyr Ser Gly Gly Tyr Asn Leu Pro
            820                 825                 830

Ile Gly Gln Ala Asp Glu Met Gln Arg Tyr Val Glu Glu Asn Gln Thr
        835                 840                 845

Arg Asn Lys His Ile Asn Pro Asn Glu Trp Trp Lys Val Tyr Pro Ser
    850                 855                 860

Ser Val Thr Glu Phe Lys Phe Leu Phe Val Ser Gly His Phe Lys Gly
```

865 870 875 880

Asn Tyr Lys Ala Gln Leu Thr Arg Leu Asn His Ile Thr Asn Cys Asn
885 890 895

Gly Ala Val Leu Ser Val Glu Glu Leu Leu Ile Gly Gly Glu Met Ile
900 905 910

Lys Ala Gly Thr Leu Thr Leu Glu Glu Val Arg Arg Lys Phe Asn Asn
915 920 925

Gly Glu Ile Asn Phe Ala Ala Asp
930 935

<210> SEQ ID NO 22
<211> LENGTH: 942
<212> TYPE: PRT
<213> ORGANISM: artificial sequence
<220> FEATURE:
<223> OTHER INFORMATION: Right Talen for beta2M target 1

<400> SEQUENCE: 22

Met Gly Asp Pro Lys Lys Lys Arg Lys Val Ile Asp Lys Glu Thr Ala
1 5 10 15

Ala Ala Lys Phe Glu Arg Gln His Met Asp Ser Ile Asp Ile Ala Asp
20 25 30

Leu Arg Thr Leu Gly Tyr Ser Gln Gln Gln Gln Glu Lys Ile Lys Pro
35 40 45

Lys Val Arg Ser Thr Val Ala Gln His His Glu Ala Leu Val Gly His
50 55 60

Gly Phe Thr His Ala His Ile Val Ala Leu Ser Gln His Pro Ala Ala
65 70 75 80

Leu Gly Thr Val Ala Val Lys Tyr Gln Asp Met Ile Ala Ala Leu Pro
85 90 95

Glu Ala Thr His Glu Ala Ile Val Gly Val Gly Lys Gln Trp Ser Gly
100 105 110

Ala Arg Ala Leu Glu Ala Leu Leu Thr Val Ala Gly Glu Leu Arg Gly
115 120 125

Pro Pro Leu Gln Leu Asp Thr Gly Gln Leu Leu Lys Ile Ala Lys Arg
130 135 140

Gly Gly Val Thr Ala Val Glu Ala Val His Ala Trp Arg Asn Ala Leu
145 150 155 160

Thr Gly Ala Pro Leu Asn Leu Thr Pro Glu Gln Val Val Ala Ile Ala
165 170 175

Ser Asn Ile Gly Gly Lys Gln Ala Leu Glu Thr Val Gln Ala Leu Leu
180 185 190

Pro Val Leu Cys Gln Ala His Gly Leu Thr Pro Gln Gln Val Val Ala
195 200 205

Ile Ala Ser Asn Asn Gly Gly Lys Gln Ala Leu Glu Thr Val Gln Arg
210 215 220

Leu Leu Pro Val Leu Cys Gln Ala His Gly Leu Thr Pro Glu Gln Val
225 230 235 240

Val Ala Ile Ala Ser His Asp Gly Gly Lys Gln Ala Leu Glu Thr Val
245 250 255

Gln Arg Leu Leu Pro Val Leu Cys Gln Ala His Gly Leu Thr Pro Glu
260 265 270

Gln Val Val Ala Ile Ala Ser His Asp Gly Gly Lys Gln Ala Leu Glu
275 280 285

Thr Val Gln Arg Leu Leu Pro Val Leu Cys Gln Ala His Gly Leu Thr

```
    290                 295                 300

Pro Gln Gln Val Val Ala Ile Ala Ser Asn Gly Gly Gly Lys Gln Ala
305                 310                 315                 320

Leu Glu Thr Val Gln Arg Leu Leu Pro Val Leu Cys Gln Ala His Gly
                325                 330                 335

Leu Thr Pro Glu Gln Val Val Ala Ile Ala Ser His Asp Gly Gly Lys
            340                 345                 350

Gln Ala Leu Glu Thr Val Gln Arg Leu Leu Pro Val Leu Cys Gln Ala
        355                 360                 365

His Gly Leu Thr Pro Glu Gln Val Val Ala Ile Ala Ser His Asp Gly
    370                 375                 380

Gly Lys Gln Ala Leu Glu Thr Val Gln Arg Leu Leu Pro Val Leu Cys
385                 390                 395                 400

Gln Ala His Gly Leu Thr Pro Glu Gln Val Val Ala Ile Ala Ser Asn
                405                 410                 415

Ile Gly Gly Lys Gln Ala Leu Glu Thr Val Gln Ala Leu Leu Pro Val
            420                 425                 430

Leu Cys Gln Ala His Gly Leu Thr Pro Gln Gln Val Val Ala Ile Ala
        435                 440                 445

Ser Asn Asn Gly Gly Lys Gln Ala Leu Glu Thr Val Gln Arg Leu Leu
    450                 455                 460

Pro Val Leu Cys Gln Ala His Gly Leu Thr Pro Gln Gln Val Val Ala
465                 470                 475                 480

Ile Ala Ser Asn Asn Gly Gly Lys Gln Ala Leu Glu Thr Val Gln Arg
                485                 490                 495

Leu Leu Pro Val Leu Cys Gln Ala His Gly Leu Thr Pro Glu Gln Val
            500                 505                 510

Val Ala Ile Ala Ser His Asp Gly Gly Lys Gln Ala Leu Glu Thr Val
        515                 520                 525

Gln Arg Leu Leu Pro Val Leu Cys Gln Ala His Gly Leu Thr Pro Glu
    530                 535                 540

Gln Val Val Ala Ile Ala Ser His Asp Gly Gly Lys Gln Ala Leu Glu
545                 550                 555                 560

Thr Val Gln Arg Leu Leu Pro Val Leu Cys Gln Ala His Gly Leu Thr
                565                 570                 575

Pro Glu Gln Val Val Ala Ile Ala Ser Asn Ile Gly Gly Lys Gln Ala
            580                 585                 590

Leu Glu Thr Val Gln Ala Leu Leu Pro Val Leu Cys Gln Ala His Gly
        595                 600                 605

Leu Thr Pro Gln Gln Val Val Ala Ile Ala Ser Asn Asn Gly Gly Lys
    610                 615                 620

Gln Ala Leu Glu Thr Val Gln Arg Leu Leu Pro Val Leu Cys Gln Ala
625                 630                 635                 640

His Gly Leu Thr Pro Glu Gln Val Val Ala Ile Ala Ser Asn Ile Gly
                645                 650                 655

Gly Lys Gln Ala Leu Glu Thr Val Gln Ala Leu Leu Pro Val Leu Cys
            660                 665                 670

Gln Ala His Gly Leu Thr Pro Gln Gln Val Val Ala Ile Ala Ser Asn
        675                 680                 685

Gly Gly Gly Arg Pro Ala Leu Glu Ser Ile Val Ala Gln Leu Ser Arg
    690                 695                 700

Pro Asp Pro Ala Leu Ala Ala Leu Thr Asn Asp His Leu Val Ala Leu
705                 710                 715                 720
```

Ala Cys Leu Gly Gly Arg Pro Ala Leu Asp Ala Val Lys Lys Gly Leu
725 730 735

Gly Asp Pro Ile Ser Arg Ser Gln Leu Val Lys Ser Glu Leu Glu Glu
740 745 750

Lys Lys Ser Glu Leu Arg His Lys Leu Lys Tyr Val Pro His Glu Tyr
755 760 765

Ile Glu Leu Ile Glu Ile Ala Arg Asn Ser Thr Gln Asp Arg Ile Leu
770 775 780

Glu Met Lys Val Met Glu Phe Phe Met Lys Val Tyr Gly Tyr Arg Gly
785 790 795 800

Lys His Leu Gly Gly Ser Arg Lys Pro Asp Gly Ala Ile Tyr Thr Val
805 810 815

Gly Ser Pro Ile Asp Tyr Gly Val Ile Val Asp Thr Lys Ala Tyr Ser
820 825 830

Gly Gly Tyr Asn Leu Pro Ile Gly Gln Ala Asp Glu Met Gln Arg Tyr
835 840 845

Val Glu Glu Asn Gln Thr Arg Asn Lys His Ile Asn Pro Asn Glu Trp
850 855 860

Trp Lys Val Tyr Pro Ser Ser Val Thr Glu Phe Lys Phe Leu Phe Val
865 870 875 880

Ser Gly His Phe Lys Gly Asn Tyr Lys Ala Gln Leu Thr Arg Leu Asn
885 890 895

His Ile Thr Asn Cys Asn Gly Ala Val Leu Ser Val Glu Glu Leu Leu
900 905 910

Ile Gly Gly Glu Met Ile Lys Ala Gly Thr Leu Thr Leu Glu Glu Val
915 920 925

Arg Arg Lys Phe Asn Asn Gly Glu Ile Asn Phe Ala Ala Asp
930 935 940

<210> SEQ ID NO 23
<211> LENGTH: 50
<212> TYPE: DNA
<213> ORGANISM: homo sapiens
<220> FEATURE:
<223> OTHER INFORMATION: Beta2M target 2

<400> SEQUENCE: 23
tccaaagatt caggtttact cacgtcatcc agcagagaat ggaaagtcaa 50

<210> SEQ ID NO 24
<211> LENGTH: 936
<212> TYPE: PRT
<213> ORGANISM: artificial sequence
<220> FEATURE:
<223> OTHER INFORMATION: Left Talen for beta2M target 2

<400> SEQUENCE: 24

Met Gly Asp Pro Lys Lys Lys Arg Lys Val Ile Asp Tyr Pro Tyr Asp
1 5 10 15

Val Pro Asp Tyr Ala Ile Asp Ile Ala Asp Leu Arg Thr Leu Gly Tyr
20 25 30

Ser Gln Gln Gln Gln Glu Lys Ile Lys Pro Lys Val Arg Ser Thr Val
35 40 45

Ala Gln His His Glu Ala Leu Val Gly His Gly Phe Thr His Ala His
50 55 60

Ile Val Ala Leu Ser Gln His Pro Ala Ala Leu Gly Thr Val Ala Val
65 70 75 80

```
Lys Tyr Gln Asp Met Ile Ala Ala Leu Pro Glu Ala Thr His Glu Ala
                85                  90                  95

Ile Val Gly Val Gly Lys Gln Trp Ser Gly Ala Arg Ala Leu Glu Ala
            100                 105                 110

Leu Leu Thr Val Ala Gly Glu Leu Arg Gly Pro Pro Leu Gln Leu Asp
        115                 120                 125

Thr Gly Gln Leu Leu Lys Ile Ala Lys Arg Gly Gly Val Thr Ala Val
    130                 135                 140

Glu Ala Val His Ala Trp Arg Asn Ala Leu Thr Gly Ala Pro Leu Asn
145                 150                 155                 160

Leu Thr Pro Glu Gln Val Val Ala Ile Ala Ser His Asp Gly Gly Lys
                165                 170                 175

Gln Ala Leu Glu Thr Val Gln Arg Leu Leu Pro Val Leu Cys Gln Ala
            180                 185                 190

His Gly Leu Thr Pro Glu Gln Val Val Ala Ile Ala Ser His Asp Gly
        195                 200                 205

Gly Lys Gln Ala Leu Glu Thr Val Gln Arg Leu Leu Pro Val Leu Cys
    210                 215                 220

Gln Ala His Gly Leu Thr Pro Glu Gln Val Val Ala Ile Ala Ser Asn
225                 230                 235                 240

Ile Gly Gly Lys Gln Ala Leu Glu Thr Val Gln Ala Leu Leu Pro Val
                245                 250                 255

Leu Cys Gln Ala His Gly Leu Thr Pro Glu Gln Val Val Ala Ile Ala
            260                 265                 270

Ser Asn Ile Gly Gly Lys Gln Ala Leu Glu Thr Val Gln Ala Leu Leu
        275                 280                 285

Pro Val Leu Cys Gln Ala His Gly Leu Thr Pro Glu Gln Val Val Ala
    290                 295                 300

Ile Ala Ser Asn Ile Gly Gly Lys Gln Ala Leu Glu Thr Val Gln Ala
305                 310                 315                 320

Leu Leu Pro Val Leu Cys Gln Ala His Gly Leu Thr Pro Gln Gln Val
                325                 330                 335

Val Ala Ile Ala Ser Asn Asn Gly Gly Lys Gln Ala Leu Glu Thr Val
            340                 345                 350

Gln Arg Leu Leu Pro Val Leu Cys Gln Ala His Gly Leu Thr Pro Glu
        355                 360                 365

Gln Val Val Ala Ile Ala Ser Asn Ile Gly Gly Lys Gln Ala Leu Glu
    370                 375                 380

Thr Val Gln Ala Leu Leu Pro Val Leu Cys Gln Ala His Gly Leu Thr
385                 390                 395                 400

Pro Gln Gln Val Val Ala Ile Ala Ser Asn Gly Gly Gly Lys Gln Ala
                405                 410                 415

Leu Glu Thr Val Gln Arg Leu Leu Pro Val Leu Cys Gln Ala His Gly
            420                 425                 430

Leu Thr Pro Gln Gln Val Val Ala Ile Ala Ser Asn Gly Gly Gly Lys
        435                 440                 445

Gln Ala Leu Glu Thr Val Gln Arg Leu Leu Pro Val Leu Cys Gln Ala
    450                 455                 460

His Gly Leu Thr Pro Glu Gln Val Val Ala Ile Ala Ser His Asp Gly
465                 470                 475                 480

Gly Lys Gln Ala Leu Glu Thr Val Gln Arg Leu Leu Pro Val Leu Cys
                485                 490                 495
```

Gln Ala His Gly Leu Thr Pro Glu Gln Val Val Ala Ile Ala Ser Asn
500 505 510

Ile Gly Gly Lys Gln Ala Leu Glu Thr Val Gln Ala Leu Leu Pro Val
515 520 525

Leu Cys Gln Ala His Gly Leu Thr Pro Gln Gln Val Val Ala Ile Ala
530 535 540

Ser Asn Asn Gly Gly Lys Gln Ala Leu Glu Thr Val Gln Arg Leu Leu
545 550 555 560

Pro Val Leu Cys Gln Ala His Gly Leu Thr Pro Gln Gln Val Val Ala
565 570 575

Ile Ala Ser Asn Asn Gly Gly Lys Gln Ala Leu Glu Thr Val Gln Arg
580 585 590

Leu Leu Pro Val Leu Cys Gln Ala His Gly Leu Thr Pro Gln Gln Val
595 600 605

Val Ala Ile Ala Ser Asn Gly Gly Gly Lys Gln Ala Leu Glu Thr Val
610 615 620

Gln Arg Leu Leu Pro Val Leu Cys Gln Ala His Gly Leu Thr Pro Gln
625 630 635 640

Gln Val Val Ala Ile Ala Ser Asn Gly Gly Gly Lys Gln Ala Leu Glu
645 650 655

Thr Val Gln Arg Leu Leu Pro Val Leu Cys Gln Ala His Gly Leu Thr
660 665 670

Pro Gln Gln Val Val Ala Ile Ala Ser Asn Gly Gly Gly Arg Pro Ala
675 680 685

Leu Glu Ser Ile Val Ala Gln Leu Ser Arg Pro Asp Pro Ala Leu Ala
690 695 700

Ala Leu Thr Asn Asp His Leu Val Ala Leu Ala Cys Leu Gly Gly Arg
705 710 715 720

Pro Ala Leu Asp Ala Val Lys Lys Gly Leu Gly Asp Pro Ile Ser Arg
725 730 735

Ser Gln Leu Val Lys Ser Glu Leu Glu Glu Lys Lys Ser Glu Leu Arg
740 745 750

His Lys Leu Lys Tyr Val Pro His Glu Tyr Ile Glu Leu Ile Glu Ile
755 760 765

Ala Arg Asn Ser Thr Gln Asp Arg Ile Leu Glu Met Lys Val Met Glu
770 775 780

Phe Phe Met Lys Val Tyr Gly Tyr Arg Gly Lys His Leu Gly Gly Ser
785 790 795 800

Arg Lys Pro Asp Gly Ala Ile Tyr Thr Val Gly Ser Pro Ile Asp Tyr
805 810 815

Gly Val Ile Val Asp Thr Lys Ala Tyr Ser Gly Gly Tyr Asn Leu Pro
820 825 830

Ile Gly Gln Ala Asp Glu Met Gln Arg Tyr Val Glu Glu Asn Gln Thr
835 840 845

Arg Asn Lys His Ile Asn Pro Asn Glu Trp Trp Lys Val Tyr Pro Ser
850 855 860

Ser Val Thr Glu Phe Lys Phe Leu Phe Val Ser Gly His Phe Lys Gly
865 870 875 880

Asn Tyr Lys Ala Gln Leu Thr Arg Leu Asn His Ile Thr Asn Cys Asn
885 890 895

Gly Ala Val Leu Ser Val Glu Glu Leu Leu Ile Gly Gly Glu Met Ile
900 905 910

Lys Ala Gly Thr Leu Thr Leu Glu Glu Val Arg Arg Lys Phe Asn Asn

```
        915                 920                 925

Gly Glu Ile Asn Phe Ala Ala Asp
    930                 935


<210> SEQ ID NO 25
<211> LENGTH: 942
<212> TYPE: PRT
<213> ORGANISM: artificial sequence
<220> FEATURE:
<223> OTHER INFORMATION: Right Talen for beta2M target 2

<400> SEQUENCE: 25

Met Gly Asp Pro Lys Lys Lys Arg Lys Val Ile Asp Lys Glu Thr Ala
1               5                   10                  15

Ala Ala Lys Phe Glu Arg Gln His Met Asp Ser Ile Asp Ile Ala Asp
            20                  25                  30

Leu Arg Thr Leu Gly Tyr Ser Gln Gln Gln Glu Lys Ile Lys Pro
        35                  40                  45

Lys Val Arg Ser Thr Val Ala Gln His His Glu Ala Leu Val Gly His
    50                  55                  60

Gly Phe Thr His Ala His Ile Val Ala Leu Ser Gln His Pro Ala Ala
65                  70                  75                  80

Leu Gly Thr Val Ala Val Lys Tyr Gln Asp Met Ile Ala Ala Leu Pro
                85                  90                  95

Glu Ala Thr His Glu Ala Ile Val Gly Val Gly Lys Gln Trp Ser Gly
            100                 105                 110

Ala Arg Ala Leu Glu Ala Leu Leu Thr Val Ala Gly Glu Leu Arg Gly
        115                 120                 125

Pro Pro Leu Gln Leu Asp Thr Gly Gln Leu Leu Lys Ile Ala Lys Arg
    130                 135                 140

Gly Gly Val Thr Ala Val Glu Ala Val His Ala Trp Arg Asn Ala Leu
145                 150                 155                 160

Thr Gly Ala Pro Leu Asn Leu Thr Pro Gln Gln Val Val Ala Ile Ala
                165                 170                 175

Ser Asn Asn Gly Gly Lys Gln Ala Leu Glu Thr Val Gln Arg Leu Leu
            180                 185                 190

Pro Val Leu Cys Gln Ala His Gly Leu Thr Pro Glu Gln Val Val Ala
        195                 200                 205

Ile Ala Ser Asn Ile Gly Gly Lys Gln Ala Leu Glu Thr Val Gln Ala
    210                 215                 220

Leu Leu Pro Val Leu Cys Gln Ala His Gly Leu Thr Pro Glu Gln Val
225                 230                 235                 240

Val Ala Ile Ala Ser His Asp Gly Gly Lys Gln Ala Leu Glu Thr Val
                245                 250                 255

Gln Arg Leu Leu Pro Val Leu Cys Gln Ala His Gly Leu Thr Pro Gln
            260                 265                 270

Gln Val Val Ala Ile Ala Ser Asn Gly Gly Gly Lys Gln Ala Leu Glu
        275                 280                 285

Thr Val Gln Arg Leu Leu Pro Val Leu Cys Gln Ala His Gly Leu Thr
    290                 295                 300

Pro Gln Gln Val Val Ala Ile Ala Ser Asn Gly Gly Gly Lys Gln Ala
305                 310                 315                 320

Leu Glu Thr Val Gln Arg Leu Leu Pro Val Leu Cys Gln Ala His Gly
                325                 330                 335

Leu Thr Pro Gln Gln Val Val Ala Ile Ala Ser Asn Gly Gly Gly Lys
```

```
            340                 345                 350

Gln Ala Leu Glu Thr Val Gln Arg Leu Leu Pro Val Leu Cys Gln Ala
        355                 360                 365

His Gly Leu Thr Pro Glu Gln Val Val Ala Ile Ala Ser His Asp Gly
    370                 375                 380

Gly Lys Gln Ala Leu Glu Thr Val Gln Arg Leu Leu Pro Val Leu Cys
385                 390                 395                 400

Gln Ala His Gly Leu Thr Pro Glu Gln Val Val Ala Ile Ala Ser His
                405                 410                 415

Asp Gly Gly Lys Gln Ala Leu Glu Thr Val Gln Arg Leu Leu Pro Val
            420                 425                 430

Leu Cys Gln Ala His Gly Leu Thr Pro Glu Gln Val Val Ala Ile Ala
        435                 440                 445

Ser Asn Ile Gly Gly Lys Gln Ala Leu Glu Thr Val Gln Ala Leu Leu
    450                 455                 460

Pro Val Leu Cys Gln Ala His Gly Leu Thr Pro Gln Gln Val Val Ala
465                 470                 475                 480

Ile Ala Ser Asn Gly Gly Gly Lys Gln Ala Leu Glu Thr Val Gln Arg
                485                 490                 495

Leu Leu Pro Val Leu Cys Gln Ala His Gly Leu Thr Pro Gln Gln Val
            500                 505                 510

Val Ala Ile Ala Ser Asn Gly Gly Gly Lys Gln Ala Leu Glu Thr Val
        515                 520                 525

Gln Arg Leu Leu Pro Val Leu Cys Gln Ala His Gly Leu Thr Pro Glu
    530                 535                 540

Gln Val Val Ala Ile Ala Ser His Asp Gly Gly Lys Gln Ala Leu Glu
545                 550                 555                 560

Thr Val Gln Arg Leu Leu Pro Val Leu Cys Gln Ala His Gly Leu Thr
                565                 570                 575

Pro Gln Gln Val Val Ala Ile Ala Ser Asn Gly Gly Gly Lys Gln Ala
            580                 585                 590

Leu Glu Thr Val Gln Arg Leu Leu Pro Val Leu Cys Gln Ala His Gly
        595                 600                 605

Leu Thr Pro Glu Gln Val Val Ala Ile Ala Ser His Asp Gly Gly Lys
    610                 615                 620

Gln Ala Leu Glu Thr Val Gln Arg Leu Leu Pro Val Leu Cys Gln Ala
625                 630                 635                 640

His Gly Leu Thr Pro Gln Gln Val Val Ala Ile Ala Ser Asn Gly Gly
                645                 650                 655

Gly Lys Gln Ala Leu Glu Thr Val Gln Arg Leu Leu Pro Val Leu Cys
            660                 665                 670

Gln Ala His Gly Leu Thr Pro Gln Gln Val Val Ala Ile Ala Ser Asn
        675                 680                 685

Gly Gly Gly Arg Pro Ala Leu Glu Ser Ile Val Ala Gln Leu Ser Arg
    690                 695                 700

Pro Asp Pro Ala Leu Ala Ala Leu Thr Asn Asp His Leu Val Ala Leu
705                 710                 715                 720

Ala Cys Leu Gly Gly Arg Pro Ala Leu Asp Ala Val Lys Lys Gly Leu
                725                 730                 735

Gly Asp Pro Ile Ser Arg Ser Gln Leu Val Lys Ser Glu Leu Glu Glu
            740                 745                 750

Lys Lys Ser Glu Leu Arg His Lys Leu Lys Tyr Val Pro His Glu Tyr
        755                 760                 765
```

Ile Glu Leu Ile Glu Ile Ala Arg Asn Ser Thr Gln Asp Arg Ile Leu
770 775 780

Glu Met Lys Val Met Glu Phe Phe Met Lys Val Tyr Gly Tyr Arg Gly
785 790 795 800

Lys His Leu Gly Gly Ser Arg Lys Pro Asp Gly Ala Ile Tyr Thr Val
805 810 815

Gly Ser Pro Ile Asp Tyr Gly Val Ile Val Asp Thr Lys Ala Tyr Ser
820 825 830

Gly Gly Tyr Asn Leu Pro Ile Gly Gln Ala Asp Glu Met Gln Arg Tyr
835 840 845

Val Glu Glu Asn Gln Thr Arg Asn Lys His Ile Asn Pro Asn Glu Trp
850 855 860

Trp Lys Val Tyr Pro Ser Ser Val Thr Glu Phe Lys Phe Leu Phe Val
865 870 875 880

Ser Gly His Phe Lys Gly Asn Tyr Lys Ala Gln Leu Thr Arg Leu Asn
885 890 895

His Ile Thr Asn Cys Asn Gly Ala Val Leu Ser Val Glu Glu Leu Leu
900 905 910

Ile Gly Gly Glu Met Ile Lys Ala Gly Thr Leu Thr Leu Glu Glu Val
915 920 925

Arg Arg Lys Phe Asn Asn Gly Glu Ile Asn Phe Ala Ala Asp
930 935 940

<210> SEQ ID NO 26
<211> LENGTH: 47
<212> TYPE: DNA
<213> ORGANISM: homo sapiens
<220> FEATURE:
<223> OTHER INFORMATION: Beta2M target 3

<400> SEQUENCE: 26
ttagctgtgc tcgcgctact ctctctttct ggcctggagg ctatcca 47

<210> SEQ ID NO 27
<211> LENGTH: 936
<212> TYPE: PRT
<213> ORGANISM: artificial sequence
<220> FEATURE:
<223> OTHER INFORMATION: Left Talen for beta2M target 3

<400> SEQUENCE: 27

Met Gly Asp Pro Lys Lys Lys Arg Lys Val Ile Asp Tyr Pro Tyr Asp
1 5 10 15

Val Pro Asp Tyr Ala Ile Asp Ile Ala Asp Leu Arg Thr Leu Gly Tyr
20 25 30

Ser Gln Gln Gln Gln Glu Lys Ile Lys Pro Lys Val Arg Ser Thr Val
35 40 45

Ala Gln His His Glu Ala Leu Val Gly His Gly Phe Thr His Ala His
50 55 60

Ile Val Ala Leu Ser Gln His Pro Ala Ala Leu Gly Thr Val Ala Val
65 70 75 80

Lys Tyr Gln Asp Met Ile Ala Ala Leu Pro Glu Ala Thr His Glu Ala
85 90 95

Ile Val Gly Val Gly Lys Gln Trp Ser Gly Ala Arg Ala Leu Glu Ala
100 105 110

Leu Leu Thr Val Ala Gly Glu Leu Arg Gly Pro Pro Leu Gln Leu Asp
115 120 125

```
Thr Gly Gln Leu Leu Lys Ile Ala Lys Arg Gly Gly Val Thr Ala Val
    130                 135                 140

Glu Ala Val His Ala Trp Arg Asn Ala Leu Thr Gly Ala Pro Leu Asn
145                 150                 155                 160

Leu Thr Pro Glu Gln Val Val Ala Ile Ala Ser Asn Ile Gly Gly Lys
                165                 170                 175

Gln Ala Leu Glu Thr Val Gln Ala Leu Leu Pro Val Leu Cys Gln Ala
            180                 185                 190

His Gly Leu Thr Pro Gln Gln Val Val Ala Ile Ala Ser Asn Asn Gly
        195                 200                 205

Gly Lys Gln Ala Leu Glu Thr Val Gln Arg Leu Leu Pro Val Leu Cys
    210                 215                 220

Gln Ala His Gly Leu Thr Pro Glu Gln Val Val Ala Ile Ala Ser His
225                 230                 235                 240

Asp Gly Gly Lys Gln Ala Leu Glu Thr Val Gln Arg Leu Leu Pro Val
                245                 250                 255

Leu Cys Gln Ala His Gly Leu Thr Pro Gln Gln Val Val Ala Ile Ala
            260                 265                 270

Ser Asn Gly Gly Gly Lys Gln Ala Leu Glu Thr Val Gln Arg Leu Leu
        275                 280                 285

Pro Val Leu Cys Gln Ala His Gly Leu Thr Pro Gln Gln Val Val Ala
    290                 295                 300

Ile Ala Ser Asn Asn Gly Gly Lys Gln Ala Leu Glu Thr Val Gln Arg
305                 310                 315                 320

Leu Leu Pro Val Leu Cys Gln Ala His Gly Leu Thr Pro Gln Gln Val
                325                 330                 335

Val Ala Ile Ala Ser Asn Gly Gly Gly Lys Gln Ala Leu Glu Thr Val
            340                 345                 350

Gln Arg Leu Leu Pro Val Leu Cys Gln Ala His Gly Leu Thr Pro Gln
        355                 360                 365

Gln Val Val Ala Ile Ala Ser Asn Asn Gly Gly Lys Gln Ala Leu Glu
    370                 375                 380

Thr Val Gln Arg Leu Leu Pro Val Leu Cys Gln Ala His Gly Leu Thr
385                 390                 395                 400

Pro Glu Gln Val Val Ala Ile Ala Ser His Asp Gly Gly Lys Gln Ala
                405                 410                 415

Leu Glu Thr Val Gln Arg Leu Leu Pro Val Leu Cys Gln Ala His Gly
            420                 425                 430

Leu Thr Pro Gln Gln Val Val Ala Ile Ala Ser Asn Gly Gly Gly Lys
        435                 440                 445

Gln Ala Leu Glu Thr Val Gln Arg Leu Leu Pro Val Leu Cys Gln Ala
    450                 455                 460

His Gly Leu Thr Pro Glu Gln Val Val Ala Ile Ala Ser His Asp Gly
465                 470                 475                 480

Gly Lys Gln Ala Leu Glu Thr Val Gln Arg Leu Leu Pro Val Leu Cys
                485                 490                 495

Gln Ala His Gly Leu Thr Pro Gln Gln Val Val Ala Ile Ala Ser Asn
            500                 505                 510

Asn Gly Gly Lys Gln Ala Leu Glu Thr Val Gln Arg Leu Leu Pro Val
        515                 520                 525

Leu Cys Gln Ala His Gly Leu Thr Pro Glu Gln Val Val Ala Ile Ala
    530                 535                 540
```

```
Ser His Asp Gly Gly Lys Gln Ala Leu Glu Thr Val Gln Arg Leu Leu
545                 550                 555                 560

Pro Val Leu Cys Gln Ala His Gly Leu Thr Pro Gln Gln Val Val Ala
                565                 570                 575

Ile Ala Ser Asn Asn Gly Gly Lys Gln Ala Leu Glu Thr Val Gln Arg
            580                 585                 590

Leu Leu Pro Val Leu Cys Gln Ala His Gly Leu Thr Pro Glu Gln Val
        595                 600                 605

Val Ala Ile Ala Ser His Asp Gly Gly Lys Gln Ala Leu Glu Thr Val
    610                 615                 620

Gln Arg Leu Leu Pro Val Leu Cys Gln Ala His Gly Leu Thr Pro Gln
625                 630                 635                 640

Gln Val Val Ala Ile Ala Ser Asn Gly Gly Gly Lys Gln Ala Leu Glu
                645                 650                 655

Thr Val Gln Arg Leu Leu Pro Val Leu Cys Gln Ala His Gly Leu Thr
            660                 665                 670

Pro Gln Gln Val Val Ala Ile Ala Ser Asn Gly Gly Gly Arg Pro Ala
        675                 680                 685

Leu Glu Ser Ile Val Ala Gln Leu Ser Arg Pro Asp Pro Ala Leu Ala
    690                 695                 700

Ala Leu Thr Asn Asp His Leu Val Ala Leu Ala Cys Leu Gly Gly Arg
705                 710                 715                 720

Pro Ala Leu Asp Ala Val Lys Lys Gly Leu Gly Asp Pro Ile Ser Arg
                725                 730                 735

Ser Gln Leu Val Lys Ser Glu Leu Glu Glu Lys Lys Ser Glu Leu Arg
            740                 745                 750

His Lys Leu Lys Tyr Val Pro His Glu Tyr Ile Glu Leu Ile Glu Ile
        755                 760                 765

Ala Arg Asn Ser Thr Gln Asp Arg Ile Leu Glu Met Lys Val Met Glu
    770                 775                 780

Phe Phe Met Lys Val Tyr Gly Tyr Arg Gly Lys His Leu Gly Gly Ser
785                 790                 795                 800

Arg Lys Pro Asp Gly Ala Ile Tyr Thr Val Gly Ser Pro Ile Asp Tyr
                805                 810                 815

Gly Val Ile Val Asp Thr Lys Ala Tyr Ser Gly Gly Tyr Asn Leu Pro
            820                 825                 830

Ile Gly Gln Ala Asp Glu Met Gln Arg Tyr Val Glu Glu Asn Gln Thr
        835                 840                 845

Arg Asn Lys His Ile Asn Pro Asn Glu Trp Trp Lys Val Tyr Pro Ser
    850                 855                 860

Ser Val Thr Glu Phe Lys Phe Leu Phe Val Ser Gly His Phe Lys Gly
865                 870                 875                 880

Asn Tyr Lys Ala Gln Leu Thr Arg Leu Asn His Ile Thr Asn Cys Asn
                885                 890                 895

Gly Ala Val Leu Ser Val Glu Glu Leu Leu Ile Gly Gly Glu Met Ile
            900                 905                 910

Lys Ala Gly Thr Leu Thr Leu Glu Glu Val Arg Arg Lys Phe Asn Asn
        915                 920                 925

Gly Glu Ile Asn Phe Ala Ala Asp
    930                 935
```

<210> SEQ ID NO 28
<211> LENGTH: 942
<212> TYPE: PRT

<213> ORGANISM: artificial sequence
<220> FEATURE:
<223> OTHER INFORMATION: Right Talen for beta2M target 3

<400> SEQUENCE: 28

Met Gly Asp Pro Lys Lys Lys Arg Lys Val Ile Asp Lys Glu Thr Ala
1               5                   10                  15

Ala Ala Lys Phe Glu Arg Gln His Met Asp Ser Ile Asp Ile Ala Asp
            20                  25                  30

Leu Arg Thr Leu Gly Tyr Ser Gln Gln Gln Gln Glu Lys Ile Lys Pro
        35                  40                  45

Lys Val Arg Ser Thr Val Ala Gln His His Glu Ala Leu Val Gly His
    50                  55                  60

Gly Phe Thr His Ala His Ile Val Ala Leu Ser Gln His Pro Ala Ala
65                  70                  75                  80

Leu Gly Thr Val Ala Val Lys Tyr Gln Asp Met Ile Ala Ala Leu Pro
                85                  90                  95

Glu Ala Thr His Glu Ala Ile Val Gly Val Gly Lys Gln Trp Ser Gly
            100                 105                 110

Ala Arg Ala Leu Glu Ala Leu Leu Thr Val Ala Gly Glu Leu Arg Gly
        115                 120                 125

Pro Pro Leu Gln Leu Asp Thr Gly Gln Leu Leu Lys Ile Ala Lys Arg
    130                 135                 140

Gly Gly Val Thr Ala Val Glu Ala Val His Ala Trp Arg Asn Ala Leu
145                 150                 155                 160

Thr Gly Ala Pro Leu Asn Leu Thr Pro Gln Gln Val Val Ala Ile Ala
                165                 170                 175

Ser Asn Asn Gly Gly Lys Gln Ala Leu Glu Thr Val Gln Arg Leu Leu
            180                 185                 190

Pro Val Leu Cys Gln Ala His Gly Leu Thr Pro Gln Gln Val Val Ala
        195                 200                 205

Ile Ala Ser Asn Asn Gly Gly Lys Gln Ala Leu Glu Thr Val Gln Arg
    210                 215                 220

Leu Leu Pro Val Leu Cys Gln Ala His Gly Leu Thr Pro Glu Gln Val
225                 230                 235                 240

Val Ala Ile Ala Ser Asn Ile Gly Gly Lys Gln Ala Leu Glu Thr Val
                245                 250                 255

Gln Ala Leu Leu Pro Val Leu Cys Gln Ala His Gly Leu Thr Pro Gln
            260                 265                 270

Gln Val Val Ala Ile Ala Ser Asn Gly Gly Gly Lys Gln Ala Leu Glu
        275                 280                 285

Thr Val Gln Arg Leu Leu Pro Val Leu Cys Gln Ala His Gly Leu Thr
    290                 295                 300

Pro Glu Gln Val Val Ala Ile Ala Ser Asn Ile Gly Gly Lys Gln Ala
305                 310                 315                 320

Leu Glu Thr Val Gln Ala Leu Leu Pro Val Leu Cys Gln Ala His Gly
                325                 330                 335

Leu Thr Pro Gln Gln Val Val Ala Ile Ala Ser Asn Asn Gly Gly Lys
            340                 345                 350

Gln Ala Leu Glu Thr Val Gln Arg Leu Leu Pro Val Leu Cys Gln Ala
        355                 360                 365

His Gly Leu Thr Pro Glu Gln Val Val Ala Ile Ala Ser His Asp Gly
    370                 375                 380

Gly Lys Gln Ala Leu Glu Thr Val Gln Arg Leu Leu Pro Val Leu Cys

```
385                 390                 395                 400

Gln Ala His Gly Leu Thr Pro Glu Gln Val Val Ala Ile Ala Ser His
                405                 410                 415

Asp Gly Gly Lys Gln Ala Leu Glu Thr Val Gln Arg Leu Leu Pro Val
            420                 425                 430

Leu Cys Gln Ala His Gly Leu Thr Pro Gln Gln Val Val Ala Ile Ala
        435                 440                 445

Ser Asn Gly Gly Gly Lys Gln Ala Leu Glu Thr Val Gln Arg Leu Leu
    450                 455                 460

Pro Val Leu Cys Gln Ala His Gly Leu Thr Pro Glu Gln Val Val Ala
465                 470                 475                 480

Ile Ala Ser His Asp Gly Gly Lys Gln Ala Leu Glu Thr Val Gln Arg
                485                 490                 495

Leu Leu Pro Val Leu Cys Gln Ala His Gly Leu Thr Pro Glu Gln Val
            500                 505                 510

Val Ala Ile Ala Ser His Asp Gly Gly Lys Gln Ala Leu Glu Thr Val
        515                 520                 525

Gln Arg Leu Leu Pro Val Leu Cys Gln Ala His Gly Leu Thr Pro Glu
    530                 535                 540

Gln Val Val Ala Ile Ala Ser Asn Ile Gly Gly Lys Gln Ala Leu Glu
545                 550                 555                 560

Thr Val Gln Ala Leu Leu Pro Val Leu Cys Gln Ala His Gly Leu Thr
                565                 570                 575

Pro Gln Gln Val Val Ala Ile Ala Ser Asn Asn Gly Gly Lys Gln Ala
            580                 585                 590

Leu Glu Thr Val Gln Arg Leu Leu Pro Val Leu Cys Gln Ala His Gly
        595                 600                 605

Leu Thr Pro Gln Gln Val Val Ala Ile Ala Ser Asn Asn Gly Gly Lys
    610                 615                 620

Gln Ala Leu Glu Thr Val Gln Arg Leu Leu Pro Val Leu Cys Gln Ala
625                 630                 635                 640

His Gly Leu Thr Pro Glu Gln Val Val Ala Ile Ala Ser His Asp Gly
                645                 650                 655

Gly Lys Gln Ala Leu Glu Thr Val Gln Arg Leu Leu Pro Val Leu Cys
            660                 665                 670

Gln Ala His Gly Leu Thr Pro Gln Gln Val Val Ala Ile Ala Ser Asn
        675                 680                 685

Gly Gly Gly Arg Pro Ala Leu Glu Ser Ile Val Ala Gln Leu Ser Arg
    690                 695                 700

Pro Asp Pro Ala Leu Ala Ala Leu Thr Asn Asp His Leu Val Ala Leu
705                 710                 715                 720

Ala Cys Leu Gly Gly Arg Pro Ala Leu Asp Ala Val Lys Lys Gly Leu
                725                 730                 735

Gly Asp Pro Ile Ser Arg Ser Gln Leu Val Lys Ser Glu Leu Glu Glu
            740                 745                 750

Lys Lys Ser Glu Leu Arg His Lys Leu Lys Tyr Val Pro His Glu Tyr
        755                 760                 765

Ile Glu Leu Ile Glu Ile Ala Arg Asn Ser Thr Gln Asp Arg Ile Leu
    770                 775                 780

Glu Met Lys Val Met Glu Phe Phe Met Lys Val Tyr Gly Tyr Arg Gly
785                 790                 795                 800

Lys His Leu Gly Gly Ser Arg Lys Pro Asp Gly Ala Ile Tyr Thr Val
                805                 810                 815
```

```
Gly Ser Pro Ile Asp Tyr Gly Val Ile Val Asp Thr Lys Ala Tyr Ser
            820                 825                 830

Gly Gly Tyr Asn Leu Pro Ile Gly Gln Ala Asp Glu Met Gln Arg Tyr
        835                 840                 845

Val Glu Glu Asn Gln Thr Arg Asn Lys His Ile Asn Pro Asn Glu Trp
    850                 855                 860

Trp Lys Val Tyr Pro Ser Ser Val Thr Glu Phe Lys Phe Leu Phe Val
865                 870                 875                 880

Ser Gly His Phe Lys Gly Asn Tyr Lys Ala Gln Leu Thr Arg Leu Asn
                885                 890                 895

His Ile Thr Asn Cys Asn Gly Ala Val Leu Ser Val Glu Glu Leu Leu
            900                 905                 910

Ile Gly Gly Glu Met Ile Lys Ala Gly Thr Leu Thr Leu Glu Glu Val
        915                 920                 925

Arg Arg Lys Phe Asn Asn Gly Glu Ile Asn Phe Ala Ala Asp
    930                 935                 940


<210> SEQ ID NO 29
<211> LENGTH: 119
<212> TYPE: PRT
<213> ORGANISM: homo sapiens
<220> FEATURE:
<223> OTHER INFORMATION: &#946;2m protein sequence

<400> SEQUENCE: 29

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met
        115


<210> SEQ ID NO 30
<211> LENGTH: 238
<212> TYPE: PRT
<213> ORGANISM: Jellyfish
<220> FEATURE:
<223> OTHER INFORMATION: GFP protein

<400> SEQUENCE: 30

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
```

-continued

```
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235
```

METHODS FOR IMPROVING FUNCTIONALITY IN NK CELL BY GENE INACTIVATION USING SPECIFIC ENDONUCLEASE

FIELD OF THE INVENTION

The present invention relates to methods for improving the functionality of NK cell, such as their cytotoxic/cytolytic activity, to be used in immunotherapy. In particular, these methods comprise a step of gene inactivation using specific endonuclease such as TAL-nucleases, CRISPR or Argonaute. An additional genetic modification can be performed by overexpressing at least one gene involved in NK function. The present invention encompasses also an engineered NK cell, pharmaceutical composition containing the same.

BACKGROUND OF THE INVENTION

NK cells are the major cellular effectors of the innate immune system, which function alone or in synchrony with other immune cells, to abrogate a variety of targets including virally infected and transformed cells as well as those under stress or heat shock. NK cells are large granular lymphocytes, which respond spontaneously to cells under insult using their germline-encoded receptors and require no prior exposure to antigen. NK cells thus became established as a potentially useful population for adoptive immunotherapy against tumors (Topalian S L, Rosenberg S A, 1987, Acta Haematol.; 78(Suppl 1):75-76). Besides their role in tumor immunosurveillance, NK cells mediate many different biological processes ranging from the development of autoimmunity to the outcome of pregnancy and transplants or clearance of infections (Vivier E, Tomasello E, Baratin M, Walzer T, Ugolini S. 2008 9(5):503-510).

Both innate and adaptive immune cells actively prevent neoplastic development in a process called 'cancer immunosurveillance'. Innate immune cells, including monocytes, macrophages, dendritic cells (DCs) and natural killer (NK) cells, mediate immediate, short-lived responses by releasing cytokines that directly lyse tumor cells or capture debris from dead tumor cells.

NK cells rapidly kill certain target cells without prior immunization or MHC restriction, whose activation is dependent on the balance between inhibitory and activating signals from invariant receptors (Cerwenka A, Lanier L L. "Natural killer cells, viruses and cancer". Nat Rev Immunol 2001; 1: 41-49; Miller J S. "The biology of natural killer cells in cancer, infection, and pregnancy". Exp Hematol 2001; 29: 1157-1168). The activating receptors include the cytotoxicity receptors (NCRs) (NKp46, NKp30 and NKp44), C-type lectin receptors (CD94/NKG2C, NKG2D, NKG2E/H and NKG2F) and killer cell immunoglobulin-like receptors (KIRs) (KIR-2DS and KIR-3DS), while the inhibitory receptors include C-type lectin receptors (CD94/NKG2A/B) and KIRs (KIR-2DL and KIR-3DL). Since some structural families contain both activating and inhibitory receptors, trying to understand how NK cell activity is regulated is often complicated (Vitale M, Sivori S, Pende D, Augugliaro R, di Donato C, Amoroso A et al. "Physical and functional independency of p70 and p58 natural killer (NK) cell receptors for HLA class I: their role in the definition of different groups of alloreactive NK cell clones". Proc Natl Acad Sci USA 1996; 93: 1453-1457). At steady state, the inhibitory receptors (KIRs and CD94/NKG2A/B), which bind to various MHC-I molecules present on almost all cell types, inhibit NK cell activation and prevent NK cell-mediated killing. Under stress conditions, cells downregulate MHC-I expression, causing NK cells to lose inhibitory signaling and be activated in a process called 'missing-self recognition'.

During tumor progression, tumor cells develop several mechanisms to either escape from NK-cell recognition and attack or to induce defective NK cells. These include losing expression of adhesion molecules, costimulatory ligands or ligands for activating receptors, upregulating MHC class I, soluble MIC, FasL or NO expression, secreting immunosuppressive factors such as IL-10, TGF-β and indoleamine 2,3-dioxygense (IDO) and resisting Fas- or perforin-mediated apoptosis Waldhauer I, Steinle A. "NK cells and cancer immunosurveillance". Oncogene 2008; 27: 5932-5943; Maki G, Krystal G, Dougherty G, Takei F, Klingemann H G. "Induction of sensitivity to NK-mediated cytotoxicity by TNF-alpha treatment: possible role of ICAM-3 and CD44". Leukemia 1998; 12: 1565-1572; Costello R T, Sivori S, Marcenaro E, Lafage-Pochitaloff M, Mozziconacci M J, Reviron D et al. «Defective expression and function of natural killer cell-triggering receptors in patients with acute myeloid leukemia". Blood 2002; 99: 3661-3667). Whether enhanced cytotoxicity occurred due to an increase in expression of NK cell activating receptors or was the consequence of expanded NK cells having increased levels of molecules that induce tumor aptotosis (ie., TRAIL, FasL, granzymes, etc) is unclear (Childs R W, Berg M, 2013, "Bringing natural killer cells to the clinic: ex vivo manipulation", Hematology Am Soc Hematol Educ Program.; 2013:234-46).

In cancer patients, NK cell abnormalities have been observed, including decreased cytotoxicity, defective expression of activating receptors or intracellular signaling molecules, overexpression of inhibitory receptors, defective proliferation, decreased numbers in peripheral blood and in tumor infiltrate, and defective cytokine production (Sutlu T, Alici E. "Natural killer cell-based immunotherapy in cancer: current insights and future prospects". J Intern Med 2009; 266: 154-181). Given that NK cells play critical roles in the first-line of defense against malignancies by direct and indirect mechanisms, the therapeutic use of NK cells in human cancer immunotherapy has been proposed and followed in a clinical context.

Among the NK based immunotherapies currently tested for malignant diseases, some of them consist to inject autologous NK cells after their stimulation with cytokines in vivo; to inject allogeneic NK cells after stimulation by compounds such as IL-15/hydrocortisone; to inject NK cells via antibody-dependent cell mediated cytotoxicity or to inject NK cell lines after ex vivo expansion. NK cells are short-lived effectors cells, so there is a need to improve their life span.

Several clinical trials have been realized based on adoptive transfer after genetic modification of NK cells: either by cytokine transgene or overexpression of activating receptors (Nagashima S, Mailliard R, Kashii Y, Reichert T E, Herberman R B, Robbins P et al. "Stable transduction of the interleukin-2 gene into human natural killer cell lines and their phenotypic and functional characterization in vitro and in vivo." Blood 1998; 91: 3850-3861; Zhang J, Sun R, Wei H, Tian Z. "Characterization of interleukin-15 gene-modified human natural killer cells: implications for adoptive cellular immunotherapy. Haematologica" 2004; 89: 338-347); or by silencing of inhibitory receptors by RNA interference (Figueiredo C, Seltsam A, Blasczyk R. 2009, «Permanent silencing of NKG2A expression for cell-based therapeutics. J Mol Med (Berl). 2009 February; 87(2):199-210), or by retargeting NK cells using a chimeric receptor (Muller T, Uherek C, Maki G, Chow K U, Schimpf A, Klingemann H G et al. "Expression of a CD20-specific chimeric antigen receptor enhances cytotoxic activity of NK cells and overcomes NK-resistance of lymphoma and leukemia cells". Cancer Immunol Immunother 2008; 57: 411-423).

From these clinical trials, it appears that only modest clinical success has been achieved so far using NK cell-based therapies in cancer patients. In particular, there is a need to improve functionality of NK cells, and in particular their cytotoxicity/cytolytic activity.

The present invention aims to reach this objective by genetically engineering NK cells to be used in immunotherapy in order to enhance their functional potential (cytotoxicity, drug resistance, engraftment . . . ). Particularly, one goal of the inventors is to obtain a more stabilized and permanent modification of gene expression in order to boost the NK cell toxicity towards cancerous cells.

SUMMARY OF THE INVENTION

The above need is addressed, according to the present invention, by engineering NK cell in such a way that their functionality is improved in a permanent manner, i.e by using specific endonuclease. This gene modification in NK cells is more particularly focused on their cytotoxicity towards tumor cells, their sensitivity to drug, their engraftment potential, which allow for a more efficient and durable response against tumors.

According to the main aspect, the present invention provides with methods for achieving gene editing in NK cells using rare-cutting endonucleases, thereby allowing improving functionality of said cells as part of an immunotherapy.

Basically, this method can be summarized by a) Providing NK cells, especially from donors or patients b) Reducing or inactivating the expression of at least one gene in said NK cell by the use of a specific endonuclease, which expression is reported to diminish or inhibit cytotoxicity/cytolytic activity of NK cells against pathologic cells, in particular malignant cells.

This method is preferably performed as part of an ex-vivo procedure. It aims to improve the functionality of NK cells in their diverse roles as observed in-vivo or in-vitro in the literature, such as:

- promoting antitumor immunotherapy (cytotoxic or cytolytic activity);
- as regulatory cells engaged in reciprocal interactions with other immune cells (such as immune checkpoints);
- their role in improving hematopoietic and solid organ transplantation (engraftment),
- in case of concomitant drug administration to a patient, the above functions can be still preserved by render NK cells less sensitive to said drug.

According to particular embodiments, the specific rare-cutting endonuclease is chosen among TAL-nuclease (ex: TALEN®), meganuclease, zing-finger nuclease (ZFN), RNA guided endonuclease (ex: CRISPR and Cpf1) and MegaTALs, DNA guided endonucleases (ex: Argonaute).

Preferably, said specific endonuclease is a TAL-nuclease, a RNA-guided endonucleases such as Cas9 or Argonaute.

According to one embodiment, cytotoxicity or cytolytic activity of NK cell is enhanced, preferably by reducing or inactivating the expression of at least one gene selected in the group consisting of those regulating or encoding for TGF-β receptor, Cbl-B, A2A receptor, KLRD1, LIR1/ILT2, KIRs, CD94, AhR, Tim-3, Tyro-3, GCN2 and CD94, and more preferably among TGF-β receptor, Cbl-B and A2A receptor.

According to still another embodiment, engraftment of NK cell in host organism is enhanced, preferably by inactivating the gene encoding the protein CD74.

According to still another embodiment, NK cell is rendered less sensitive to drug, preferably by reducing or inactivating the expression of a gene selected in the group consisting of those regulating or encoding for cyclophilin A, TBL1XR1, HPRT, dCK and CD52.

According to still another embodiment, NK cell is rendered less sensitive to immune checkpoints, preferably by reducing or inactivating the expression of the gene encoding for PD-1.

According to still another embodiment, a double gene inhibition or inactivation is performed, wherein said 2 genes to be inactivated are chosen among TGF-β receptor, Cbl-B, A2A receptor, KLRD1, LIR1/ILT2, KIRs, CD94, AhR, Tim-3, Tyro-3, GCN2, CD94, cyclophilin A, TBL1XR1, HPRT, dCK, CD52 and PD-1.

According to another particular embodiment, at least one additional genetic modification of said NK cells to enhance their cytotoxicity/cytolytic function is performed by the expression of at least one gene chosen among IL2 receptor (CD25), IL15-2A-IL15 receptor, anti-CD16 CAR, INFγ, Lysteria P60, TNF and IL12-α.

According to still another particular embodiment, at least one additional genetic modification of said NK cells to enhance their engraftment in organism host is performed by the expression of at least one gene chosen among those encoding the enzymes ALDH, MGMT, MTX, GST and cytidine desaminase.

According to another embodiment, the NK cell engineering method further comprises the step of:

c) introducing into said NK cell an exogenous nucleic acid molecule comprising a nucleotide sequence coding for a Chimeric Antigen Receptor (CAR) directed against at least one antigen expressed at the surface of a malignant or infected cell.

CARs have been extensively described in the literature, in particular under single-chain [Jena, B., G. Dotti, et al. (2010). "Redirecting T-cell specificity by introducing a tumor-specific chimeric antigen receptor." Blood 116(7): 1035-44] and multi-chain forms (WO2014039523).

According to another embodiment, the NK cell engineering method of the invention further comprises the step of:

d) expanding the resulting engineered NK cell to form a therapeutic composition.

It is understood that the details given herein with respect to one aspect of the invention also apply to any of the other aspects of the invention.

DETAILED DESCRIPTION OF THE INVENTION

Figure 1A:
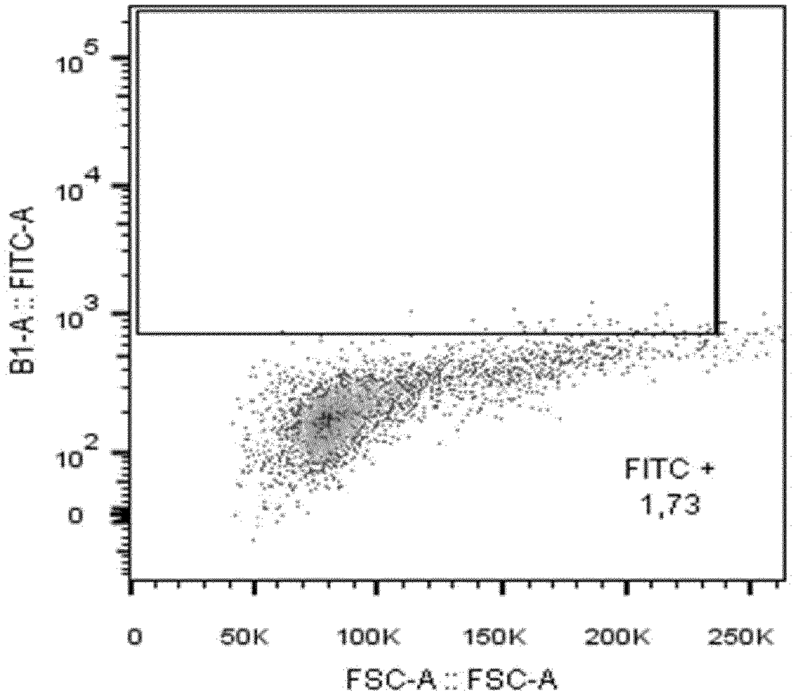
FIG. 1: FACS results obtained 72 hours after NK cell transfection: the upper panel (FIG. 1A) represents the negative control (no RNA), and the lower panel (FIG. 1B) represents transfection using 5 μg of GFP RNA; 2.5 $10^6$ of NK cells were used in each case.

Unless specifically defined herein, all technical and scientific terms used have the same meaning as commonly understood by a skilled artisan in the fields of gene therapy, biochemistry, genetics, and molecular biology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail. Further, the materials, methods, and examples are illustrative only and are not intended to be limiting, unless otherwise specified.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, N.Y.: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

In a general aspect, the present invention relates to methods for new adoptive immunotherapy strategies in treating cancer and infections.

In contrast to the prior art wherein tumor cytotoxicity NK cell is enhanced transiently, the present inventors have designed a method wherein the cell signaling through inhibitory receptors such as KIR or NKG2A is disrupted in a permanent manner. This aspect is particularly important as the technical and financial challenges remain high in manipulating NK cell for immunotherapy, in terms of, for instance, their low numbers in total blood or the low capacity of their expansion.

The present invention relates to a method for improving therapeutic activity of NK cell comprising the steps of:

e) Providing NK cell;
f) Inactivating in said NK cell at least one gene involved in cytotoxicity, provided that this reduction or inhibition of gene expression is not made transient such as by siRNA.

In particular, said reduction or inhibition of gene expression is performed by using specific endonuclease. Although short interfering (si)RNAs have proven to be very potent inhibitors of gene expression and have allowed for the elucidation and better understanding of gene functions in many different cell lines and organisms, there are several limitations to siRNA-knockdown technology (Derek M. Dykxhoorn, Carl D. Novina and Phillip A. Sharp; 2003, "Limitations of gene silencing by transfected siRNA" Nature Reviews Molecular Cell Biology 4, 457-467). The nature of the response is transient; the transduction of siRNA into cells leads to only a transient knockdown of the gene of interest. Another drawback of siRNA is that the effects on gene expression are dependent upon siRNA concentration (Persengiev S P, Zhu X, Green M R, 2004, "Nonspecific, concentration-dependent stimulation and repression of mammalian gene expression by small interfering RNAs (siRNAs)", RNA, 10(1):12-8).

More particularly, the method according to the present invention aims to improve the functionality of a NK cell, which can be expressed as therapeutic activity, comprising the steps of:

a) Providing NK cell;
b) Reducing or inhibiting the gene expression by use of a specific endonuclease in said NK cell of at least one gene selected in the group consisting of those encoding for TGF-β receptor, Cbl-B, A2A receptor, KLRD1, LIR1/ILT2, KIRs, AhR, Tim-3, Tyro-3, GCN2, CD94, CD74, cyclophilin A, TBL1XR1, HPRT, dCK, CD5 and PD-1.

DEFINITIONS

By "functionality of NK cells", i.e referring to "therapeutic activity"; it is meant their diverse roles including in:

- promoting antitumor immunotherapy (cytotoxic or cytolytic activity);
- as regulatory cells engaged in reciprocal interactions with other immune cells (such as immune checkpoints). It has been shown in Concha-Benavente et al 2015 Journal for ImmunoTherapy of Cancer, 3 (Suppl 2):P398 that blocking the PD-1 activity, such as by locking PD-L1/PD-1 axis, may be a useful approach to reverse immune evasion of HNC tumors to cetuximab therapy by reversing NK cell dysfunction;
- their role in improving hematopoietic and solid organ transplantation (engraftment);
- in case of concomitant drug administration to a patient, the above functions can be still preserved by render NK cells less sensitive to said drug.

In the sense of the present invention, at least anyone above cited criteria, when fulfilled, is aiming to improve the in vitro and in vivo therapeutic activity of the engineered NK cells such as defined hereafter. By "improvement of therapeutic activity", it is meant that for a pertinent test as outlined thereafter, more than 25%, at least 30%, at least 40%, at least 50%, at least 65%, at least 75%, at least 85%, at least 95%, or at least 99% for the tested criteria is obtained by using engineered NK cells of the invention when compared to that obtained by using non-engineered NK cells.

By "cytotoxicity", it is intended the extent of the destructive or killing capacity of an agent, in particular it is meant to describe the character of the NK cell activity that limits the development of cancer cells. Cytotoxic potential can be expressed as the percent of target ceil death above background (e.g., without the binding molecule or with an irrelevant binding molecule), using complete target cell death as 100%. In certain aspects, the NK cell engineered accordingly to the invention—preferably endowing a CAR directed against a tumoral antigen-reduces the quantity, number, amount or percentage of targeted cancerous cells by at least 25%, at least 30%, at least 40%, at least 50%, at least 65%, at least 75%, at least 85%, at least 95%, or at least 99% (to undetectable level) in a subject relative to a negative control.

NK cells are naturally endowed with a "cytolytic activity": they are characterized by their ability to initiate an immediate and direct cytolytic response to virally infected or malignantly transformed cells.

Cytotoxicity of the engineered NK cells of the invention may be monitored:

- in vitro assay: by using cytotoxicity such as used currently when T cells are tested; a classical protocol is described in the section "General methods" thereafter;
- In vivo assay: by using for instance the tumor challenge test in mammals such as mice, for instance disclosed in Ng S, Yoshida K, Zelikoff J T. 2010 "tumor challenges in immunotoxicity testing", Methods Mol Biol.; 598: 143-55.

Reduction of immune checkpoint activity such as PD-1 may be monitored:

- in vitro assay: cytotoxicity or serial killing assay may be used (Bhat R and Watzl C 2007 "Serial Killing of Tumor Cells by Human Natural Killer Cells—Enhancement by Therapeutic Antibodies", PLoS ONE.; 2(3);
- In vivo assay: survival curve with tumor-expressing mammals such as mice may be used (Valiathan C and McFaline J L, 2011, "A Rapid Survival Assay to Measure Drug-Induced Cytotoxicity and Cell Cycle Effects" DNA Repair (Amst). PMC 2013 Jan. 2)

Improvement of engraftment may be monitored:

- In vitro assay such as by using mixed lymphocyte reaction (MLR); as described for instance in Bromelow K V, Hirst W, Mendes R L, Winkley A R, Smith I E, O'Brien M E, Souberbielle B E. 2001 "Whole blood assay for assessment of the mixed lymphocyte reaction" J Immunol Methods. January 1; 247(1-2):1-8.;
- In vivo assay by monitoring the survival length of mammals, such as in mice, when they have been injected by allogeneic engineered NK cells.

Conferring drug resistance may be monitored when NK cells are engineered at least to have a specific gene disrupted as to provide a resistance to a particular drug:

- In vitro assay by assessing IC50 by contacting said engineered NK cells with a series of different amounts of the drug and evaluating their survival rate i.e determination of IC50 or slope of the dose-response curve. Such routine test can be performed according, i.e. to WO201575195;
- In vivo assay by using survival rate in mammals, ie mice, when different amounts of drug are administrated to them.

Inactivation by Specific Rare-Cutting Endonucleases

By inactivating a gene it is intended that the gene of interest is not expressed in a functional protein form. In particular embodiment, the genetic modification of the method relies on the expression, in provided cells to engineer, of one rare-cutting endonuclease such that said rare-cutting endonuclease specifically catalyzes cleavage in one targeted gene thereby inactivating said targeted gene. The nucleic acid strand breaks caused by the rare-cutting endonuclease are commonly repaired through the distinct mechanisms of homologous recombination or non-homologous end joining (NHEJ). However, NHEJ is an imperfect repair process that often results in changes to the DNA sequence at the site of the cleavage. Mechanisms involve rejoining of what remains of the two DNA ends through direct re-ligation (Critchlow and Jackson 1998) or via the so-called microhomology-mediated end joining (Ma, Kim et al. 2003). Repair via non-homologous end joining (NHEJ) often results in small insertions or deletions and can be used for the creation of specific gene knockouts. Said modification may be a substitution, deletion, or addition of at least one nucleotide. Cells in which a cleavage-induced mutagenesis event—i.e a mutagenesis event consecutive to an NHEJ event—has occurred can be identified and/or selected by well-known method in the art.

By inactivating a gene it is intended that the gene of interest is not expressed in a functional protein form. It is understood that "gene silencing" is not encompassed in the scope of the present invention. In particular embodiment, the genetic modification of the method relies on the expression, in provided cells to engineer, of one rare-cutting endonuclease such that said rare-cutting endonuclease specifically catalyzes cleavage in one targeted gene thereby inactivating said targeted gene. The nucleic acid strand breaks caused by the rare-cutting endonuclease are commonly repaired through the distinct mechanisms of homologous recombination or non-homologous end joining (NHEJ). However, NHEJ is an imperfect repair process that often results in changes to the DNA sequence at the site of the cleavage. Mechanisms involve rejoining of what remains of the two DNA ends through direct re-ligation (Critchlow and Jackson 1998) or via the so-called microhomology-mediated end joining (Ma, Kim et al. 2003). Repair via non-homologous end joining (NHEJ) often results in small insertions or deletions and can be used for the creation of specific gene knockouts. Said modification may be a substitution, deletion, or addition of at least one nucleotide. Cells in which a cleavage-induced mutagenesis event, i.e a mutagenesis event consecutive to an NHEJ event, has occurred can be identified and/or selected by well-known method in the art.

By "reducing the expression of a gene", it is intended that the inactivation is not complete but partially. In this case, the specific rare cutting endonuclease produces some break(s) in the gene, which may still allow the production of a truncated mRNA and a shorter polypeptide. Consequently, it may still remain some activity of the gene within engineered NK cell, but not enough to produce a significant effect inside said NK cell.

Endonucleolytic breaks are known to stimulate the rate of homologous recombination. Thus, in another embodiment, the genetic modification step of the method further comprises a step of introduction into cells an exogeneous nucleic acid comprising at least a sequence homologous to a portion of the target nucleic acid sequence, such that homologous recombination occurs between the target nucleic acid sequence and the exogeneous nucleic acid. In particular embodiments, said exogenous nucleic acid comprises first and second portions which are homologous to region 5' and 3' of the target nucleic acid sequence, respectively. Said exogenous nucleic acid in these embodiments also comprises a third portion positioned between the first and the second portion which comprises no homology with the regions 5' and 3' of the target nucleic acid sequence. Following cleavage of the target nucleic acid sequence, a homologous recombination event is stimulated between the target nucleic acid sequence and the exogenous nucleic acid. Preferably, homologous sequences of at least 50 bp, preferably more than 100 bp and more preferably more than 200 bp are used within said donor matrix. Therefore, the exogenous nucleic acid is preferably from 200 bp to 6000 bp, more preferably from 1000 bp to 2000 bp. Indeed, shared nucleic acid homologies are located in regions flanking upstream and downstream the site of the break and the nucleic acid sequence to be introduced should be located between the two arms.

According to a preferred embodiment, the reduction or inactivation of gene expression is preferably performed by using a TAL-nuclease, meganuclease, zing-finger nuclease (ZFN), or RNA/DNA guided endonuclease, such as Cas9 or Argonaute.

According to a more preferred embodiment, the reduction or inactivation of gene expression of at least one gene to improve functionality of a NK cell is performed by using TALE-nucleases. In an even more preferred embodiment, said gene is chosen among TGF-β receptor, Cbl-B, A2A receptor, KLRD1, LIR1/ILT2, KIRs, AhR, Tim-3, Tyro-3, GCN2, CD94, CD74, cyclophilin A, TBL1XR1, HPRT, dCK, CD5 and PD-1.

This can be accomplished at a precise genomic location targeted by a specific TALE-nuclease, wherein said specific TALE-nuclease catalyzes a cleavage and wherein said exogenous nucleic acid successively comprising at least a region of homology and a sequence to inactivate one targeted gene selected from the group previously cited. Several genes can be, successively or at the same time, inactivated by using several TALE-nucleases respectively and specifically targeting one defined gene and several specific. By TALE-nuclease is intended a fusion protein consisting of a DNA-binding domain derived from a Transcription Activator Like Effector (TALE) and one nuclease catalytic domain to cleave a nucleic acid target sequence. (Boch, Scholze et al. 2009; Moscou and Bogdanove 2009; Christian, Cermak et al. 2010; Cermak, Doyle et al. 2011; Geissler, Scholze et al. 2011; Huang, Xiao et al. 2011; Li, Huang et al. 2011; Mahfouz, Li et al. 2011; Miller, Tan et al. 2011; Morbitzer, Romer et al. 2011; Mussolino, Morbitzer et al. 2011; Sander, Cade et al. 2011; Tesson, Usal et al. 2011; Weber, Gruetzner et al. 2011; Zhang, Cong et al. 2011; Deng, Yan et al. 2012; Li, Piatek et al. 2012; Mahfouz, Li et al. 2012; Mak, Bradley et al. 2012).

According to another preferred embodiment, the reduction or inactivation of gene expression of at least one gene to improve functionality of a NK cell is performed by RNA-guided endonuclease such as Cas9 or DNA-guided endonuclease, such as Argonaute based techniques as described in WO2014189628.

In a preferred embodiment, the gene which expression is to be reduced or inactivated is chosen among TGF-β receptor, Cbl-B, A2A receptor, KLRD1, LIR1/ILT2, KIRs, AhR, Tim-3, Tyro-3, GCN2, CD94, CD74, cyclophilin A, TBL1XR1, HPRT, dCK, CD5 and PD-1.

In the present invention new TALE-nucleases have been designed for precisely targeting relevant genes for adoptive immunotherapy strategies. Preferred TALE-nucleases according to the invention are those recognizing and cleaving the target sequence selected from the group consisting of SEQ ID NO: 1, 4, 7 for inactivation of respectively the TGFbeta and the Cbl-b genes (exon 2 and exon 3). Also, other preferred TALE-nucleases according to the invention are from the group consisting of SEQ ID NO: 21-22, 24-25 and 27-28 recognizing and cleaving the human beta2M gene of sequences SEQ ID NO.20, 23 or 26 respectively.

Beta-2 microglobulin, also known as B2M, is the light chain of MHC class I molecules, and as such an integral part of the major histocompatibility complex In human, B2M is encoded by the b2m gene which is located on chromosome 15, opposed to the other MHC genes which are located as gene cluster on chromosome 6. The human protein is composed of 119 amino acids (SEQ ID NO: 29) and has a molecular weight of 11.800 Daltons. Mice models deficient for beta-2 microglobulin have shown that B2M is necessary for cell surface expression of MHC class I and stability of the peptide binding groove. It was further shown that haemopoietic transplants from mice that are deficient for normal cell-surface MHC I expression are rejected by NK1.1+ cells in normal mice because of a targeted mutation in the beta-2 microglobulin gene, suggesting that deficient expression of MHC I molecules renders marrow cells susceptible to rejection by the host immune system (Bix M. et al, 1991, *Nature* 349(6307):329-31).

In the following are presented a list of diverse gene which expression is to be reduced or inactivated in order to enhance NK cell functions such as their cytotoxic/cytolytic, or confer drug resistance or enhance their engraftment in host organism.

It is well understood that the present invention encompasses the inactivation of at least one gene involved in the enhancement of NK cell function, so includes also a combination of double genetic inactivation.

The present invention aims particularly to provide a method for improving therapeutic activity of a NK cell comprising the steps of:

a) Providing NK cell;

b) Reducing or inactivating the expression of a gene into NK cell by using a specific endonuclease said gene is selected in the group consisting of those encoding for TGF-β receptor, Cbl-B, A2A receptor, KLRD1, LIR1/ILT2, KIRs, AhR, Tim-3, Tyro-3, GCN2, CD94, CD74, cyclophilin A, TBL1XR1, HPRT, dCK, CD5 and PD-1.

In a preferred embodiment, said above gene is involved in promoting antitumor immunotherapy by improving cytotoxic or cytolytic activity and is selected in the group consisting of those encoding for TGF-β receptor, Cbl-B, A2A receptor, KLRD1, LIR1/ILT2, KIRs, AhR, Tim-3, Tyro-3, GCN2, CD94, CD74, cyclophilin A and PD-1.

In another preferred embodiment, said above gene is involved in improving hematopoietic cell transplant engraftment and is Beta2M, preferably of SEQ ID NO.29.

In still another preferred embodiment, said above gene is involved in rendering said NK cell less sensitive to a drug when the latter is concomitantly administrated to a patient and said gene is selected in the group consisting of those encoding for TBL1XR1, HPRT, dCK and CD5.

Enhancement of Cytotoxic/Cytolytic Function

According to one embodiment, the method of the invention encompasses the inactivation of at least one gene among the NK receptors: NKG2A, LIR1/ILT2, KIR family members including KIR2DL1-3 and KIR2DL4, PD1, Cbl-b, A2A receptor (ADORA2A), TAM receptors (Tyro/AXL/MER), TGFbeta receptor, CXCR2, CXCR4 and CXCR7, CD94, CD74, FAS, AHR Aryl hydrocarbon receptor, GCN2, cyclophyline and TIM-3R (NK cell immunoglobulin- and mucin domain-containing 3 receptor).

According to one preferred embodiment, the gene involved in the cytolytic activity to be inactivated, or which gene expression is to be reduced, is the one encoding for the TGF-β receptor. Transforming growth factor beta (TGF-β) receptor a secreted protein (in human UniProt: P36897 and RefSeq: NM_ 001130916.1). The protein encoded by this gene forms a heteromeric complex with type II TGF-beta receptors when bound to TGF-beta, transducing the TGFbeta signal from the cell surface to the cytoplasm. In some studies, it has been shown that TGF-beta on Treg binds to TGF-beta receptor expressed by NK cells and suppress their cytotoxic function towards tumor cells (Wan' Y Y and Flavell R A, 2007, "'Yin-Yang' functions of TGF-β and Tregs in immune regulation", Immunol Rev., 220:199-213).

According to a specific embodiment, the TGF-β gene is inactivated by the use of TALE-nuclease, and preferably by nucleic acids encoding the TALENs which share at least 80%, more preferably 90% and even more preferably 95% of identity with SEQ ID No: 2-3 such as presented in Table 1.

TABLE 1

Nucleic acid and polynucleotide sequences for the TGF-β and Beta2M targets and the pairs of corresponding TALENs for the inactivation of said genes.

| Name | SEQ ID NO. | Nucleic acid or polynucleotide sequence |
|---|---|---|
| TGF-B Exon 2 target | 1 | TTGAGCTGGACACCCTGGTGGGGAAAGGTCGCTTTGCTGAGGTCTATAA |
| Left Talen | 2 | MGDPKKKRKVIDYPYDVPDYAIDIADLRTLGYSQQQQEKIKPKVRSTVAQHHEALVGH<br>GFTHAHIVALSQHPAALGTVAVKYQDMIAALPEATHEAIVGVGKQWSGARALEALLTV<br>AGELRGPPLQLDTGQLLKIAKRGGVTAVEAVHAWRNALTGAPLNLTPQQVVAIASNG<br>GGKQALETVQRLLPVLCQAHGLTPQQVVAIASNNGGKQALETVQRLLPVLCQAHGLTP<br>EQVVAIASNIGGKQALETVQALLPVLCQAHGLTPQQVVAIASNNGGKQALETVQRLLP<br>VLCQAHGLTPEQVVAIASHDGGKQALETVQRLLPVLCQAHGLTPQQVVAIASNGGGK<br>QALETVQRLLPVLCQAHGLTPQQVVAIASNNGGKQALETVQRLLPVLCQAHGLTPQQ<br>VVAIASNNGGKQALETVQRLLPVLCQAHGLTPEQVVAIASNIGGKQALETVQALLPVLC<br>QAHGLTPEQVVAIASHDGGKQALETVQRLLPVLCQAHGLTPEQVVAIASNIGGKQALE<br>TVQALLPVLCQAHGLTPEQVVAIASHDGGKQALETVQRLLPVLCQAHGLTPEQVVAIAS<br>HDGGKQALETVQRLLPVLCQAHGLTPEQVVAIASHDGGKQALETVQRLLPVLCQAHGL<br>TPQQVVAIASNGGGKQALETVQRLLPVLCQAHGLTPQQVVAIASNGGGRPALESIVAQ<br>LSRPDPALAALTNDHLVALACLGGRPALDAVKKGLGDPISRSQLVKSELEEKKSELRHKL<br>KYVPHEYIELIEIARNSTQDRILEMKVMEFFMKVYGYRGKHLGGSRKPDGAIYTVGSPID<br>YGVIVDTKAYSGGYNLPIGQADEMQRYVEENQTRNKHINPNEWWKVYPSSVTEFKFLF<br>VSGHFKGNYKAQLTRLNHITNCNGAVLSVEELLIGGEMIKAGTLTLEEVRRKFNNGEINF<br>AAD<br>DNA binding domain RVDs: NG-NN-NI-NN-HD-NG-NN-NN-NI-HD-NI-HD-HD-<br>HD-NG-NG |
| Right Talen | 3 | MGDPKKKRKVIDYPYDVPDYAIDIADLRTLGYSQQQQEKIKPKVRSTVAQHHEALVGH<br>GFTHAHIVALSQHPAALGTVAVKYQDMIAALPEATHEAIVGVGKQWSGARALEALLTV<br>AGELRGPPLQLDTGQLLKIAKRGGVTAVEAVHAWRNALTGAPLNLTPQQVVAIASNG<br>GGKQALETVQRLLPVLCQAHGLTPEQVVAIASNIGGKQALETVQALLPVLCQAHGLTP<br>QQVVAIASNGGGKQALETVQRLLPVLCQAHGLTPEQVVAIASNIGGKQALETVQALLP<br>VLCQAHGLTPQQVVAIASNNGGKQALETVQRLLPVLCQAHGLTPEQVVAIASNIGGKQ<br>ALETVQALLPVLCQAHGLTPEQVVAIASHDGGKQALETVQRLLPVLCQAHGLTPEQVV<br>AIASHDGGKQALETVQRLLPVLCQAHGLTPQQVVAIASNGGGKQALETVQRLLPVLCQ<br>AHGLTPEQVVAIASHDGGKQALETVQRLLPVLCQAHGLTPEQVVAIASNIGGKQALET<br>VQALLPVLCQAHGLTPQQVVAIASNNGGKQALETVQRLLPVLCQAHGLTPEQVVAIAS<br>HDGGKQALETVQRLLPVLCQAHGLTPEQVVAIASNIGGKQALETVQALLPVLCQAHGL<br>TPEQVVAIASNIGGKQALETVQALLPVLCQAHGLTPQQVVAIASNGGGRPALESIVAQL<br>SRPDPALAALTNDHLVALACLGGRPALDAVKKGLGDPISRSQLVKSELEEKKSELRHKLK<br>YVPHEYIELIEIARNSTQDRILEMKVMEFFMKVYGYRGKHLGGSRKPDGAIYTVGSPIDY<br>GVIVDTKAYSGGYNLPIGQADEMQRYVEENQTRNKHINPNEWWKVYPSSVTEFKFLF<br>VSGHFKGNYKAQLTRLNHITNCNGAVLSVEELLIGGEMIKAGTLTLEEVRRKFNNGEINF<br>AAD<br>DNA binding domain RVDs: NG-NI-NG-NI-NN-NI-HD-HD-NG-HD-NI-NN-HD-NI-<br>NI-NG |
| Beta2M target 1 | 20 | TCTCGCTCCGTGGCCTTAGCTGTGCTCGCGCTACTCTCTCTTTCTGGCCTGGAGGCTA |
| Left TALEN | 21 | MGDPKKKRKVIDYPYDVPDYAIDIADLRTLGYSQQQQEKIKPKVRSTVAQHHEALVGH<br>GFTHAHIVALSQHPAALGTVAVKYQDMIAALPEATHEAIVGVGKQWSGARALEALLTV<br>AGELRGPPLQLDTGQLLKIAKRGGVTAVEAVHAWRNALTGAPLNLTPQQVVAIASNN<br>GGKQALETVQRLLPVLCQAHGLTPQQVVAIASNNGGKQALETVQRLLPVLCQAHGLTP<br>EQVVAIASHDGGKQALETVQRLLPVLCQAHGLTPEQVVAIASHDGGKQALETVQRLLP<br>VLCQAHGLTPQQVVAIASNGGGKQALETVQRLLPVLCQAHGLTPQQVVAIASNGGGK<br>QALETVQRLLPVLCQAHGLTPEQVVAIASNIGGKQALETVQALLPVLCQAHGLTPQQV<br>VAIASNNGGKQALETVQRLLPVLCQAHGLTPEQVVAIASHDGGKQALETVQRLLPVLC<br>QAHGLTPQQVVAIASNGGGKQALETVQRLLPVLCQAHGLTPQQVVAIASNNGGKQAL<br>ETVQRLLPVLCQAHGLTPQQVVAIASNGGGKQALETVQRLLPVLCQAHGLTPQQVVAI<br>ASNNGGKQALETVQRLLPVLCQAHGLTPEQVVAIASHDGGKQALETVQRLLPVLCQA<br>HGLTPQQVVAIASNGGGKQALETVQRLLPVLCQAHGLTPQQVVAIASNGGGRPALESI<br>VAQLSRPDPALAALTNDHLVALACLGGRPALDAVKKGLGDPISRSQLVKSELEEKKSELR<br>HKLKYVPHEYIELIEIARNSTQDRILEMKVMEFFMKVYGYRGKHLGGSRKPDGAIYTVGS<br>PIDYGVIVDTKAYSGGYNLPIGQADEMQRYVEENQTRNKHINPNEWWKVYPSSVTEFK<br>FLFVSGHFKGNYKAQLTRLNHITNCNGAVLSVEELLIGGEMIKAGTLTLEEVRRKFNNGE<br>INFAAD |

TABLE 1-continued

Nucleic acid and polynucleotide sequences for the TGF-β and Beta2M targets and the pairs of corresponding TALENs for the inactivation of said genes.

| Name | SEQ ID NO. | Nucleic acid or polynucleotide sequence |
|---|---|---|
| Right TALEN | 22 | MGDPKKKRKVIDKETAAAKFERQHMDSIDIADLRTLGYSQQQQEKIKPKVRSTVAQHH<br>EALVGHGFTHAHIVALSQHPAALGTVAVKYQDMIAALPEATHEAIVGVGKQWSGARA<br>LEALLTVAGELRGPPLQLDTGQLLKIAKRGGVTAVEAVHAWRNALTGAPLNLTPEQVV<br>AIASNIGGKQALETVQALLPVLCQAHGLTPQQVVAIASNNGGKQALETVQRLLPVLCQ<br>AHGLTPEQVVAIASHDGGKQALETVQRLLPVLCQAHGLTPEQVVAIASHDGGKQALET<br>VQRLLPVLCQAHGLTPQQVVAIASNGGGKQALETVQRLLPVLCQAHGLTPEQVVAIAS<br>HDGGKQALETVQRLLPVLCQAHGLTPEQVVAIASHDGGKQALETVQRLLPVLCQAHGL<br>TPEQVVAIASNIGGKQALETVQALLPVLCQAHGLTPQQVVAIASNNGGKQALETVQRL<br>LPVLCQAHGLTPQQVVAIASNNGGKQALETVQRLLPVLCQAHGLTPEQVVAIASHDGG<br>KQALETVQRLLPVLCQAHGLTPEQVVAIASHDGGKQALETVQRLLPVLCQAHGLTPEQ<br>VVAIASNIGGKQALETVQALLPVLCQAHGLTPQQVVAIASNNGGKQALETVQRLLPVLC<br>QAHGLTPEQVVAIASNIGGKQALETVQALLPVLCQAHGLTPQQVVAIASNGGGRPALE<br>SIVAQLSRPDPALAALTNDHLVALACLGGRPALDAVKKGLGDPISRSQLVKSELEEKKSEL<br>RHKLKYVPHEYIELIEIARNSTQDRILEMKVMEFFMKVYGYRGKHLGGSRKPDGAIYTVG<br>SPIDYGVIVDTKAYSGGYNLPIGQADEMQRYVEENQTRNKHINPNEWWKVYPSSVTEF<br>KFLFVSGHFKGNYKAQLTRLNHITNCNGAVLSVEELLIGGEMIKAGTLTLEEVRRKFNNG<br>EINFAAD |
| Beta2M target 2 | 23 | TCCAAAGATTCAGGTTTACTCACGTCATCCAGCAGAGAATGGAAAGTCAA |
| Left TALEN | 24 | MGDPKKKRKVIDYPYDVPDYAIDIADLRTLGYSQQQQEKIKPKVRSTVAQHHEALVGH<br>GFTHAHIVALSQHPAALGTVAVKYQDMIAALPEATHEAIVGVGKQWSGARALEALLTV<br>AGELRGPPLQLDTGQLLKIAKRGGVTAVEAVHAWRNALTGAPLNLTPEQVVAIASHDG<br>GKQALETVQRLLPVLCQAHGLTPEQVVAIASHDGGKQALETVQRLLPVLCQAHGLTPE<br>QVVAIASNIGGKQALETVQALLPVLCQAHGLTPEQVVAIASNIGGKQALETVQALLPVL<br>CQAHGLTPEQVVAIASNIGGKQALETVQALLPVLCQAHGLTPQQVVAIASNNGGKQAL<br>ETVQRLLPVLCQAHGLTPEQVVAIASNIGGKQALETVQALLPVLCQAHGLTPQQVVAIA<br>SNGGGKQALETVQRLLPVLCQAHGLTPQQVVAIASNGGGKQALETVQRLLPVLCQAH<br>GLTPEQVVAIASHDGGKQALETVQRLLPVLCQAHGLTPEQVVAIASNIGGKQALETVQ<br>ALLPVLCQAHGLTPQQVVAIASNNGGKQALETVQRLLPVLCQAHGLTPQQVVAIASNN<br>GGKQALETVQRLLPVLCQAHGLTPQQVVAIASNGGGKQALETVQRLLPVLCQAHGLTP<br>QQVVAIASNGGGKQALETVQRLLPVLCQAHGLTPQQVVAIASNGGGRPALESIVAQLS<br>RPDPALAALTNDHLVALACLGGRPALDAVKKGLGDPISRSQLVKSELEEKKSELRHKLKY<br>VPHEYIELIEIARNSTQDRILEMKVMEFFMKVYGYRGKHLGGSRKPDGAIYTVGSPIDYG<br>VIVDTKAYSGGYNLPIGQADEMQRYVEENQTRNKHINPNEWWKVYPSSVTEFKFLFVS<br>GHFKGNYKAQLTRLNHITNCNGAVLSVEELLIGGEMIKAGTLTLEEVRRKFNNGEINFAA<br>D |
| Right TALEN | 25 | MGDPKKKRKVIDKETAAAKFERQHMDSIDIADLRTLGYSQQQQEKIKPKVRSTVAQHH<br>EALVGHGFTHAHIVALSQHPAALGTVAVKYQDMIAALPEATHEAIVGVGKQWSGARA<br>LEALLTVAGELRGPPLQLDTGQLLKIAKRGGVTAVEAVHAWRNALTGAPLNLTPQQVV<br>AIASNNGGKQALETVQRLLPVLCQAHGLTPEQVVAIASNIGGKQALETVQALLPVLCQA<br>HGLTPEQVVAIASHDGGKQALETVQRLLPVLCQAHGLTPQQVVAIASNGGGKQALET<br>VQRLLPVLCQAHGLTPQQVVAIASNGGGKQALETVQRLLPVLCQAHGLTPQQVVAIAS<br>NGGGKQALETVQRLLPVLCQAHGLTPEQVVAIASHDGGKQALETVQRLLPVLCQAHG<br>LTPEQVVAIASHDGGKQALETVQRLLPVLCQAHGLTPEQVVAIASNIGGKQALETVQAL<br>LPVLCQAHGLTPQQVVAIASNGGGKQALETVQRLLPVLCQAHGLTPQQVVAIASNGG<br>GKQALETVQRLLPVLCQAHGLTPEQVVAIASHDGGKQALETVQRLLPVLCQAHGLTPQ<br>QVVAIASNGGGKQALETVQRLLPVLCQAHGLTPEQVVAIASHDGGKQALETVQRLLPV<br>LCQAHGLTPQQVVAIASNGGGKQALETVQRLLPVLCQAHGLTPQQVVAIASNGGGRP<br>ALESIVAQLSRPDPALAALTNDHLVALACLGGRPALDAVKKGLGDPISRSQLVKSELEEK<br>KSELRHKLKYVPHEYIELIEIARNSTQDRILEMKVMEFFMKVYGYRGKHLGGSRKPDGAI<br>YTVGSPIDYGVIVDTKAYSGGYNLPIGQADEMQRYVEENQTRNKHINPNEWWKVYPS<br>SVTEFKFLFVSGHFKGNYKAQLTRLNHITNCNGAVLSVEELLIGGEMIKAGTLTLEEVRRK<br>FNNGEINFAAD |
| Beta2M target 3 | 26 | TTAGCTGTGCTCGCGCTACTCTCTCTTTCTGGCCTGGAGGCTATCCA |
| Left TALEN | 27 | MGDPKKKRKVIDYPYDVPDYAIDIADLRTLGYSQQQQEKIKPKVRSTVAQHHEALVGH<br>GFTHAHIVALSQHPAALGTVAVKYQDMIAALPEATHEAIVGVGKQWSGARALEALLTV<br>AGELRGPPLQLDTGQLLKIAKRGGVTAVEAVHAWRNALTGAPLNLTPEQVVAIASNIG<br>GKQALETVQALLPVLCQAHGLTPQQVVAIASNNGGKQALETVQRLLPVLCQAHGLTPE<br>QVVAIASHDGGKQALETVQRLLPVLCQAHGLTPQQVVAIASNGGGKQALETVQRLLPV<br>LCQAHGLTPQQVVAIASNNGGKQALETVQRLLPVLCQAHGLTPQQVVAIASNGGGKQ<br>ALETVQRLLPVLCQAHGLTPQQVVAIASNNGGKQALETVQRLLPVLCQAHGLTPEQVV<br>AIASHDGGKQALETVQRLLPVLCQAHGLTPQQVVAIASNGGGKQALETVQRLLPVLCQ<br>AHGLTPEQVVAIASHDGGKQALETVQRLLPVLCQAHGLTPQQVVAIASNNGGKQALE<br>TVQRLLPVLCQAHGLTPEQVVAIASHDGGKQALETVQRLLPVLCQAHGLTPQQVVAIA<br>SNNGGKQALETVQRLLPVLCQAHGLTPEQVVAIASHDGGKQALETVQRLLPVLCQAH<br>GLTPQQVVAIASNGGGKQALETVQRLLPVLCQAHGLTPQQVVAIASNGGGRPALESIV<br>AQLSRPDPALAALTNDHLVALACLGGRPALDAVKKGLGDPISRSQLVKSELEEKKSELRH |

TABLE 1-continued

Nucleic acid and polynucleotide sequences for the TGF-β and Beta2M targets and the pairs of corresponding TALENs for the inactivation of said genes.

| Name | SEQ ID NO. | Nucleic acid or polynucleotide sequence |
|---|---|---|
| | | KLKYVPHEYIELIEIARNSTQDRILEMKVMEFFMKVYGYRGKHLGGSRKPDGAIYTVGSP<br>IDYGVIVDTKAYSGGYNLPIGQADEMQRYVEENQTRNKHINPNEWWKVYPSSVTEFKF<br>LFVSGHFKGNYKAQLTRLNHITNCNGAVLSVEELLIGGEMIKAGTLTLEEVRRKFNNGEI<br>NFAAD |
| Right TALEN | 28 | MGDPKKKRKVIDKETAAAKFERQHMDSIDIADLRTLGYSQQQQEKIKPKVRSTVAQHH<br>EALVGHGFTHAHIVALSQHPAALGTVAVKYQDMIAALPEATHEAIVGVGKQWSGARA<br>LEALLTVAGELRGPPLQLDTGQLLKIAKRGGVTAVEAVHAWRNALTGAPLNLTPQQVV<br>AIASNNGGKQALETVQRLLPVLCQAHGLTPQQVVAIASNNGGKQALETVQRLLPVLCQ<br>AHGLTPEQVVAIASNIGGKQALETVQALLPVLCQAHGLTPQQVVAIASNGGGKQALET<br>VQRLLPVLCQAHGLTPEQVVAIASNIGGKQALETVQALLPVLCQAHGLTPQQVVAIASN<br>NGGKQALETVQRLLPVLCQAHGLTPEQVVAIASHDGGKQALETVQRLLPVLCQAHGLT<br>PEQVVAIASHDGGKQALETVQRLLPVLCQAHGLTPQQVVAIASNGGGKQALETVQRLL<br>PVLCQAHGLTPEQVVAIASHDGGKQALETVQRLLPVLCQAHGLTPEQVVAIASHDGGK<br>QALETVQRLLPVLCQAHGLTPEQVVAIASNIGGKQALETVQALLPVLCQAHGLTPQQV<br>VAIASNNGGKQALETVQRLLPVLCQAHGLTPQQVVAIASNNGGKQALETVQRLLPVLC<br>QAHGLTPEQVVAIASHDGGKQALETVQRLLPVLCQAHGLTPQQVVAIASNGGGRPAL<br>ESIVAQLSRPDPALAALTNDHLVALACLGGRPALDAVKKGLGDPISRSQLVKSELEEKKS<br>ELRHKLKYVPHEYIELIEIARNSTQDRILEMKVMEFFMKVYGYRGKHLGGSRKPDGAIYT<br>VGSPIDYGVIVDTKAYSGGYNLPIGQADEMQRYVEENQTRNKHINPNEWWKVYPSSV<br>TEFKFLFVSGHFKGNYKAQLTRLNHITNCNGAVLSVEELLIGGEMIKAGTLTLEEVRRKF<br>NNGEINFAAD |

According to another preferred embodiment, the gene involved in the cytolytic activity to be inactivated, or which gene expression is to be reduced, is the one encoding for E3 ubiquitin ligase Cbl-b. CBL-B is an E3 ubiquitin-protein ligase (UniProt:Q13191 in human) that in humans is encoded by the CBLB gene (RefSeq: NM_170662; Keane M M, Rivero-Lezcano O M, Mitchell J A, Robbins K C, Lipkowitz S, 1995, "Cloning and characterization of cbl-b: a SH3 binding protein with homology to the c-cbl proto-oncogene". *Oncogene* 10 (12): 2367-77). CBLB is a member of the CBL gene family. In a publication, it is reported that genetic deletion of the E3 ubiquitin ligase Cbl-b (casitas B-lineage lymphoma-b) or targeted inactivation of its E3 ligase activity licenses natural killer (NK) cells to spontaneously reject metastatic tumours (Magdalena Paolino et al., 2014, "The E3 ligase Cbl-b and TAM receptors regulate cancer metastasis via natural killer cells", Nature, 507, 508-512). Some data implicate CBL-B and TAM as negative regulators of NK cell activity and suggest that interfering with this pathway may improve NK cell-mediated tumor surveillance (The E3 ligase Cbl-b and TAM receptors regulate cancer metastasis via natural killer cells. (Paolino M et al. 2014, "TAM Receptor or CBL-B Inhibition Enables Tumor Rejection by NK Cells" Cancer discovery, (4) 389).

According to a specific embodiment, the E3 ubiquitin ligase Cbl-b gene is inactivated, or which gene expression is to be reduced, by the use of TALE-nuclease, and preferably by nucleic acids encoding the TALENs which share at least 80%, more preferably 90% and even more preferably 95% of identity with SEQ ID No: 5-6 and 8-9 in the following Table 2.

TABLE 2

Nucleic acid and polynucleotide sequences for the Exon 2 and Exon 3 Cbl-b targets and the corresponding TALENs for the inactivation of said gene.

| Name | SEQ ID NO. | Polynucleotide sequence |
|---|---|---|
| Cbl-b exon 2 target | 4 | TGTGCCAAAATCCCAAACTTCAGTTGAAAAATAGCCCACCATATA |
| Left Talen | 5 | MGDPKKKRKVIDYPYDVPDYAIDIADPIRSRTPSPARELLPGPQPDGVQPTADRGVSP<br>PAGGPLDGLPARRTMSRTRLPSPPAPSPAFSAGSFSDLLRQFDPSLFNTSLFDSLPPFG<br>AHHTEAATGEWDEVQSGLRAADAPPPTMRVAVTAARPPRAKPAPRRRAAQPSDAS<br>PAAQVDLRTLGYSQQQQEKIKPKVRSTVAQHHEALVGHGFTHAHIVALSQHPAALG<br>TVAVKYQDMIAALPEATHEAIVGVGKOWSGARALEALLTVAGELRGPPLQLDTGOLL<br>KIAKRGGVTAVEAVHAWRNALTGAPLNLTPQQVVAIASNNGGKQALETVQRLLPVL<br>CQAHGLTPQQVVAIASNGGGKQALETVQRLLPVLCQAHGLTPQQVVAIASNNGGK<br>QALETVQRLLPVLCQAHGLTPEQVVAIASHDGGKQALETVQRLLPVLCQAHGLTPEQ<br>VVAIASHDGGKQALETVQRLLPVLCQAHGLTPEQVVAIASNIGGKQALETVQALLPVL<br>CQAHGLTPEQVVAIASNIGGKQALETVQALLPVLCQAHGLTPEQVVAIASNIGGKQA<br>LETVQALLPVLCQAHGLTPEQVVAIASNIGGKQALETVQALLPVLCQAHGLTPQQVV<br>AIASNGGGKQALETVQRLLPVLCQAHGLTPEQVVAIASHDGGKQALETVQRLLPVLC<br>QAHGLTPEQVVAIASHDGGKQALETVQRLLPVLCQAHGLTPEQVVAIASHDGGKQA<br>LETVQRLLPVLCQAHGLTPEQVVAIASNIGGKQALETVQALLPVLCQAHGLTPEQVVA<br>IASNIGGKQALETVQALLPVLCQAHGLTPQQVVAIASNGGGRPALESIVAQLSRPDPS<br>GSGSGGDPISRSQLVKSELEEKKSELRHKLKYVPHEYIELIEIARNSTQDRILEMKVMEF |

TABLE 2-continued

Nucleic acid and polynucleotide sequences for the Exon 2 and Exon 3 Cbl-b targets and the corresponding TALENs for the inactivation of said gene.

| Name | SEQ ID NO. | Polynucleotide sequence |
|---|---|---|
| | | FMKVYGYRGKHLGGSRKPDGAIYTVGSPIDYGVIVDTKAYSGGYNLPIGQADEMQRY<br>VEENQTRNKHINPNEWWKVYPSSVTEFKFLFVSGHFKGNYKAQLTRLNHITNCNGA<br>VLSVEELLIGGEMIKAGTLTLEEVRRKFNNGEINFAAD<br>DNA binding domain RVDs: NN-NG-NN-HD-HD-NI-NI-NI-NI-NG-HD-HD-HD-<br>NI-NI-NG |
| Right Talen | 6 | MGDPKKKRKVIDYPYDVPDYAIDIADPIRSRTPSPARELLPGPQPDGVQPTADRGVSP<br>PAGGPLDGLPARRTMSRTRLPSPPAPSPAFSAGSFSDLLRQFDPSLFNTSLFDSLPPFG<br>AHHTEAATGEWDEVQSGLRAADAPPPTMRVAVTAARPPRAKPAPRRRAAQPSDAS<br>PAAQVDLRTLGYSQQQQEKIKPKVRSTVAQHHEALVGHGFTHAHIVALSQHPAALG<br>TVAVKYQDMIAALPEATHEAIVGVGKQWSGARALEALLTVAGELRGPPLQLDTGQLL<br>KIAKRGGVTAVEAVHAWRNALTGAPLNLTPEQVVAIASNIGGKQALETVQALLPVLC<br>QAHGLTPQQVVAIASNGGGKQALETVQRLLPVLCQAHGLTPEQVVAIASNIGGKQA<br>LETVQALLPVLCQAHGLTPQQVVAIASNGGGKQALETVQRLLPVLCQAHGLTPQQV<br>VAIASNNGGKQALETVQRLLPVLCQAHGLTPQQVVAIASNNGGKQALETVQRLLPVL<br>CQAHGLTPQQVVAIASNGGGKQALETVQRLLPVLCQAHGLTPQQVVAIASNNGGK<br>QALETVQRLLPVLCQAHGLTPQQVVAIASNNGGKQALETVQRLLPVLCQAHGLTPQ<br>QVVAIASNNGGKQALETVQRLLPVLCQAHGLTPEQVVAIASHDGGKQALETVQRLLP<br>VLCQAHGLTPQQVVAIASNGGGKQALETVQRLLPVLCQAHGLTPEQVVAIASNIGGK<br>QALETVQALLPVLCQAHGLTPQQVVAIASNGGGKQALETVQRLLPVLCQAHGLTPQ<br>QVVAIASNGGGKQALETVQRLLPVLCQAHGLTPQQVVAIASNGGGRPALESIVAQLS<br>RPDPSGSGSGGDPISRSQLVKSELEEKKSELRHKLKYVPHEYIELIEIARNSTQDRILEMK<br>VMEFFMKVYGYRGKHLGGSRKPDGAIYTVGSPIDYGVIVDTKAYSGGYNLPIGQADE<br>MQRYVEENQTRNKHINPNEWWKVYPSSVTEFKFLFVSGHFKGNYKAQLTRLNHITN<br>CNGAVLSVEELLIGGEMIKAGTLTLEEVRRKFNNGEINFAAD<br>DNA binding domain RVDs: NI-NG-NI-NG-NN-NN-NG-NN-NN-NN-HD-NG-NI-<br>NG-NG-NG |
| Cbl-b exon 3 target | 7 | TGCTGCTGAATTCTGGAGAAAGTTTTTTGGAGACAAGTAAGTAAA |
| Left Talen | 8 | MGDPKKKRKVIDYPYDVPDYAIDIADPIRSRTPSPARELLPGPQPDGVQPTADRGVSP<br>PAGGPLDGLPARRTMSRTRLPSPPAPSPAFSAGSFSDLLRQFDPSLFNTSLFDSLPPFG<br>AHHTEAATGEWDEVQSGLRAADAPPPTMRVAVTAARPPRAKPAPRRRAAQPSDAS<br>PAAQVDLRTLGYSQQQQEKIKPKVRSTVAQHHEALVGHGFTHAHIVALSQHPAALG<br>TVAVKYQDMIAALPEATHEAIVGVGKQWSGARALEALLTVAGELRGPPLQLDTGQLL<br>KIAKRGGVTAVEAVHAWRNALTGAPLNLTPQQVVAIASNNGGKQALETVQRLLPVL<br>CQAHGLTPEQVVAIASHDGGKQALETVQRLLPVLCQAHGLTPQQVVAIASNGGGKQ<br>ALETVQRLLPVLCQAHGLTPQQVVAIASNNGGKQALETVQRLLPVLCQAHGLTPEQV<br>VAIASHDGGKQALETVQRLLPVLCQAHGLTPQQVVAIASNGGGKQALETVQRLLPVL<br>CQAHGLTPQQVVAIASNNGGKQALETVQRLLPVLCQAHGLTPEQVVAIASNIGGKQ<br>ALETVQALLPVLCQAHGLTPEQVVAIASNIGGKQALETVQALLPVLCQAHGLTPQQV<br>VAIASNGGGKQALETVQRLLPVLCQAHGLTPQQVVAIASNGGGKQALETVQRLLPVL<br>CQAHGLTPEQVVAIASHDGGKQALETVQRLLPVLCQAHGLTPQQVVAIASNGGGKQ<br>ALETVQRLLPVLCQAHGLTPQQVVAIASNNGGKQALETVQRLLPVLCQAHGLTPQQ<br>VVAIASNNGGKQALETVQRLLPVLCQAHGLTPQQVVAIASNGGGRPALESIVAQLSR<br>PDPSGSGSGGDPISRSQLVKSELEEKKSELRHKLKYVPHEYIELIEIARNSTQDRILEMKV<br>MEFFMKVYGYRGKHLGGSRKPDGAIYTVGSPIDYGVIVDTKAYSGGYNLPIGQADEM<br>QRYVEENQTRNKHINPNEWWKVYPSSVTEFKFLFVSGHFKGNYKAQLTRLNHITNC<br>NGAVLSVEELLIGGEMIKAGTLTLEEVRRKFNNGEINFAAD<br>DNA binding domain RVDs: NN-HD-NG-NN-HD-NG-NN-NI-NI-NG-NG-HD-NG-<br>NN-NN-NG |
| Right Talen | 9 | MGDPKKKRKVIDYPYDVPDYAIDIADPIRSRTPSPARELLPGPQPDGVQPTADRGVSP<br>PAGGPLDGLPARRTMSRTRLPSPPAPSPAFSAGSFSDLLRQFDPSLFNTSLFDSLPPFG<br>VAHHTEAATGEWDEVQSGLRAADAPPPTMRVAVTAARPPRAKPAPRRRAAQPSDAS<br>PAAQVDLRTLGYSQQQQEKIKPKVRSTVAQHHEALVGHGFTHAHIVALSQHPAALG<br>TVAVKYQDMIAALPEATHEAIVGVGKQWSGARALEALLTVAGELRGPPLQLDTGQLL<br>KIAKRGGVTAVEAVHAWRNALTGAPLNLTPQQVVAIASNGGGKQALETVQRLLPVL<br>CQAHGLTPQQVVAIASNGGGKQALETVQRLLPVLCQAHGLTPEQVVAIASNIGGKQ<br>ALETVQALLPVLCQAHGLTPEQVVAIASHDGGKQALETVQRLLPVLCQAHGLTPQQV<br>VAIASNGGGKQALETVQRLLPVLCQAHGLTPQQVVAIASNGGGKQALETVQRLLPVL<br>CQAHGLTPEQVVAIASNIGGKQALETVQALLPVLCQAHGLTPEQVVAIASHDGGKQA<br>LETVQRLLPVLCQAHGLTPQQVVAIASNGGGKQALETVQRLLPVLCQAHGLTPQQV<br>VAIASNGGGKQALETVQRLLPVLCQAHGLTPQQVVAIASNNGGKQALETVQRLLPVL<br>CQAHGLTPQQVVAIASNGGGKQALETVQRLLPVLCQAHGLTPEQVVAIASHDGGKQ |

TABLE 2-continued

Nucleic acid and polynucleotide sequences for the Exon 2 and Exon 3 Cbl-b targets and the corresponding TALENs for the inactivation of said gene.

| Name | SEQ ID NO. | Polynucleotide sequence |
|---|---|---|
| | | ALETVQRLLPVLCQAHGLTPQQVVAIASNGGGKQALETVQRLLPVLCQAHGLTPEQV VAIASHDGGKQALETVQRLLPVLCQAHGLTPQQVVAIASNGGGRPALESIVAQLSRP DPSGSGSGGDPISRSQLVKSELEEKKSELRHKLKYVPHEYIELIEIARNSTQDRILEMKV MEFFMKVYGYRGKHLGGSRKPDGAIYTVGSPIDYGVIVDTKAYSGGYNLPIGQADEM QRYVEENQTRNKHINPNEWWKVYPSSVTEFKFLFVSGHFKGNYKAQLTRLNHITNC NGAVLSVEELLIGGEMIKAGTLTLEEVRRKFNNGEINFAAD<br>DNA binding domain RVDs: NG-NG-NI-HD-NG-NG-NI-HD-NG-NG-NN-NG-HD-NG-HD-NG |

According to still another preferred embodiment, the gene involved in the cytolytic activity to be inactivated or which gene expression is to be reduced, is the one encoding for A2A receptor (ADORA2A). The adenosine $A_{2A}$ receptor, also known as ADORA2A (in human UniProt: P29274 and RefSeq: NM_000675) is an adenosine receptor. This protein is a member of the G protein-coupled receptor (GPCR) family which possesses seven transmembrane alpha helices. There is findings that indicate that myeloid cell A2ARs have direct myelosuppressive effects that indirectly contribute to the suppression of T cells and NK (Cekic C, Day Y J, Sag D, Linden J, 2014, "Myeloid expression of adenosine A2A receptor suppresses T and NK cell responses in the solid tumor microenvironment"; Cancer Res., 74(24):7250-9).

According to one embodiment, the gene involved in the cytolytic activity to be inactivated, or which gene expression is to be reduced, is the one encoding for KLRD1. KLRD1 or Natural killer cells antigen CD94 (Killer cell lectin-like receptor subfamily D member 1) (UniProt: Q13241; genomic DNA sequence (EMBL): AJ000673.1). KLRD1 (CD94) is part of the C-type lectin superfamily, including members of the NKG2 family, which is expressed by NK cells and may be involved in the regulation of NK cell function. KLRD1 (CD94) is an antigen preferentially expressed on NK cells (reviewed in NCBI database for gene ID 3824 "KLRD1 killer cell lectin-like receptor subfamily D, member 1 [human].

According to one embodiment, the gene involved in the cytolytic activity to be inactivated, or which gene expression is to be reduced, is the one encoding for LIR1/ILT2. This gene corresponds to the Leukocyte immunoglobulin-like receptor subfamily B member 1 (CD85 antigen-like family member J); UniProt: Q8NHL6, and genomic DNA GenBank AF189277). The receptor is expressed on immune cells where it binds to MHC class I molecules on antigen-presenting cells and transduces a negative signal that inhibits stimulation of an immune response. It is thought to control inflammatory responses and cytotoxicity to help focus the immune response and limit autoreactivity. Also, there are findings that se results indicate that while the ILT2/HLA-G interaction leads to the inhibition of NK-cell functions (Favier B, Lemaoult J, Lesport E, Carosella E D, 2010, "ILT2/HLA-G interaction impairs NK-cell functions through the inhibition of the late but not the early events of the NK-cell activating synapse" FASEB J.; 24(3):689-99).

According to one embodiment, the gene involved in the cytolytic activity to be inactivated, or which gene expression is to be reduced, is the one encoding for a member of the KIR family genes. Killer-cell immunoglobulin-like receptors (KIRs) are transmembrane glycoproteins expressed by natural killer cells and subsets of T cells. The KIR proteins are classified by the number of extracellular immunoglobulin domains (2D or 3D) and by whether they have a long (L) or short (S) cytoplasmic domain. KIR proteins with the long cytoplasmic domain transduce inhibitory signals upon ligand binding via an immune tyrosine-based inhibitory motif (ITIM), while KIR proteins with the short cytoplasmic domain lack the ITIM motif and instead associate with the TYRO protein tyrosine kinase binding protein to transduce activating signals. The ligands for several KIR proteins are subsets of HLA class I molecules; thus, KIR proteins are thought to play an important role in regulation of the immune response (see on NCBI database for Gene ID: 3802 a review "KIR2DL1 killer cell immunoglobulin-like receptor, two domains, long cytoplasmic tail, 1 [*Homo sapiens* (human)" ]. KIR family members including KIR2DL1-3 (UniProt: P43626; RefSeq: NP 055033.2 NM 014218.2) and KIR2DL4 (UniProt: Q99706, RefSeq: NM 001080770). Killer cell immunoglobulin-like receptor 2DL1 is a protein that in humans is encoded by the KIR2DL1 gene (Wagtmann N, Biassoni R, Cantoni C, Verdiani S, Malnati M, Vitale M et al., 1995 "Molecular clones of the p58 NK cell receptor reveal immunoglobulin-related molecules with diversity in both the extra- and intracellular domains". *Immunity* 2 (5): 439-49; Colonna M, Samaridis J, 1995, "Cloning of immunoglobulin-superfamily members associated with HLA-C and HLA-B recognition by human natural killer cells". *Science* 268 (5209): 405-8). KIR2DL1 has been shown to interact with HLA-C (Valés-Gomez M, Reyburn H, Mandelboim M, Strominger J, 1998 "Kinetics of interaction of HLA-C ligands with natural killer cell inhibitory receptors". *Immunity* 9 (3): 337-44). The only so far reported ligand of KIR2DL4 is the non-classical HLA class 1 gene HLA-G, leading to the inhibition of the cytolytic NK cell function. A review is displayed on NCBI database with Gene ID: 3805 the "KIR2DL4 killer cell immunoglobulin-like receptor, two domains, long cytoplasmic tail, 4 [*Homo sapiens* (human)"].

CXC chemokine receptors are integral membrane proteins that specifically bind and respond to cytokines of the CXC chemokine family. They represent one subfamily of chemokine receptors, a large family of G protein-linked receptors that are known as seven transmembrane (7-TM) proteins, since they span the cell membrane seven times. There are currently seven known CXC chemokine receptors in mammals, named CXCR1 through CXCR7. CXCR2 (in human UniProt: P25025 and RefSeq: NM_001168298), CXCR4 (in human UniProt: P61073 and RefSeq: NM_001008540) and CXCR7 (in human UniProt: P25106 and RefSeq:NM_001047841) are chemokine receptors CXCR2 also called Interleukin 8 receptor, beta is a chemokine receptor CD94, also known as killer cell lectin-like receptor subfamily D, member 1 (KLRD1) is a human gene (in human UniProt: Q13241 and RefSeq:NM_001114396).

According to one embodiment, the gene involved in the cytolytic activity to be inactivated, or which gene expression is to be reduced, is the one encoding for CD94. This gene is a lectin, cluster of differentiation and a receptor that is involved in cell signaling and is expressed on the surface of natural killer cells in the innate immune system. CD94 pairs with the NKG2 molecule as a heterodimer. The CD94/NKG2 complex, on the surface of natural killer cells interacts with Human Leukocyte Antigen (HLA)-E on target cells (Lazetic S, Chang C, Houchins J, Lanier L, Phillips J, 1996, "Human natural killer cell receptors involved in MHC class I recognition are disulfide-linked heterodimers of CD94 and NKG2 subunits". *Journal of Immunology* 157 (11): 4741-5. Interestingly, the heterodimer CD94/NKG2 plays a role as inhibitor of NK cell activation (Masilamani M et al, 2006, "CD94/NKG2A inhibits NK cell activation by disrupting the actin network at the immunological synapse" J Immunol.; 177(6):3590-6; Yokoyama W M et al, 2003, "Immune functions encoded by the natural killer gene complex", Nature Reviews Immunology 3, 304-316.)

According to one embodiment, the gene involved in the cytolytic activity to be inactivated, or which gene expression is to be reduced, is the one encoding for AhR. The aryl hydrocarbon receptor (AhR or AHR or ahr or ahR) is a protein (in human UniProt: P35869) that in humans is encoded by the AHR gene (in human RefSeq: NM_001621). This receptor has been shown to regulate xenobiotic-metabolizing enzymes such as cytochrome P450 (Nebert D W, Roe A L, Dieter M Z, Solis W A, Yang Y, Dalton T P, 2000, "Role of the aromatic hydrocarbon receptor and [Ah] gene battery in the oxidative stress response, cell cycle control, and apoptosis", Biochem Pharmacol. 59(1):65-85). This receptor mediates anergy of T cell in the tumor microenvironment through binding with the tryptophan catabolite kinurenine. Inactivation of this receptor is supposed to overcome this inhibition and keep CAR NK or CAR T cell active in the tumor microenvironment (Platten et al, 2012, "Tryptophan catabolism in cancer: beyond IDO and tryptophan depletion", Cancer Res. 1; 72(21):5435-4).

According to one embodiment, the gene involved in the cytolytic activity to be inactivated, or which gene expression is to be reduced, is the one encoding for Tim-3. Hepatitis A virus cellular receptor 2 (called Tim-3, or T-cell immunoglobulin and mucin domain-containing protein 3, with human UniProt: Q8TDQ0) encodes the gene HAVCR2 (human RefSeq: NM_032782). This protein has among it functions to regulate macrophage activation, to inhibit T-helper type 1 lymphocyte (Th1)-mediated auto- and allo-immune responses, and to promote immunological tolerance. According to some finding, NK-cell responses may be negatively regulated when NK cells encounter target cells expressing cognate ligands of Tim-3 (Ndhlovu L C, Lopez-Verges S, Barbour J D, Jones R B, Jha A R, et al., 2012, "Tim-3 marks human natural killer cell maturation and suppresses cell-mediated cytotoxicity" Blood 119: 3734-3743).

According to one embodiment, the gene involved in the cytolytic activity to be inactivated, or which gene expression is to be reduced, is the one encoding for Fas (CD95). Apoptosis-mediating surface antigen FAS is also called CD95 or Tumor necrosis factor receptor superfamily member 6 (in human UniProt: P25445 and RefSeq:NM_000043). The CD95 (Fas)/CD95 ligand (CD95L) system is an important mechanism triggering apoptosis, and CD95L expression has recently been implicated for immune evasion and aggressive behavior in malignancies. The expression of CD95 and CD95L was studied in lymphomas as well as the possible relationship with tumor cell apoptosis, with emphasis on the natural killer (NK) cell lymphomas (Ng C S, Lo S T, Chan J K, 1999, Hum Pathol., 1999, "Peripheral T and putative natural killer cell lymphomas commonly coexpress CD95 and CD95 ligand", 30(1):48-53. As NK cells undergo apoptosis following target cell and NK cell receptor engagement, including the Fas (CD95)/Fas ligand (FasL) system, it is believed that the inactivation of Fas (CD95) in NK cell will prevent their apoptosis and their down-regulation cell response.

Enhancement of NK Cell Proliferation

According to one embodiment, the gene involved in the NK cell proliferation to be inactivated, or which gene expression is to be reduced, is the one encoding for Tyro-3. Tyrosine-protein kinase receptor Tyro-3 (in human UniProt: Q06418 and RefSeq: NM_006293), receptor tyrosine kinase AXL (in human UniProt: P30530 and RefSeq: NM_001265528), and proto-oncogene tyrosine-protein kinase MER (in human UniProt: Q12866 and RefSeq: NM_006343) constitute the TAM family of receptor tyrosine kinases (RTKs) characterized by a conserved sequence within the kinase domain and adhesion molecule-like extracellular domains. This small family of RTKs regulates an intriguing mix of processes, including cell proliferation/survival, cell adhesion and migration, blood clot stabilization, and regulation of inflammatory cytokine release (Linger R M, Keating A K, Earp H S, Graham D K Adv Cancer Res., 2008, "TAM receptor tyrosine kinases: biologic functions, signaling, and potential therapeutic targeting in human cancer" 100:35-83). In this paper is discussed a role for TAM receptors in oncogenic mechanisms as family members are overexpressed in a spectrum of human cancers and have prognostic significance in some.

According to one embodiment, the gene involved in the NK cell proliferation to be inactivated, or which gene expression is to be reduced, is the one encoding for GCN2. This gene called also"general control nonderepressible 2" is a serine/threonine-protein kinase (in human UniPro: Q9P2K8, RefSeq: NM_001013703.3) that senses amino acid deficiency through binding to uncharged transfer RNA (tRNA). It plays a key role in modulating amino acid metabolism as a response to nutrient deprivation. The tumor microenvironment is also characterized by the depletion of arginine which inhibits the proliferation activity of immune cells such as NK cells (Oberlies J et al, 2009, «Regulation of NK cell function by human granulocyte arginase", J Immunol. 1; 182(9):5259-67). The depletion of arginine is sensed by GCN2 which, once activated, triggers a inhibitor pathways in the cellular proliferation. The GCN2 inactivation may allow bypass the NK inhibition in the tumoral microenvironnement.

By "engraftment" (or transplantation), it is meant in the present invention a process by which transplanted or transfused cells—here, NK cells, from an allogeneic donor grow and reproduce with a recipient. To try to achieve this goal, few methodologies have been used. It has been tested in a murine nonmyeloablative allo-BMT model that a treatment by the interleukin IL-15 can promote synergistically with donor NK cell infusion the engraftment, the development of donor-derived cell subsets and suppress the host alloresponse (Hu B, Bao G, Zhang Y, Lin D, Wu Y, Wu D, Liu H., 2012, "Donor NK Cells and IL-15 promoted engraftment in nonmyeloablative allogeneic bone marrow transplantation", J Immunol. 2012 Aug. 15; 189(4):1661-70). Another approach which has been used in studies exploring adoptive transfer of NK cells after allogeneic haploidentical transplantation, where T-cell contamination could lead to lethal GVHD, is to avoid T-cell contamination. The addition of a CD56 selection after CD3 T-cell depletion typically improves NK cell purity to the 90% range and reduces B-cell contamination to less than 1% (Passweg J R, Tichelli A, Meyer-Monard S, et al., 2004, "Purified donor NK-lymphocyte infusion to consolidate engraftment after haploidentical stem cell transplantation", Leukemia, 18(11):1835-1838).

The present inventors aim to develop a new methodology to enhance engraftment of NK cells, in particular allogeneic NK cells, which is not based on fastidious, expensive and time-consuming steps of purification, and also which allows to reduce the use of concomitant treatment (such as cytokine) other than for chemotherapy. They hypothesize that the inactivation of drug resistance genes in NK cells in presence of lymphodepleting drugs may facilitate the engraftment of those cells.

According to one embodiment, the gene involved in the engraftment of NK cells in host organism to be inactivated, or which gene expression is to be reduced, is the one encoding for CD74. This gene corresponds to HLA class II histocompatibility antigen gamma chain (also known as HLA-DR antigens-associated invariant chain) is a protein (in human UniProt: P04233) that in humans is encoded by the CD74 gene (RefSeq NP_001020329). This protein involved in the formation and transport of MHC class II protein (Cresswell P, 1994, "Assembly, transport, and function of MHC class II molecules". Annu. Rev. Immunol. 12: 259-93). The inactivation of this gene may have a role in promoting the engraftment allogeneic NK cells.

Enhancement of Drug Resistance in NK Cell

To improve cancer therapy and selective engraftment of allogeneic NK cells, drug resistance is conferred to said cells to protect them from the toxic side effects of chemotherapy agent. The drug resistance of NKcells also permits their enrichment in or ex vivo, as NK cells which express the drug resistance gene will survive and multiply relative to drug sensitive cells.

By "inactivating a gene involved in drug resistance in NK cell", it is meant in the present invention that NK cell is rendered less sensitive to the drug.

According to one embodiment, the gene involved in drug resistance of NK cells to be inactivated, or which gene expression is to be reduced, is the one encoding for cyclophilin A. This gene, also known as peptidylprolyl isomerase A (Ref UniProt: Q3KQW3 encoded by the gene under RefSeq: NM_203430) can bind to cyclosporin. The cyclosporin-cyclophilin A complex inhibits a calcium/calmodulin-dependent phosphatase, calcineurin, the inhibition of which is thought to suppress organ rejection by halting the production of the pro-inflammatory molecules TNF alpha and interleukin 2 (Ho S et al, 1996 "The mechanism of action of cyclosporin A and FK506", Clin Immunol Immunopathol., 80(3 Pt 2):S40-5. Cyclophilin A is therefore the target of the immunosuppressive drug cyclosporine used for organ transplantation. The inactivation of cyclophilin A may render the NK celles insensitive to cyclosporine.

According to one embodiment, the gene involved in drug resistance of NK cells to be inactivated, or which gene expression is to be reduced, is the one encoding for TBL1XR1. It has been shown that the deletion of TBL1XR1 (UniProt:Q9BZK7 encoded by the gene in human RefSeq: NM_024665) leads to the development of prednisolone resistance in acute lymphoblastic leukemia (ALL) by decreasing the recruitment of glucocorticoid receptor to glucocorticoid responsive elements (Jones C L et al, 2014, "Loss of TBL1XR1 Disrupts Glucocorticoid Receptor Recruitment to Chromatin and Results in Glucocorticoid Resistance in a B-Lymphoblastic Leukemia Model", Journal of Biological Chemistry, published on 2014 Aug. 2; DOI: 10.1074/jbc.M114.569889).

In another embodiment, said gene involved in the drug resistance to be inactivated is the gene encoding the enzyme HPRT. The hypoxanthine-guanine phosphoribosyl transferase (HPRT) gene (human Genbank: M26434.1) can be inactivated in engineered NK cells to confer resistance to a cytostatic metabolite, the 6-thioguanine (6TG) which is converted by HPRT to cytotoxic thioguanine nucleotide and which is currently used to treat patients with cancer, in particular leukemias (Hacke, Treger et al. 2013). Guanines analogs are metabolized by HPRT that catalyzes addition of phosphoribosyl moiety and enables the formation of TGMP. Guanine analogues including 6 mercapthopurine (6MP) and 6 thioguanine (6TG) are usually used as lymphodepleting drugs to treat ALL. They are metabolized by HPRT (hypoxanthine phosphoribosyl transferase that catalyzes addition of phosphoribosyl moiety and enables formation TGMP. Their subsequent phosphorylations lead to the formation of their triphosphorylated forms that are eventually integrated into DNA. Once incorporated into DNA, thio GTP impairs fidelity of DNA replication via its thiolate groupment and generate random point mutation that are highly deleterious for cell integrity.

In another preferred embodiment, said gene involved in the engraftment to be inactivated is the gene encoding the enzyme dCK. The human deoxycytidine kinase (dCK) gene drug sensitizing gene, when inactivated, confers drug resistance to the cell such as NK cell. This enzyme is required for the phosphorylation of the deoxyribonucleosides deoxycytidine (dC), deoxyguanosine (dG) and deoxyadenosine (dA). Purine nucleotide analogs (PNAs) are metabolized by dCK into mono-, di- and tri-phosphate PNA. Their triphosphate forms and particularly clofarabine triphosphate compete with ATP for DNA synthesis, acts as proapoptotic agent and are potent inhibitors of ribonucleotide reductase (RNR) which is involved in trinucleotide production In another embodiment, said gene involved in the drug resistance to be inactivated is the gene encoding the CD52 antigen. The latter (also called CAMPATH-1 antigen) is a glycoprotein (in human UniProt: P31358) that in humans is encoded by the CD52 gene (in human, NM_001803). L'alemtuzumab (marketed under the names of Campath or Lemtrada) is a monoclonal antibody est humanized IgG1 kappa specific to the CD52 glycoprotein located on the surface of lymphocytes.

Immune-Checkpoint Genes

NK-cell-mediated immunity includes multiple sequential steps involving the clonal selection of antigen specific cells, their activation and proliferation in secondary lymphoid tissue, their trafficking to sites of antigen and inflammation, the execution of direct effector function and the provision of help (through cytokines and membrane ligands) for a multitude of effector immune cells. Each of these steps is regulated by counterbalancing stimulatory and inhibitory signal that fine-tune the response. It will be understood by those of ordinary skill in the art, that the term "immune checkpoints" means a group of molecules expressed by NK cells. These molecules effectively serve as "brakes" to down-modulate or inhibit an immune response.

According to one embodiment, the gene considered as immune checkpoint to be inactivated, or which gene expression is to be reduced, is the one encoding for PD-1. Programmed cell death protein 1, also known as PD-1 (UniProt: Q15116) and CD279 is a protein that in humans is encoded by the PDCD1 gene (RefSeq: NM_005018; Shinohara T, Taniwaki M, Ishida Y, Kawaichi M, Honjo T, 1994, "Structure and chromosomal localization of the human PD-1 gene (PDCD1)". *Genomics* 23 (3): 704-6). PD-1 is a member of the B7 family of co-signaling receptor that is up-regulated on activated T cells, NK cells, B cells, dendritic cells, and monocytes (Nirschl C J, Drake C G, 2013; "Molecular pathways: co-expression of immune checkpoint molecules: signaling pathways and implications for cancer immunotherapy", *Clin Cancer Res,* 19:4917-24)). In NK cells, PD-1 engagement impairs activation, conjugate formation, cytotoxicity, and cytokine production (Dolina J S, Sung S S, Novobrantseva T I, Nguyen T M, Hahn Y S, 2013, "Lipidoid nanoparticles containing PD-L1 siRNA delivered in vivo enter Kupffer cells and enhance NK and CD8(+) T cell-mediated hepatic antiviral immunity. *Mol Ther Nucleic Acids* ( ) 2:e72).

Expression of Polypeptide Involved in the Cytolytic Activity of NK Cells

According to one embodiment, the method comprises an additional genetic modification of NK cell by expression of the gene encoding for interleukin-2 receptor alpha chain (also called CD25). This protein (in human: UniProt P01589) that in humans is encoded by the IL2RA gene (RefSeq: NM_000417). It has been reported that, by using some NK-resistant tumour cell lines, that activation of NK cells with interleukin 2 (IL-2) resulted in significant lysis of these tumour targets (Lehmann C, Zeis M, Uharek L., 2001, "Activation of natural killer cells with interleukin 2 (IL-2) and IL-12 increases perforin binding and subsequent lysis of tumour cells" Br J Haematol. 114(3):660-5).

According to one embodiment, the method comprises an additional genetic modification of NK cell by expression of the gene encoding of interleukin 15 (IL-15). This is a cytokine with structural similarity to IL-2. Like IL-2, IL-15 binds to and signals through a complex composed of IL-2/IL-15 receptor beta chain (CD122) and the common gamma chain (gamma-C, CD132). IL-15 is secreted by mononuclear phagocytes (and some other cells) following infection by virus(es). This cytokine induces cell proliferation of natural killer cells. Rowley J et al, 2009, «Expression of IL-15RA or an IL-15/1L-15RA fusion on CD8+ T cells modifies adoptively transferred T cell function in cis», Eur J Immunol.; 39(2): 491-506) designed the IL-15/IL-15RA fusion is a chimeric protein which allows the co-expression of IL-15 receptor with its ligand IL-15. This represents a kind of «all in one» auto-activating system, under a polycistronic form which, via the 2A peptide, allows the expression of the 2 proteins separately.

According to one embodiment, the method comprises an additional genetic modification of NK cell by expression of the gene encoding the interferon IFNγ. This interferon has antiviral, immunoregulatory, and anti-tumor properties (Schroder K, Hertzog P J, Ravasi T, Hume D A, 2004, "Interferon-gamma: an overview of signals, mechanisms and functions". *J. Leukoc. Biol.* 75 (2): 163-89). As part of the innate immune response IFNγ is produced predominantly by natural killer (NK) and natural killer T (NKT) cells. One of the effects of IFNγ is to promote NK cell activity (Konjevic G et al, 2011, "Association of decreased NK cell activity and IFNγ expression with pSTAT dysregulation in breast cancer patients" J BUON. 16(2):219-26).

According to one embodiment, the method comprises an additional genetic modification of NK cell by expression of the gene encoding the endopeptidase p60 from *Listeria*. This endopeptidase p60 (Uniprot: P21171) originated from *Listeria* contributes in NK cell activation and in IFNγ production (Humann J, Bjordahl R, Andreasen K, Lenz L L, 2007, "Expression of the p60 autolysin enhances NK cell activation and is required for *Listeria monocytogenes* expansion in IFN-gamma-responsive mice". J Immunol. 178(4):2407-14). The activation parts LysM and SH3 of the p60 have been identified (Schmidt et al, 2011, "A LysM and SH3-Domain Containing Region of the *Listeria monocytogenes* p60 Protein Stimulates Accessory Cells to Promote Activation of Host NK Cells", PLoS Pathog.; 7(11)). The surexpression of p60 of the *Listeria* by the NK cells is seeked for their auto-activation when administrated to the patient.

According to one embodiment, the method comprises an additional genetic modification of NK cell by expression of the gene encoding TNFα. The Tumor necrosis factor s a cell signaling protein (human UniProt: P01375; RefSeq: NM_000585) involved in systemic inflammation and is one of the cytokines that make up the acute phase reaction. It is produced chiefly by activated macrophages, although it can be produced by many other cell types such as CD4+ lymphocytes, NK cells, neutrophils, mast cells, eosinophils, and neurons. There are findings suggesting that TNF-α is implicated in the NK cytolytic function (Wang R, Jaw J J, Stutzman N C, Zou Z, Sun P D, 2012,"Natural killer cell-produced IFN-γ and TNF-α induce target cell cytolysis through up-regulation of ICAM-1". J Leukoc Biol. February; 91(2):299-309).

According to one embodiment, the method comprises an additional genetic modification of NK cell by expression of the gene encoding IL-12A. Interleukin-12 subunit alpha (human UniProt: P29459) encodes the IL12A gene (human RefSeq: NM_000882). This cytokine that can act as a growth factor for activated T and NK cells, enhance the lytic activity of NK/lymphokine-activated Killer cells, and stimulate the production of IFN-gamma by resting PBMC. IL-12 plays an important role in the activities of natural killer cells and T lymphocytes. IL-12 mediates enhancement of the cytotoxic activity of NK cells and CD8+ cytotoxic T lymphocytes.

Expression of Polypeptide to Confer Drug Resistance to NK Cells

According to another embodiment, the method comprises an additional genetic modification of NK cell to confer drug resistance by expression of the gene encoding aldehyde deshydrogenase (ALDH). Human aldehyde dehydrogenases (ALDHs; in human UniProt: P05091; enzyme entry in ExPASy: EC 1.2.1.3) comprise a family of 17 homologous enzymes that metabolize different biogenic and exogenic aldehydes, including the inactivation of cyclophosphamide or maphosphamide (Khanna M, Chen C H, Kimble-Hill A, Parajuli B, Perez-Miller S, Baskaran S, Kim J, Dria K, Vasiliou V, Mochly-Rosen D, Hurley T D., 2011 "Discovery of a novel class of covalent inhibitor for aldehyde dehydrogenases", J Biol Chem. 2011 Dec. 16; 286(50):43486-94.). Human ALDH2 is encoded by the gene having RefSeq no: N M_000690.3.

According to another embodiment, the method comprises an additional genetic modification of NK cell to confer drug resistance by expression of the gene encoding the enzyme MGMT. The enzyme 06-methylguanine DNA-methyltransferase (MGMT; in human UniProt: P16455, enzyme entry in ExPASy: EC 1.2.1.3; Cas number: 77271-19-3) is a protein that in humans is encoded by the $O^6$-methylguanine DNA methyltransferase (MGMT) gene (in human, RefSeq: NM_002412). The MGMT confers resistance to alkylating agents such as cyclophosphamide (Bobola M S, Blank A, Berger M S, Silber J R., 1995, "Contribution of 06-methylguanine-DNA methyltransferase to monofunctional alkylating-agent resistance in human brain tumor-derived cell lines", Mol Carcinog. 1995 June; 13(2):70-80).

In another embodiment, said gene involved in the drug resistance to be expressed is one of the gene involved in the methotrexate (MTX) pathway genes, such as AMPD1, ATIC, DHFR, FPGS, GGH, ITPA, MTHFD1, SHMT1, SLC19A1 (RFC) and TYMS (Owen et al, 2013, "Genetic polymorphisms in key methotrexate pathway genes are associated with response to treatment in rheumatoid arthritis patients", Pharmacogenomics J. 13(3):227-34).

In another embodiment, said gene involved in the drug resistance to be expressed is glutathione transferase (GST). The DNA alkylating agents such as busulfan and cyclophosphamide are frequently included in conditioning regimens before hematopoietic stem cell transplantation (HSCT). Both drugs are detoxified by glutathione transferases (GST) (Bremer S et al, 2015 "Glutathione transferase gene variants influence busulfan pharmacokinetics and outcome after myeloablative conditioning", Ther Drug Monit. [Epub ahead of print])

In another embodiment, said gene involved in the drug resistance to be expressed is cytidine deaminase. The enzyme cytidine desaminase confers drug resistance to nucleosides such as cytosine arabinoside and gemcitabine (Neff T et al, 1996, "Forced expression of cytidine deaminase confers resistance to cytosine arabinoside and gemcitabine", Exp Hematol. 24(11):1340-6).

Chimeric Antigen Receptor (CAR) Endowed NK Cells

By chimeric antigen receptor (CAR) is intended molecules that combine a binding domain against a component present on the target cell, for example an antibody-based specificity for a desired antigen (e.g., tumor antigen) with an immune cell as T cell receptor-activating intracellular domain to generate a chimeric protein that exhibits a specific anti-target cellular immune activity. Generally, CAR consists of an extracellular single chain antibody (scFvFc) fused to the intracellular signaling domain of the T cell antigen receptor complex zeta chain (scFvFc:ζ) and have the ability, when expressed in NK cells, to redirect antigen recognition based on the monoclonal antibody's specificity.

Initial and extensive work has been done on T cells. Adoptive immunotherapy, which involves the transfer of autologous immune cells and in particular antigen-specific T cells generated ex vivo, is a promising strategy to treat viral infections and cancer. The immune cells such as T cells used for adoptive immunotherapy can be generated either by expansion of antigen-specific T cells or redirection of T cells through genetic engineering (Park, Rosenberg et al. 2011). Transfer of viral antigen specific T cells is a well-established procedure used for the treatment of transplant associated viral infections and rare viral-related malignancies. Similarly, isolation and transfer of tumor specific T cells has been shown to be successful in treating melanoma. Novel specificities in T cells have been successfully generated through the genetic transfer of transgenic T cell receptors or chimeric antigen receptors (CARs) (Jena, Dotti et al. 2010, Blood 116(7):1035-44). CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and heavy variable fragments of a monoclonal antibody joined by a flexible linker. Binding moieties based on receptor or ligand domains have also been used successfully. The signaling domains for first generation CARs are derived from the cytoplasmic region of the CD3zeta or the Fc receptor gamma chains. First generation CARs have been shown to successfully redirect T cell cytotoxicity, however, they failed to provide prolonged expansion and anti-tumor activity in vivo. Signaling domains from co-stimulatory molecules including CD28, OX-40 (CD134), ICOS and 4-1BB (CD137) have been added alone (second generation) or in combination (third generation) to enhance survival and increase proliferation of CAR modified T cells. CARs have successfully allowed T cells to be redirected against antigens expressed at the surface of tumor cells from various malignancies including lymphomas and solid tumors (Jena, Dotti et al. 2010, Blood 116(7):1035-44). However, despite their unprecedent efficacy for tumor eradication in vivo, CAR T cells can promote acute adverse events after being transferred into patients. Among the well documented adverse events is Graft versus host disease (GvHD), on-target off-tumor activity or aberrant lymphoproliferative capacity due to vector derived insertional mutagenesis.

Prior art such as the review (Hermanson D L and Kaufman D S 2015 "Utilizing Chimeric Antigen Receptors to Direct Natural Killer Cell Activity", Front Immunol; 6: 195) has reported that CAR constructs have been performed in NK cells with a focus on comparing the use of different signaling domains in combination with other co-activating domains.

According to another aspect, the method of the invention comprises further a step of c) introducing into said NK cell an exogenous nucleic acid molecule comprising a nucleotide sequence coding for a Chimeric Antigen Receptor (CAR) directed against at least one antigen expressed at the surface of a malignant or infected cell.

The NK cells of the invention may be engineered to express a CAR-based polynucleotide either under a single form (scCAR) or under a multi-chain form (mcCAR).

According to one embodiment, the CAR comprises an extracellular domain, wherein the VH and VL chains encode anti-CD16 scFvs. In this case, the anti-CD16 CAR may be considered as «homing CAR» due to its capacity to target NK towards areas densely populated in macrophages, neutrophiles, monocytes and NK cells which express CD16. Low affinity immunoglobulin gamma Fc region receptor III-B (or CD16b antigen, human UniProt: O75015) encodes the FCGR3B gene (human RefSeq: NM_000570). CD16 has been identified as Fc receptors FcγRIIIa (CD16a) and FcγRIIIb (CD16b). These receptors bind to the Fc portion of IgG antibodies which then activates the NK cell for antibody-dependent cell-mediated cytotoxicity. The Fc receptor CD16 is present on essentially all CD56(dim) peripheral blood natural killer (NK) cells. Upon recognition of antibody-coated cells it delivers a potent signal to NK cells, which eliminate targets through direct killing and cytokine production (Romee R, Foley B, Lenvik T, Wang Y, Zhang B, Ankarlo D, Luo X, Cooley S, Verneris M, Walcheck B, Miller J, 2013; "NK cell CD16 surface expression and function is regulated by a disintegrin and metalloprotease-17 (ADAM17)" Blood.121(18):3599-608).

Single Chain CAR

In one embodiment, the Chimeric Antigen Receptor (CAR) is a single-chain CAR.

In a preferred embodiment, said extracellular ligand-binding domain is a scFv. Other binding domain than scFv can also be used for predefined targeting of lymphocytes, such as camelid single-domain antibody fragments or receptor ligands like a vascular endothelial growth factor polypeptide, an integrin-binding peptide, heregulin or an IL-13 mutein, antibody binding domains, antibody hypervariable loops or CDRs as non limiting examples.

As preferred examples of scFv according to the invention, VH and VL chains have as antigenic target sequence of over 80% identity, preferably over 90%, and more preferably over 95% with SEQ ID NO 10 (CD19 antigen), SEQ ID NO 11 (CD38 antigen), SEQ ID NO 12 (CD123 antigen), SEQ ID NO 13 (CS1 antigen), SEQ ID NO 14 (BCMA antigen), SEQ ID NO 15 (FLT-3 antigen), SEQ ID NO 16 (CD33 antigen), SEQ ID NO 17 (CD70 antigen), SEQ ID NO 18 (EGFR-3v antigen) and SEQ ID NO 19 (WT1 antigen).

Said polypeptide of a) further may comprise a stalk region between said extracellular ligand-binding domain and said transmembrane domain. The term "stalk region" used herein generally means any oligo- or polypeptide that functions to link the transmembrane domain to the extracellular ligand-binding domain. In particular, stalk region are used to provide more flexibility and accessibility for the extracellular ligand-binding domain. A stalk region may comprise up to 300 amino acids, preferably 10 to 100 amino acids and most preferably 25 to 50 amino acids. Stalk region may be derived from all or part of naturally occurring molecules, such as from all or part of the extracellular region of CD8, CD4 or CD28, or from all or part of an antibody constant region. Alternatively the stalk region may be a synthetic sequence that corresponds to a naturally occurring stalk sequence, or may be an entirely synthetic stalk sequence.

Said polypeptide may further comprise at least one signal-transducing domain. In a most preferred embodiment, said signal-transducing domain is selected from the group consisting of CD28, OX40, ICOS, CD137 and CD8.

Said C-terminal cytoplasmic tail of FcεRI alpha, beta and/or gamma chain fragment further comprises TNFR-associated Factor 2 (TRAF2) binding motifs. In a most preferred embodiment, said C-terminal cytoplasmic tail of FcεRI alpha, beta and/or gamma chain is replaced by intracytoplasmic tail of costimulatory TNFR member family. Cytoplasmic tail of costimulatory TNFR family member contains TRAF2 binding motifs consisting of the major conserved motif (P/S/A)X(Q/E)E) or the minor motif (PXQXXD), wherein X is any amino acid. TRAF proteins are recruited to the intracellular tails of many TNFRs in response to receptor trimerization.

Said intracytoplasmic domain of FcεRI alpha, beta and/or gamma chain is replaced by intracytoplasmic domain of TCR zeta chain (also named CD3 zeta). In another preferred embodiment, said intracytoplasmic domain of FcεRI alpha, beta and/or gamma chain comprises at least one additional immunoreceptor tyrosine-based activation motif (ITAM). ITAMs are well defined signaling motifs found in the intracytoplasmic tail of a variety of receptors that serve as binding sites for syk/zap70 class tyrosine kinases. Examples of ITAM used in the invention include those derived from TCRzeta, FCRgamma, FCRbeta, CD3gamma, CD3delta, CD3epsilon, CD5, CD22, CD79a, CD79b, and CD66d.

Multi-Chain Chimeric Antigen Receptor (CAR)

In another embodiment, the invention relates to a multi-chain chimeric antigen receptor (CAR) particularly adapted to the production and expansion of engineered immune cells such as T-cells of the present invention. The multi-chain CAR comprising at least two of the following components:

a) one polypeptide comprising the transmembrane domain of FcεRI alpha chain and an extracellular ligand-binding domain, b) one polypeptide comprising a part of N- and C-terminal cytoplasmic tail and the transmembrane domain of FcεRI beta chain and/or c) two polypeptides comprising each a part of intracytoplasmic tail and the transmembrane domain of FcεRI gamma chain, whereby different polypeptides multimerize together spontaneously to form dimeric, trimeric or tetrameric CAR.

Multi-chain architectures are more particularly disclosed in WO2014039523.

The term "a part of" used herein refers to any subset of the molecule, that is a shorter peptide. Alternatively, amino acid sequence functional variants of the polypeptide can be prepared by mutations in the DNA which encodes the polypeptide. Such functional variants include, for example, deletions from, or insertions or substitutions of, residues within the amino acid sequence. Any combination of deletion, insertion, and substitution may also be made to arrive at the final construct, provided that the final construct possesses the desired activity, especially to exhibit a specific anti-target cellular immune activity.

Are also comprised in the scope of the present invention, polynucleotides, vectors encoding the above described multi-chain CAR according to the invention.

In encompassed particular embodiment, the invention relates to a method of preparing NK cells for immunotherapy comprising introducing into said NK cells the different polypeptides composing said multi-chain CAR and expanding said cells.

The present invention also relates isolated cells or cell lines susceptible to be obtained by said method to engineer cells. In particular said isolated cell comprises exogenous polynucleotide sequences encoding polypeptides composing said multi-chain CAR.

Activation and Expansion of NK Cells

Another embodiment of the present invention concerns the above described method comprising the step of:

d) expanding the resulting engineered NK cell.

In one embodiment, said cells can be expanded by co-culturing with tissue or cells. Said cells can also be expanded in vivo, for example in the subject's blood after administrating said cell into the subject.

The invention also provides a method for activating an NK cell in vivo, or a method of modulating NK cell maturation (or increasing NK cell reactivity or activity during NK cell maturation) in vivo in a mammal, a method of the method comprising bringing NK cells that express a NKp46 polypeptide into contact with a compound that inhibits a NKp46 polypeptide. Said bringing into contact preferably comprises administering the compound that inhibits a NKp46 polypeptide to the mammal. Activating an NK cell optionally comprises increasing the reactivity or cytoxicity of NK cells toward target cells (infected cells, tumor cells, pro-inflammatory cells, etc.), increasing activation, activation markers (e.g. CD107 expression) and/or IFNγ production in an NK cell, and/or increasing the frequency in vivo of such activated, reactive, cytotoxic and/or activated NK cells.

Accordingly to the invention, NK cells to be engineered may be fresh or cytokine activated NK cells or ex-vivo expanded NK cells. (Richard W. Childs and Maria Berg, (2013), " Bringing natural killer cells to the clinic: ex vivo manipulation», *ASH Education Book, vol.* 2013 *no.* 1, 234-246). All of them are obtained from PBMC. Usually, for purification sake, there is a step of CD3+ depletion in both cases followed by a selection of CD56+ cells or a depletion of CD19+ cells According to the ex-vivo expansion protocol, an incubation may be done with cytokines alone without the presence of feeders (such as APCs) at the end of the culture. After the CD3+ depletion, in case of ex-vivo expansion, there is a step of incubation with K562 feeders (genetically modified, ex: 4-1BB/IL-15, mbIL-21 . . . ), or PBMC feeders or by NAM & cytokines (no feeders). Following the CD3+ depletion, a step of CD56+ selection may be done, followed optionally by IL-2 activation for the cytokine activated NK cells; or by an additional incubation with EBV-LCL feeders or with PBMC feeder (CD3+/CD56− cell) for the ex-vivo expanded NK cells. An optional step of CD19+ depletion may be applied instead of the CD56+ selection (Passweg J R, Tichelli A, Meyer-Monard S, et al., 2004 *"Purified donor NK-lymphocyte infusion to consolidate engraftment after haploidentical stem cell transplantation. Leukemia* 18(11): 1835-1838"; Murphy W J, Parham P, and Miller J S, 2012, *"NK cells—from bench to clinic"* Biol Blood Marrow Transplant 18(1 Suppl):S2-7).

According to the protocol using fresh and activated NK cells, the PBMCs after been CD3+ depleted may be activated by the cytokines without feeder cells, such as IL-15 and IL-2, given alone or in combination with other growth factors. This cytokine activation, usually overnight, can be followed by a CD56+ cells selection or a CD19+ cells depletion. To prevent T-cell and NKT-cell contamination and overgrowth, T cells may be depleted from PBMCs either before the initiation of NK cell cultures or at the end of the expansion culture (Lapteva N, Durett A G, Sun J et al. (2012) "*Large-scale ex vivo expansion and characterization of natural killer cells for clinical applications*". Cytotherapy 14(9):1131-1143.

Although culturing NK cells in cytokine-containing medium alone is usually less effective in expanding NK cells compared with cultures containing feeder cells, such culture conditions are capable of activating NK cells quickly, even after a short overnight incubation, substantially enhancing NK cell cytotoxicity against tumor targets ex vivo. Miller et al used a strategy of CD3 depletion of mononuclear cells (using the Miltenyi CliniMACS system) collected by apheresis from haploidentical donors, followed by a brief 8- to 16-hour culture in X-VIVO15 medium containing IL-2 (1000 U/mL), with activated cells being infused into patients after haploidentical stem cell transplantation or after no transplantation (Miller J S, Soignier Y, Panoskaltsis-Mortari A et al. (2005) Successful adoptive transfer and in vivo expansion of human haploidentical NK cells in patients with cancer. Blood 105(8):3051-3057.) In case of an ex-vivo NK cell expansion without feeder cells, it may be useful to expand higly activated NK cells from unseparated PBMCs of myeloma patients by using media containing cytokines and the anti-CD3 antibody OKT3 (removed from cultures after day 5). (Alici E, Sutlu T, Björkstrand B, et al., 2008, *"Autologous antitumor activity by NK cells expanded from myeloma patients using GMP-compliant components"* Blood 111(6):3155-3162.)

NK cell expansion technique that uses NAM (based on trypticase Soy Agar and hemin solution) in the medium, which appears to substantially increase CD62L expression on NK cells, leading to their improved homing into the spleens and BM of immune-deficient mice (Frei G M, Persi N, Lador C, et al., 2011, *"Nicotinamide, a form of vitamin* 83, *promotes expansion of natural killer cells that display increased in vivo survival and cytotoxic activity"* [abstract] Blood (ASH Annual Meeting Abstracts) 118(21):4035).

The buffer, preferably PBS (without divalent cations such as, calcium and magnesium). Again, those of ordinary skill in the art can readily appreciate any cell concentration may be used. The mixture may be cultured for several hours (about 3 hours) to about 14 days or any hourly integer value in between. In another embodiment, the mixture may be cultured for 21 days. Conditions appropriate for immune cells such as NK cell culture include an appropriate media (e.g., Minimal Essential Media or RPMI Media 1640 or, X-vivo 5, (Lonza)) that may contain factors necessary for proliferation and viability, including serum (e.g., fetal bovine or human serum), interleukin-2 (IL-2), insulin, IFN-g, 1L-4, 1L-7, GM-CSF, -10, -2, 1L-15, TGFp, and TNF- or any other additives for the growth of cells known to the skilled artisan. Other additives for the growth of cells include, but are not limited to, surfactant, plasmanate, and reducing agents such as N-acetyl-cysteine and 2-mercaptoethanoi. Media can include RPMI 1640, A1M-V, DMEM, MEM, a-MEM, F-12, X-Vivo 1, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of NK cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% C02). Immune cells such as NK cells that have been exposed to varied stimulation times may exhibit different characteristics.

Delivery Methods

The different methods described above involve introducing rare cutting endonuclease, TALE-nuclease, CAR or multi-chain CAR optionally with DNA-end processing enzyme or exogenous nucleic acid into a cell.

As non-limiting example, rare cutting endonucleases, TALE-nucleases, gene encoding non-endogenous immunosuppressive polypeptide, CAR or multi-chain CAR optionally with DNA-end processing enzyme or exogenous nucleic acid can be introduced as transgenes encoded by one or as different plasmidic vectors. Different transgenes can be included in one vector which comprises a nucleic acid sequence encoding ribosomal skip sequence such as a sequence encoding a 2A peptide. 2A peptides, which were identified in the Aphthovirus subgroup of picornaviruses, causes a ribosomal "skip" from one codon to the next without the formation of a peptide bond between the two amino acids encoded by the codons (see Donnelly et al., J. of General Virology 82: 1013-1025 (2001); Donnelly et al., J. of Gen. Virology 78: 13-21 (1997); Doronina et al., Mol. And. Cell. Biology 28(13): 4227-4239 (2008); Atkins et al., RNA 13: 803-810 (2007)). By "codon" is meant three nucleotides on an mRNA (or on the sense strand of a DNA molecule) that are translated by a ribosome into one amino acid residue. Thus, two polypeptides can be synthesized from a single, contiguous open reading frame within an mRNA when the polypeptides are separated by a 2A oligopeptide sequence that is in frame. Such ribosomal skip mechanisms are well known in the art and are known to be used by several vectors for the expression of several proteins encoded by a single messenger RNA. As non-limiting example, in the present invention, 2A peptides have been used to express into the cell the rare-cutting endonuclease and a DNA end-processing enzyme or the different polypeptides of the multi-chain CAR.

Said plasmid vector can contain a selection marker which provides for identification and/or selection of cells which received said vector.

Polypeptides may be synthesized in situ in the cell as a result of the introduction of polynucleotides encoding said polypeptides into the cell. Alternatively, said polypeptides could be produced outside the cell and then introduced thereto. Methods for introducing a polynucleotide construct into animal cells are known in the art and including as non-limiting examples stable transformation methods wherein the polynucleotide construct is integrated into the genome of the cell, transient transformation methods wherein the polynucleotide construct is not integrated into the genome of the cell and virus mediated methods. Said polynucleotides may be introduced into a cell by for example, recombinant viral vectors (e.g. retroviruses, adenoviruses), liposome and the like. For example, transient transformation methods include for example microinjection, electroporation or particle bombardment. Said polynucleotides may be included in vectors, more particularly plasmids or virus, in view of being expressed in cells.

Electroporation

Polynucleotides encoding polypeptides according to the present invention can be mRNA which is introduced directly into the cells, for example by electroporation.

For instance, can be used the cytoPulse technology which allows, by the use of pulsed electric fields, to transiently permeabilize living cells for delivery of material into the cells. The technology, based on the use of PulseAgile (Cellectis property) electroporation waveforms grants the precise control of pulse duration, intensity as well as the interval between pulses (U.S. Pat. No. 6,010,613 and International PCT application WO2004083379). All these parameters can be modified in order to reach the best conditions for high transfection efficiency with minimal mortality. Basically, the first high electric field pulses allow pore formation, while subsequent lower electric field pulses allow to move the polynucleotide into the cell.

As an example, the invention relates to a method of transforming NK cell comprising contacting said NK cell with RNA and applying to NK cell an agile pulse sequence consisting of:

(a) one electrical pulse with a voltage range from 2250 to 3000 V per centimeter, a pulse width of 0.1 ms and a pulse interval of 0.2 to 10 ms between the electrical pulses of step (a) and (b);

(b) one electrical pulse with a voltage range from 2250 to 3000 V with a pulse width of 100 ms and a pulse interval of 100 ms between the electrical pulse of step (b) and the first electrical pulse of step (c); and (c) 4 electrical pulses with a voltage of 325 V with a pulse width of 0.2 ms and a pulse interval of 2 ms between each of 4 electrical pulses.

Any values included in the value range described above are disclosed in the present application. Electroporation medium can be any suitable medium known in the art. Preferably, the electroporation medium has conductivity in a range spanning 0.01 to 1.0 milliSiemens.

As non-limiting examples, said RNA encodes a rare-cutting endonuclase, one monomer of the rare-cutting endonuclease such as Half-TALE-nuclease, a Chimeric Antigen Receptor, at least one component of the multi-chain chimeric antigen receptor, an exogenous nucleic acid, one additional catalytic domain.

Engineered NK Cell

NK cells differ from natural killer T cells (NKTs) phenotypically, by origin and by respective effector functions; often, NKT cell activity promotes NK cell activity by secreting IFNγ. In contrast to NKT cells, NK cells do not express T-cell antigen receptors (TCR) or pan T marker CD3 or surface immunoglobulins (Ig) B cell receptors, but they usually express the surface markers CD16 (FcγRIII) and CD56 in humans, NK1.1 or NK1.2 in C57BL/6 mice. Up to 80% of human NK cells also express CD8. Within human peripheral blood, the more mature CD56(dim) NK cell efficiently kills malignant targets at rest, whereas the less mature CD56(bright) NK cells cannot.

Prior to expansion and genetic modification of the cells of the invention, a source of cells can be obtained from a subject through a variety of non-limiting methods. Immune cells such as NK cells can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. Any number of immune cell lines available and known to those skilled in the art, may be used.

In another embodiment, said cell can be derived from a healthy donor, from a patient diagnosed with cancer or from a patient diagnosed with an infection. Said cell is part of a mixed population of cells which present different phenotypic characteristics.

In the scope of the present invention is also encompassed a cell line obtained from a transformed immune cell such as NK cell according to the method previously described.

Modified cells resistant to an immunosuppressive treatment and susceptible to be obtained by the previous method are encompassed in the scope of the present invention.

According to an embodiment, said NK cells are hematopoietic cells, and more preferably primary cells.

Therapeutic Applications

In another embodiment, isolated cell obtained by the different methods or cell line derived from said isolated cell as previously described can be used as a medicament.

In another embodiment, said medicament can be used for treating cancer or infections in a patient in need thereof. In another embodiment, said isolated cell according to the invention or cell line derived from said isolated cell can be used in the manufacture of a medicament for treatment of a cancer or a viral infection in a patient in need thereof.

In another aspect, the present invention relies on methods for treating patients in need thereof, said method comprising at least one of the following steps:

(a) providing an NK cell obtainable by any one of the methods previously described;

(b) Administrating said transformed NK cell to said patient,

On one embodiment, said NK cell of the invention can undergo robust in vivo NK cell such as NK cell expansion and can persist for an extended amount of time.

Said treatment can be ameliorating, curative or prophylactic. It may be either part of an autologous immunotherapy or part of an allogenic immunotherapy treatment. By autologous, it is meant that cells, cell line or population of cells used for treating patients are originating from said patient or from a Human Leucocyte Antigen (HLA) compatible donor. By allogeneic is meant that the cells or population of cells used for treating patients are not originating from said patient but from a donor.

The invention is particularly suited for allogenic immunotherapy, insofar as it enables the transformation of NK cells, typically obtained from donors, into non-alloreactive cells. This may be done under standard protocols and reproduced as many times as needed. The resulted modified immune cells may be pooled and administrated to one or several patients, being made available as an "off the shelf" therapeutic product.

The present invention encompasses a pharmaceutical composition which contains a mixture of NK cells and other PBMCs, said immune cells originating preferably from the same donor, said NK cells being obtained by the method such as described above, and said NK cells representing between 0.1% and 40%, preferably between 0.2% and 20%, more preferably between 5% and 16% of the total of immune cells.

As a particular embodiment, to the purified engineered NK cells of the present invention are added engineered or non-engineered T cells, obtained from the same donor or from a different donor.

According to one embodiment, the composition of the invention contains between 2.5% to 5% of engineered NK cells in which the expression of at least one gene selected in the group consisting of those encoding for TGF-β receptor, Cbl-B, A2A receptor, KLRD1, LIR1/ILT2, KIRs, AhR, Tim-3, Tyro-3, GCN2, CD94, CD74, cyclophilin A, TBL1XR1, HPRT, dCK, CD5, beta2M and PD-1 is reduced or inactivated by using a specific endonuclease, said engineered NK cells being obtained before the step of expansion of said engineered NK cells.

According to an alternative embodiment, said above composition contained between 10% and 25% of engineered NK cells which are obtained after the step of expansion of said cells.

Cells that can be used with the disclosed methods are described in the previous section. Said treatment can be used to treat patients diagnosed with cancer, viral infection, or Graft versus Host Disease (GvHD). Cancers that may be treated include tumors that are not vascularized, or not yet substantially vascularized, as well as vascularized tumors. The cancers may comprise nonsolid tumors (such as hematological tumors, for example, leukemias and lymphomas) or may comprise solid tumors. Types of cancers to be treated with the CARs of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

It can be a treatment in combination with one or more therapies against cancer selected from the group of antibodies therapy, chemotherapy, cytokines therapy, dendritic cell therapy, gene therapy, hormone therapy, laser light therapy and radiation therapy.

According to a preferred embodiment of the invention, said treatment can be administrated into patients undergoing an immunosuppressive treatment. Indeed, the present invention preferably relies on cells or population of cells, which have been made resistant to at least one immunosuppressive agent due to the inactivation of a gene encoding a receptor for such immunosuppressive agent. In this aspect, the immunosuppressive treatment should help the selection and expansion of the NK cells according to the invention within the patient.

The administration of the cells or population of cells according to the present invention may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous or intralymphatic injection, or intraperitoneally. In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. The cells or population of cells can be administrated in one or more doses. In another embodiment, said effective amount of cells are administrated as a single dose. In another embodiment, said effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, said effective amount of cells or composition comprising those cells are administrated parenterally. Said administration can be an intravenous administration. Said administration can be directly done by injection within a tumor.

In certain embodiments of the present invention, cells are administered to a patient in conjunction with (e.g., before, simultaneously or following) any number of relevant treatment modalities, including but not limited to treatment with agents such as antiviral therapy, cidofovir and interleukin-2, cytarabine (also known as ARA-C) or nataliziimab treatment for MS patients or efaliztimab treatment for psoriasis patients or other treatments for PML patients.

In further embodiments, the NK cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycoplienolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 11; Henderson et al., Immun. 73:316-321, 1991; Bierer et al., Citrr. Opin. mm n. 5:763-773, 93).

In a further embodiment, the cell compositions of the present invention are administered to a patient in conjunction with (e.g., before, simultaneously or following) bone marrow transplantation, NK cell ablative therapy using either chemotherapy agents such as, fludarabine, external-beam radiation therapy (XRT), cyclophosphamide, or antibodies such as OKT3 or CAM PATH.

In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery. Said modified cells obtained by any one of the methods described here can be used in a particular aspect of the invention for treating patients in need thereof against Host versus Graft (HvG) rejection and Graft versus Host Disease (GvHD); therefore in the scope of the present invention is a method of treating patients in need thereof against Host versus Graft (HvG) rejection and Graft versus Host Disease (GvHD) comprising treating said patient by administering to said patient an effective amount of modified cells.

Other Definitions

Amino acid residues in a polypeptide sequence are designated herein according to the one-letter code, in which, for example, Q means Gln or Glutamine residue, R means Arg or Arginine residue and D means Asp or Aspartic acid residue.

Amino acid substitution means the replacement of one amino acid residue with another, for instance the replacement of an Arginine residue with a Glutamine residue in a peptide sequence is an amino acid substitution.

Nucleotides are designated as follows: one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

“As used herein, “nucleic acid” or “polynucleotides” refers to nucleotides and/or polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Nucleic acids can be either single stranded or double stranded.

by “polynucleotide successively comprising a first region of homology to sequences upstream of said double-stranded break, a sequence to be inserted in the genome of said cell and a second region of homology to sequences downstream of said double-stranded break” it is intended to mean a DNA construct or a matrix comprising a first and second portion that are homologous to regions 5' and 3' of a DNA target in situ. The DNA construct also comprises a third portion positioned between the first and second portion which comprise some homology with the corresponding DNA sequence in situ or alternatively comprise no homology with the regions 5' and 3' of the DNA target in situ. Following cleavage of the DNA target, a homologous recombination event is stimulated between the genome containing the targeted gene comprised in the locus of interest and this matrix, wherein the genomic sequence containing the DNA target is replaced by the third portion of the matrix and a variable part of the first and second portions of said matrix.

by “DNA target”, “DNA target sequence”, “target DNA sequence”, “nucleic acid target sequence”, “target sequence”, or “processing site” is intended a polynucleotide sequence that can be targeted and processed by a rare-cutting endonuclease according to the present invention. These terms refer to a specific DNA location, preferably a genomic location in a cell, but also a portion of genetic material that can exist independently to the main body of genetic material such as plasmids, episomes, virus, transposons or in organelles such as mitochondria as non-limiting example. As non-limiting examples of TALE-nuclease targets, targeted genomic sequences generally consist of two 17-bp long sequences (called half targets) separated by a 15-bp spacer. Each half-target is recognized by repeats of TALE-nucleases listed in tables 1-2 as non-limiting examples, encoded in plasmids, under the control of EF1-alpha promoter or T7 promoter. The nucleic acid target sequence is defined by the 5' to 3' sequence of one strand of said target, as indicated in Tables 1-2.

By “delivery vector” or “delivery vectors” is intended any delivery vector which can be used in the present invention to put into cell contact (i.e “contacting”) or deliver inside cells or subcellular compartments (i.e “introducing”) agents/chemicals and molecules (proteins or nucleic acids) needed in the present invention. It includes, but is not limited to liposomal delivery vectors, viral delivery vectors, drug delivery vectors, chemical carriers, polymeric carriers, lipoplexes, polyplexes, dendrimers, microbubbles (ultrasound contrast agents), nanoparticles, emulsions or other appropriate transfer vectors. These delivery vectors allow delivery of molecules, chemicals, macromolecules (genes, proteins), or other vectors such as plasmids, peptides developed by Diatos. In these cases, delivery vectors are molecule carriers. By “delivery vector” or “delivery vectors” are also intended delivery methods to perform transfection.

The terms “vector” or “vectors” refer to a nucleic acid molecule capable of transporting another nucleic acid to which it has been linked. A “vector” in the present invention includes, but is not limited to, a viral vector, a plasmid, a RNA vector or a linear or circular DNA or RNA molecule which may consists of a chromosomal, non chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available.

Viral vectors include retrovirus, adenovirus, parvovirus (e. g. adenoassociated viruses), coronavirus, negative strand RNA viruses such as orthomyxovirus (e. g., influenza virus), rhabdovirus (e. g., rabies and vesicular stomatitis virus), paramyxovirus (e. g. measles and Sendai), positive strand RNA viruses such as picornavirus and alphavirus, and double-stranded DNA viruses including adenovirus, herpes-virus (e. g., Herpes Simplex virus types 1 and 2, Epstein-Barr virus, cytomegalovirus), and poxvirus (e. g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, *lenti*-virus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

By "lentiviral vector" is meant HIV-Based lentiviral vectors that are very promising for gene delivery because of their relatively large packaging capacity, reduced immunogenicity and their ability to stably transduce with high efficiency a large range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration in the DNA of infected cells. By "integrative lentiviral vectors (or LV)", is meant such vectors as non-limiting example, that are able to integrate the genome of a target cell. At the opposite by "non integrative lentiviral vectors (or NILV)" is meant efficient gene delivery vectors that do not integrate the genome of a target cell through the action of the virus integrase.

Delivery vectors and vectors can be associated or combined with any cellular permeabilization techniques such as sonoporation or electroporation or derivatives of these techniques.

By cell or cells is intended any eukaryotic living cells, primary cells and cell lines derived from these organisms for in vitro cultures.

By "primary cell" or "primary cells" are intended cells taken directly from living tissue (i.e. biopsy material) and established for growth in vitro, that have undergone very few population doublings and are therefore more representative of the main functional components and characteristics of tissues from which they are derived from, in comparison to continuous tumorigenic or artificially immortalized cell lines.

by "mutation" is intended the substitution, deletion, insertion of up to one, two, three, four, five, six, seven, eight, nine, ten, eleven, twelve, thirteen, fourteen, fifteen, twenty, twenty five, thirty, fourty, fifty, or more nucleotides/amino acids in a polynucleotide (cDNA, gene) or a polypeptide sequence. The mutation can affect the coding sequence of a gene or its regulatory sequence. It may also affect the structure of the genomic sequence or the structure/stability of the encoded mRNA.

by "variant(s)", it is intended a repeat variant, a variant, a DNA binding variant, a TALE-nuclease variant, a polypeptide variant obtained by mutation or replacement of at least one residue in the amino acid sequence of the parent molecule.

by "functional variant" is intended a catalytically active mutant of a protein or a protein domain; such mutant may have the same activity compared to its parent protein or protein domain or additional properties, or higher or lower activity.

By "gene" is meant the basic unit of heredity, consisting of a segment of DNA arranged in a linear manner along a chromosome, which codes for a specific protein or segment of protein. A gene typically includes a promoter, a 5' untranslated region, one or more coding sequences (exons), optionally introns, a 3' untranslated region. The gene may further comprise a terminator, enhancers and/or silencers.

As used herein, the term "locus" is the specific physical location of a DNA sequence (e.g. of a gene) on a chromosome. The term "locus" can refer to the specific physical location of a rare-cutting endonuclease target sequence on a chromosome. Such a locus can comprise a target sequence that is recognized and/or cleaved by a rare-cutting endonuclease according to the invention. It is understood that the locus of interest of the present invention can not only qualify a nucleic acid sequence that exists in the main body of genetic material (i.e. in a chromosome) of a cell but also a portion of genetic material that can exist independently to said main body of genetic material such as plasmids, episomes, virus, transposons or in organelles such as mitochondria as non-limiting examples.

The term "endonuclease" refers to any wild-type or variant enzyme capable of catalyzing the hydrolysis (cleavage) of bonds between nucleic acids within a DNA or RNA molecule, preferably a DNA molecule. Endonucleases do not cleave the DNA or RNA molecule irrespective of its sequence, but recognize and cleave the DNA or RNA molecule at specific polynucleotide sequences, further referred to as "target sequences" or "target sites". Endonucleases can be classified as rare-cutting endonucleases when having typically a polynucleotide recognition site greater than 12 base pairs (bp) in length, more preferably of 14-55 bp. Rare-cutting endonucleases significantly increase HR by inducing DNA double-strand breaks (DSBs) at a defined locus (Rouet, Smih et al. 1994; Choulika, Perrin et al. 1995; Pingoud and Silva 2007). Rare-cutting endonucleases can for example be a homing endonuclease (Paques and Duchateau 2007), a chimeric Zinc-Finger nuclease (ZFN) resulting from the fusion of engineered zinc-finger domains with the catalytic domain of a restriction enzyme such as FokI (Porteus and Carroll 2005) or a chemical endonuclease (Eisenschmidt, Lanio et al. 2005; Arimondo, Thomas et al. 2006). In chemical endonucleases, a chemical or peptidic cleaver is conjugated either to a polymer of nucleic acids or to another DNA recognizing a specific target sequence, thereby targeting the cleavage activity to a specific sequence. Chemical endonucleases also encompass synthetic nucleases like conjugates of orthophenanthroline, a DNA cleaving molecule, and triplex-forming oligonucleotides (TFOs), known to bind specific DNA sequences (Kalish and Glazer 2005). Such chemical endonucleases are comprised in the term "endonuclease" according to the present invention.

Rare-cutting endonucleases can also be for example TALE-nucleases, a new class of chimeric nucleases using a FokI catalytic domain and a DNA binding domain derived from Transcription Activator Like Effector (TALE), a family of proteins used in the infection process by plant pathogens of the *Xanthomonas* genus (Boch, Scholze et al. 2009; Moscou and Bogdanove 2009; Christian, Cermak et al. 2010; Li, Huang et al.). The functional layout of a FokI-based TALE-nuclease (TALE-nuclease) is essentially that of a ZFN, with the Zinc-finger DNA binding domain being replaced by the TALE domain. As such, DNA cleavage by a TALE-nuclease requires two DNA recognition regions flanking an unspecific central region. Rare-cutting endonucleases encompassed in the present invention can also be derived from TALE-nucleases.

Rare-cutting endonuclease can be a homing endonuclease, also known under the name of meganuclease. Such homing endonucleases are well-known to the art (Stoddard 2005). Homing endonucleases recognize a DNA target sequence and generate a single- or double-strand break. Homing endonucleases are highly specific, recognizing DNA target sites ranging from 12 to 45 base pairs (bp) in length, usually ranging from 14 to 40 bp in length. The homing endonuclease according to the invention may for example correspond to a LAGLIDADG endonuclease, to a HNH endonuclease, or to a GIY-YIG endonuclease. Preferred homing endonuclease according to the present invention can be an I-CreI variant.

By a "TALE-nuclease" is intended a fusion protein consisting of a nucleic acid-binding domain typically derived from a Transcription Activator Like Effector (TALE) and one nuclease catalytic domain to cleave a nucleic acid target sequence. The catalytic domain is preferably a nuclease domain and more preferably a domain having endonuclease activity, like for instance I-TevI, ColE7, NucA and Fok-1. In a particular embodiment, the TALE domain can be fused to a meganuclease like for instance I-CreI and 1-OnuI or functional variant thereof. In a more preferred embodiment, said nuclease is a monomeric TALE-Nuclease. A monomeric TALE-Nuclease is a TALE-Nuclease that does not require dimerization for specific recognition and cleavage, such as the fusions of engineered TAL repeats with the catalytic domain of 1-TevI described in WO2012138927. Transcription Activator like Effector (TALE) are proteins from the bacterial species *Xanthomonas* comprise a plurality of repeated sequences, each repeat comprising di-residues in position 12 and 13 (RVD) that are specific to each nucleotide base of the nucleic acid targeted sequence. Binding domains with similar modular base-per-base nucleic acid binding properties (MBBBD) can also be derived from new modular proteins recently discovered by the applicant in a different bacterial species. The new modular proteins have the advantage of displaying more sequence variability than TAL repeats. Preferably, RVDs associated with recognition of the different nucleotides are HD for recognizing C, NG for recognizing T, NI for recognizing A, NN for recognizing G or A, NS for recognizing A, C, G or T, HG for recognizing T, IG for recognizing T, NK for recognizing G, HA for recognizing C, ND for recognizing C, HI for recognizing C, HN for recognizing G, NA for recognizing G, SN for recognizing G or A and YG for recognizing T, TL for recognizing A, VT for recognizing A or G and SW for recognizing A. In another embodiment, critical amino acids 12 and 13 can be mutated towards other amino acid residues in order to modulate their specificity towards nucleotides A, T, C and G and in particular to enhance this specificity. TALE-nuclease have been already described and used to stimulate gene targeting and gene modifications (Boch, Scholze et al. 2009; Moscou and Bogdanove 2009; Christian, Cermak et al. 2010; Li, Huang et al.). Engineered TAL-nucleases are commercially available under the trade name TALEN™ (Cellectis, 8 rue de la Croix Jarry, 75013 Paris, France).

The term "cleavage" refers to the breakage of the covalent backbone of a polynucleotide. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. Double stranded DNA, RNA, or DNA/RNA hybrid cleavage can result in the production of either blunt ends or staggered ends.

By "fusion protein" is intended the result of a well-known process in the art consisting in the joining of two or more genes which originally encode for separate proteins or part of them, the translation of said "fusion gene" resulting in a single polypeptide with functional properties derived from each of the original proteins.

"identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated.

"similarity" describes the relationship between the amino acid sequences of two or more polypeptides. BLASTP may also be used to identify an amino acid sequence having at least 70%, 75%, 80%, 85%, 87.5%, 90%, 92.5%, 95%, 97.5%, 98%, 99% sequence similarity to a reference amino acid sequence using a similarity matrix such as BLOSUM45, BLOSUM62 or BLOSUM80. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity of similarity to the amino acid sequences disclosed herein are contemplated and encompassed by this disclosure. The polynucleotide sequences of similar polypeptides are deduced using the genetic code and may be obtained by conventional means. A polynucleotide encoding such a functional variant would be produced by reverse translating its amino acid sequence using the genetic code.

"signal-transducing domain" or "co-stimulatory ligand" refers to a molecule on an antigen presenting cell that specifically binds a cognate co-stimulatory molecule on a NK-cell, thereby providing a signal which, in addition to the primary signal provided by, for instance, binding of a TCR/CD3 complex with an MHC molecule loaded with peptide, mediates a NK cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible costimulatory ligand (ICOS-L), intercellular adhesion molecule (ICAM, CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a NK cell, such as but not limited to, CD27, CD28, 4-IBB, OX40, CD30, CD40, PD-1, ICOS, lymphocyte function-associated antigen-1 (LFA-1), CD2, CD7, LTGHT, NKG2C, B7-H3, a ligand that specifically binds with CD83.

A "co-stimulatory molecule" refers to the cognate binding partner on a NK cell that specifically binds with a co-stimulatory ligand, thereby mediating a co-stimulatory response by the cell, such as, but not limited to proliferation. Co-stimulatory molecules include, but are not limited to an MHC class I molecule, BTLA and Toll ligand receptor.

A "co-stimulatory signal" as used herein refers to a signal, which in combination with primary signal, such as TCR/CD3 ligation, leads to NK cell proliferation and/or upregulation or downregulation of key molecules.

"bispecific antibody" refers to an antibody that has binding sites for two different antigens within a single antibody molecule. It will be appreciated by those skilled in the art that other molecules in addition to the canonical antibody structure may be constructed with two binding specificities. It will further be appreciated that antigen binding by bispecific antibodies may be simultaneous or sequential. Bispecific antibodies can be produced by chemical techniques (see e.g., Kranz et al. (1981) Proc. Natl. Acad. Sci. USA 78, 5807), by "polydoma" techniques (See U.S. Pat. No. 4,474,893) or by recombinant DNA techniques, which all are known per se. As a non limiting example, each binding domain comprises at least one variable region from an antibody heavy chain ("VH or H region"), wherein the VH region of the first binding domain specifically binds to the lymphocyte marker such as CD3, and the VH region of the second binding domain specifically binds to tumor antigen.

The term "extracellular ligand-binding domain" as used herein is defined as an oligo- or polypeptide that is capable of binding a ligand. Preferably, the domain will be capable of interacting with a cell surface molecule. For example, the extracellular ligand-binding domain may be chosen to recognize a ligand that acts as a cell surface marker on target cells associated with a particular disease state. Thus examples of cell surface markers that may act as ligands include those associated with viral, bacterial and parasitic infections, autoimmune disease and cancer cells.

The term "subject" or "patient" as used herein includes all members of the animal kingdom including non-human primates and humans.

The above written description of the invention provides a manner and process of making and using it such that any person skilled in this art is enabled to make and use the same, this enablement being provided in particular for the subject matter of the appended claims, which make up a part of the original description.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding can be obtained by reference to certain specific examples, which are provided herein for purposes of illustration only, and are not intended to be limiting unless otherwise specified.

EXAMPLES

General Methods

Primary NK-Cell Cultures

NK cells from a health donor were purified from Buffy coat samples provided by EFS (Etablissement Francais du Sang, Paris, France) using Ficoll gradient density medium. (NK Cell Isolation Kit Miltenyi Biotec #130-092-657). PBMC are washed in PBS/SVF 2%/EDTA 2 mM and then filtrated (Pre-Separation filters 30 μm Miltenyi Biotec #130-041-407). Other cells thant NK cells (monocytes, lymphocytes B, lymphocytes T etc.) are labeled by using a beads cocktail charged with antibodies and magetically retained on column (LS Columns Miltenyi Biotec #130-042-401). NK cells obtained in the eluted fraction are activated by beads charged with biotinlylated anti-CD2 et anti-CD335 (NKp46) antibodies (NK cell activation/expansion Kit Miltenyi Biotec #130-094-483) and then allowed to grow to $2.10^6$ cells/mL in plaque 12 W or 6 W in culture medium X-Vivo 15 (Lonza #04-418Q) supplemented with 5% of human serum AB (Seralab #100-318) and IL-2 500UI/mL (Miltenyi Biotec #130-093-903)+IL-15 100UI/mL (Miltenyi Biotec). After 6 days of culture, the medium is replaced and fresh one is added every 3-4 days. From day D=15, the expansion is evaluated as well as the phenotype of the cells.

TALE-Nuclease-Mediated Inactivation Gene of NK Cell

To inactivate a gene such as one described here, two pairs of TALE-nucleases were designed for each gene, assembled and validated by sequencing. Once validated, mRNAs encoding the two TALE-nucleases were produced, polyadenylated and used to electroporate NK cells using pulse agile technology (5 or 10 μg of TALE-nuclease mRNA left and right were used) such as described in the WO 2013/176915. A cold temperature shock are usually performed by incubating NK cells at 30° C. immediately after electroporation and for 24 hours. A reactivation (12.5 μl beads/$10^6$ cells) was performed at D8 (8 days after the electroporation). The resulting NK cells were allowed to grow and eventually characterized genotypically (by Endo T7 assay and deep sequencing at the gene loci to target) as well as phenotypically. Their phenotypical characterization consisted in the labelling with anti-CD56, anti-CD3 and anti-CD16 mAbs coupled to different flurochromes APC (Miltenyi). CD56/CD3 and CD16 labellings were monitored by FACS at days, 0, +10 and +20. By this way, it is possible to discriminate between NK subpopulations of those displaying a slow proliferation/very high cytotoxicity (N K CD56$^{dim}$CD16+) with NK cells producing a lot of cytokines, fast proliferation and less cytotoxicity (NK CD56$^{bright}$CD16−).

Genotypic Characterization of NK Cells Having Undergone a KO in a Functionality Related Gene This protocol may be used to assess the efficiency of functionality-related gene inactivation. Accordingly, cells transfected with either 5 or 10 μg of TALE-nuclease mRNA were grown for 4 days (D4, 4 days after electroporation) and collected to perform T7 assays at the locus of interest. The T7 assay protocol is described in Reyon, D., Tsai, S. Q., Khayter, C., Foden, J. A., Sander, J. D., and Joung, J. K. (2012) FLASH assembly of TALE-nucleases for high-throughput genome editing. *Nat Biotechnologies.*

Determination of Growth Rate of NK Cells with a KO in the Gene of Interest (GOI)

NK cells with a GOI-KO are tested for their growth rate and for their reactivation with respect to WT cells.

CAR mRNA Transfection

Transfections were done at Day 4 or Day 11 after NK-cell purification and activation. 5 millions of cells were transfected with 15 μg of mRNA encoding the different CAR constructs. CAR mRNAs were produced using T7 mRNA polymerase transfections done using Cytopulse technology, by applying two 0.1 mS pulses at 3000V/cm followed by four 0.2 mS pulses at 325V/cm in 0.4 cm gap cuvettes in a final volume of 200 μl of "Cytoporation buffer T" (BTX Harvard Apparatus). Cells were immediately diluted in X-Vivo™-15 media and incubated at 37° C. with 5% $CO_2$. IL-2 was added 2 h after electroporation at 20 ng/mL.

NK Cell Transduction

Transduction of NK cells with recombinant lentiviral vectors expression the CAR was carried out three days after NK cell purification/activation. CAR detection at the surface of NK cells was done using a recombinant protein consisting on the fusion of the extracellular domain of the tumoral target protein, together with a murine IgG1 Fc fragment. Binding of this protein to the CAR molecule was detected with a fluorochrome-conjugated secondary antibody targeting the mouse Fc portion of the protein, and analyzed by flow cytometry.

Cytotoxicity Assay

NK cells were incubated in 96-well plates (100,000 cells/well), together with 10,000 target cells (expressing the CAR targeting the tumoral antigen) and 10,000 control (not expressing the anti-target CAR; "negative control") cells in the same well. Target and control cells were labelled with fluorescent intracellular dyes (CFSE or Cell Trace Violet) before co-culturing them with CAR+NK-cells. The co-cultures were incubated for 4 hours at 37° C. with 5% $CO_2$. After this incubation period, cells were labelled with a fixable viability dye and analyzed by flow cytometry. Viability of each cellular population (target cells or neg control cells) was determined and the % of specific cell lysis was calculated. Cytotoxicity assays were carried out 48 h after mRNA transfection.

Example 1: NK Cells Transfection by GFP

A bulk of 2.5 $10^6$ NK cells from PBMCs of a healthy donor were transfected with 5 μg of RNA encoding for GFP (SEQ ID NO.30) in order to show the transfection rate compared to negative control (no RNA is transfected). After 72 hours of transfection, NK cells were labeled with FITC and analyzed by FACS.

Figure 1B:
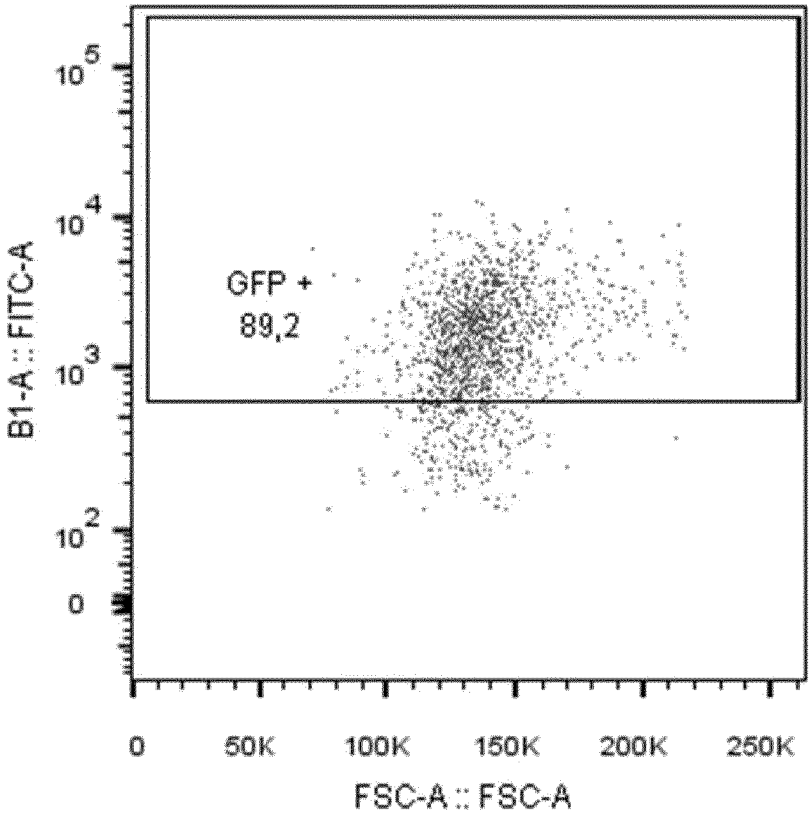

The results are presented in FIG. 1. About 79% of GFP transfected NK cells are obtained compared to the negative control (no RNA). This experiment shows that NK cells the transfection conditions and protocol are satisfactory for carrying further genetic engineering experiments.

Example 2: Knock Out of Beta2 Microglobulin (β2M) Gene in NK Cell

Since NK cells alike all mammalian cells bear MHCI which is constituted of a heavy chain (variable and presenting the antigenic peptide) and a non-variable chain (beta2m). The absence of beta2m prevents the expression of the heavy chain on the cell surface, making the cells de facto MHCI KO. The Knock out of beta2 microglobulin (β2M) gene in NK cells aims to make them invisible to the host T cells. As all the cells from an individual carry the MHCI, constituted of a heavy chain (variable and presenting the antigenic peptide) and a constant chain (B2M). The absence of B2M prevents the expression of heavy chain on the cell surface, and thus a B2M KO cell is in facto MHCI KO.

A bulk of 2.5 $10^6$ NK cells from PBMCs of a healthy donor were transfected with 20 μg of RNA encoding for TALE-nucleases (SEQ ID NO:21 and 22) in order to inactivate the gene coding for beta2 microglobulin β2M). After 72 hours of transfection, NK cells were labeled with a β2M specific antibody, and analyzed by FACS.

Figure 2A:
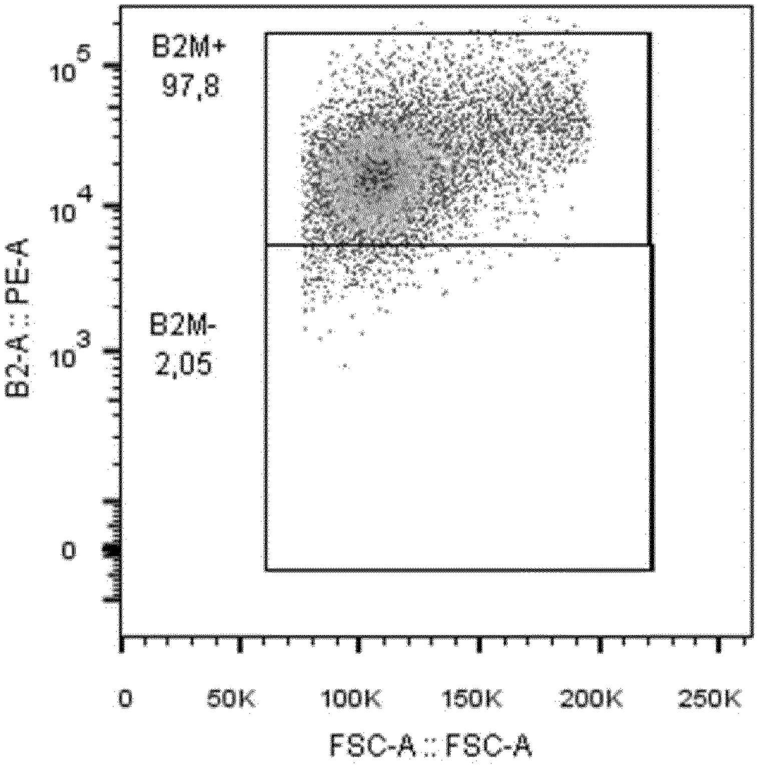
FIG. 2: FACS results obtained 72 hours after transfection for KO of β2M gene: the upper panel (FIG. 2A) represents the negative control (untransfected NK cells), the lower panel (FIG. 2B) represents the transfection using 10 μg de RNA encoding for each TALE-nuclease; 2.5 $10^6$ of NK cells were used in each case.
Figure 2B:
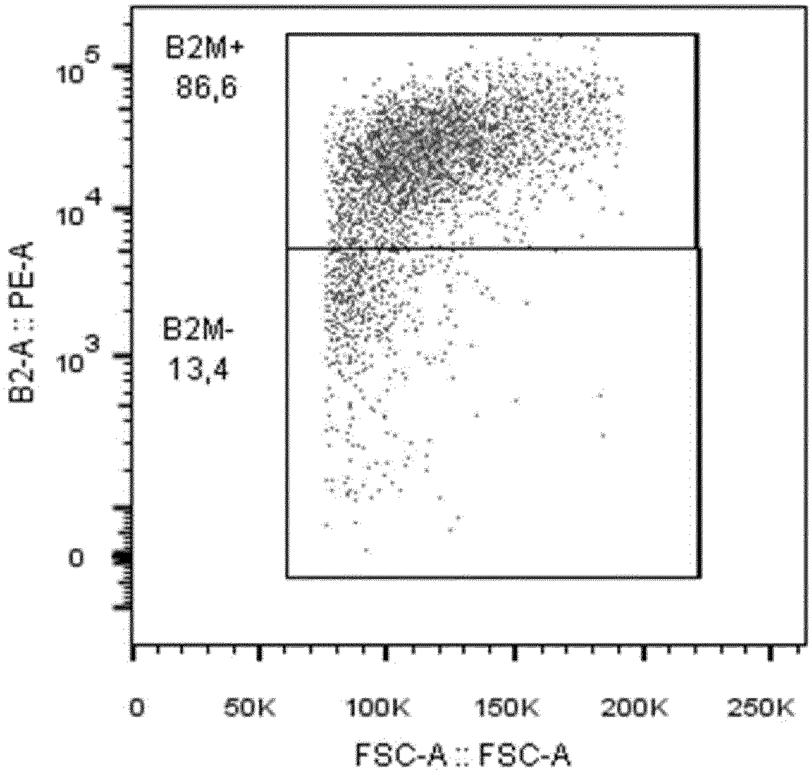

The results are presented in FIG. 2. About 11% of KO on (32M gene is obtained compared to the wild type (WT) control.

Example 3: Knock Out of TGFβ Gene in NK Cell

The presence of TGFβ at the plasma membrane of Treg has been shown to bind to TGFβ receptor expressed by NK cells and suppress their cytotoxic functions toward tumor cells. To prevent Treg dependant inhibition of NK cells, we inactivated their TGFβ receptor-target TGFβ coding sequence exon 2 (SEQ ID No 1) using Left TALEN arm (SEQ ID No 2) having DNA binding domain RVDs; Right TALEN arm (SEQ ID No 3) having DNA binding domain RVDs; all these sequences being inserted in Table 1. Transfection of mRNA encoding TALEN pair in NK cells resulted in efficient processing of TGFβ coding sequence and impairment of its surface membrane expression. Such inactivation resulted in the enhancement of NK cytolytic functions toward target tumor cells.

Example 4: Knock Out of E3 Ligase Cbl-b. Gene

The cytotoxic function of NK cell toward tumor metastasis has been shown to be inhibited by E3 ubiquitine ligase Cbl-b (GenBank accession number NC_000003).

Two sets of specific TALENs were produced. The first one targets a sequence (SEQ ID No 4) within the second coding exon of the Cbl-b gene (Left TALEN arm (SEQ ID No 5) with its DNA binding domain RVDs; and Right TALEN arm (SEQ ID No 6) with its DNA binding domain RVDs; all these sequence being inserted in Table 2.

A second one targets a sequence (SEQ ID No 7) within the third coding exon of the Cbl-b gene; Left TALEN arm of SEQ ID No 8 with its DNA binding domain RVDs; Right TALEN arm of SEQ ID No 9 with its DNA binding domain RVDs; all being inserted in the Table 2.

To test the ability of these Cbl-b specific TALENs to promote error-prone NHEJ events at the Cbl-b locus, 5 or 10 μg of mRNA encoding TALENs were electroporated into primary NK cells using Pulse Agile technology according to the manufacturer protocol. Transfection of mRNA encoding TALEN pair in NK cells resulted in efficient processing of its coding sequence and impairment of the expression of the related protein. Inactivation of E3 ubiquitine ligase Cbl-b resulted in the enhancement of cytolytic activity of NK Cell toward target tumor cells.

The invention claimed is:

1. An in vitro method for enhancing cytolytic activity of a natural killer (NK) cell towards a target tumor cell, the method comprising:

(a) transfecting by electroporation the primary NK cell with mRNA encoding a TAL-nuclease that targets an exon of the gene encoding TGFBRII in said primary NK cell, wherein the TALE-nuclease cleaves the gene encoding TGFBRII in the genome of the primary NK cell in the target exon to inactivate TGFβ receptor gene expression so that the TGFβ receptor gene is not expressed in a functional protein form in said primary NK cell; and (b) introducing an AAV or lentiviral vector comprising a nucleic acid encoding a chimeric antigen receptor (CAR) directed against at least one antigen expressed on the surface the target tumor cell to produce an engineered NK cell that expresses the CAR and lacks expression of the TGFβ receptor, wherein the engineered NK cell has enhanced cytolytic activity towards the target tumor cell as compared to a NK cell expressing a CAR but having intact endogenous expression of TGFβ receptor.

2. The method according to claim 1, wherein the mRNA encoding a TALEN pair that targets the exon of the gene encoding TGFBRII comprise SEQ ID No: 2-3.

3. The method according to claim 1, wherein a double gene knock out is performed and wherein the second gene knocked out is selected from genes encoding Cbl-B, A2A receptor, KLRD1, LIR1/ILT2, KIRs, CD94, Fas, AhR, Tim-3, Tyro-3, GCN2, CD94, cyclophilin A, TBL1XR1, HPRT, CD52, beta2M and PD-1.

4. The method according to claim 1, wherein said nucleotide sequence encoding said CAR is introduced into the NK cell by lentiviral transduction.

5. The method according to claim 1, further comprising the step of expanding the resulting NK cell.

6. The method of claim 1, wherein the electroporation is a cytopulse electroporation that comprises first high electric field pulse allowing pore formation, and subsequent lower electric field pulse(s) to allow to move the polynucleotides into the cell.

7. The method of claim 1, wherein the nucleic acid encoding a chimeric antigen receptor (CAR) directed against at least one antigen expressed on the surface the target tumor cell is integrated into the genome of the engineered NK cell.

8. The method of claim 1, wherein the nucleic acid encoding a chimeric antigen receptor (CAR) directed against at least one antigen expressed on the surface the target tumor cell is not integrated into the genome of the engineered NK cell.

* * * * *